United States Patent
Desai et al.

(10) Patent No.: US 10,550,150 B2
(45) Date of Patent: Feb. 4, 2020

(54) SHORT-CHAIN PEPTIDES AS KAPPA (κ) OPIOID RECEPTORS (KOR) AGONIST

(71) Applicant: CADILA HEALTHCARE LIMITED, Gujarat, Ahmedabad (IN)

(72) Inventors: Ranjit Desai, Ahmedabad (IN); Rajesh Bahekar, Ahmedabad (IN); Vijay Prajapati, Ahmedabad (IN); Rajendra Chopade, Ahmedabad (IN)

(73) Assignee: CADILA HEALTHCARE LIMITED, Ahmedabad, Gujarat (IN)

(*) Notice: Subject to any disclaimer, the term of this patent is extended or adjusted under 35 U.S.C. 154(b) by 166 days.

(21) Appl. No.: 15/571,318

(22) PCT Filed: May 9, 2016

(86) PCT No.: PCT/IN2016/000120
§ 371 (c)(1),
(2) Date: Nov. 2, 2017

(87) PCT Pub. No.: WO2016/181408
PCT Pub. Date: Nov. 17, 2016

(65) Prior Publication Data
US 2018/0282369 A1 Oct. 4, 2018

(30) Foreign Application Priority Data
May 11, 2015 (IN) .......................... 1849/MUM/2015

(51) Int. Cl.
*A61K 38/07* (2006.01)
*C07K 5/107* (2006.01)
*A61K 45/06* (2006.01)
*A61P 29/00* (2006.01)

(52) U.S. Cl.
CPC ............ *C07K 5/1016* (2013.01); *A61K 38/07* (2013.01); *A61K 45/06* (2013.01); *A61P 29/00* (2018.01)

(58) Field of Classification Search
None
See application file for complete search history.

(56) References Cited

U.S. PATENT DOCUMENTS

| 5,672,601 A | 9/1997 | Cignarella |
| 2010/0029575 A1 | 2/2010 | Junien et al. |

FOREIGN PATENT DOCUMENTS

| WO | WO 2008/057608 | 5/2008 |
| WO | WO 2013/184794 | 12/2013 |

OTHER PUBLICATIONS

International Preliminary Report on Patentability with Amended Sheets, for PCT/IN2016/000120, dated Jul. 20, 2017, 20 pages.
Written Opinion of the ISA for PCT/IN2016/000120, dated Nov. 24, 2016, 9 pages.

*Primary Examiner* — Fred H Reynolds
(74) *Attorney, Agent, or Firm* — Nixon & Vanderhye P.C.

(57) ABSTRACT

The present invention relates to novel short-chain peptides of the general formula (I), which are selective and peripherally acting KOR agonist, their tautomeric forms, their enantiomers, their diastereoisomers, their stereoisomers, their pharmaceutically accepted salts, or prodrugs thereof which are useful in the treatment or prevention of diseases in which the Kappa (κ) opioid receptors (KOR) are involved, such as treatment or prevention of visceral pain, hyperalgesia, rheumatoid arthritic inflammation, osteoarthritic inflammation, IBD inflammation, IBS inflammation, ocular inflammation, otitic inflammation or autoimmune inflammation. The invention also relates to process for the manufacture of said short-chain peptides, and pharmaceutical compositions containing them and their use.

8 Claims, No Drawings

SHORT-CHAIN PEPTIDES AS KAPPA (κ) OPIOID RECEPTORS (KOR) AGONIST

This application is the U.S. national phase of International Application No. PCT/IN2016/000120 filed 9 May 2016, which designated the U.S. and claims priority to IN Patent Application No. 1849/MUM/2015 filed 11 May 2015, the entire contents of each of which are hereby incorporated by reference.

FIELD OF INVENTION

The present invention relates to novel short-chain peptides of the general formula (I), which are selective and peripherally acting KOR agonist, their tautomeric forms, their enantiomers, their diastereoisomers, their stereoisomers, their pharmaceutically accepted salts, or prodrugs thereof which are useful in the treatment or prevention of diseases in which the Kappa (κ) opioid receptors (KOR) are involved, such as treatment or prevention of visceral pain, hyperalgesia, rheumatoid arthritic inflammation, osteoarthritic inflammation, IBD inflammation, IBS inflammation, ocular inflammation, otitic inflammation or autoimmune inflammation. The invention also relates to process for the manufacture of said compounds, and pharmaceutical compositions containing them and their use.

BACKGROUND OF THE INVENTION

There are three types of opioid receptors (Mu (μ), Kappa (κ) and Delta (δ)), found to be expressed in both the CNS and in the periphery and the available opioid analgesics mediate their effects through these opioid receptors (Evans, C., Keith, J. D., Morrison, H., Magendzo, K and Edwards, R., Science, 258, 1952-1955, 1992; Cox, B. M., Mol. Pharmacol., 83, 723-728, 2013; Chen, Y., Mestek, A., Liu, J., Hurley, J and Yu, L., Mol. Pharmacol., 44, 8-12, 1993; Meng, F., Xie, G. X., Thompson, R., Mansour, A., Goldstein, A., Watson, S. J and Akil, H., Proc. Natl. Acad. Sci., U.S.A., 90, 9954-9958, 1993; Simonin, F., Gaveriaux, R. C., Befort, K., Matthes, H., Lannes, B., Micheletti, G., Mattei, M. G., Charron, G., Bloch, B and Kieffer, B., Proc. Natl. Acad. Sci., U.S.A., 92, 7006-7010, 1995; Stein, C., Anesth. Analg., 76, 182-191, 1993). Most of the opioid analgesics at present, for example, morphine, act by binding to the μ-opioid receptor, and their analgesic activity are associated with a spectrum of undesirable side effects, such as physical dependence, respiratory depression, urinary retention, constipation, euphoria/dysphoria and constipation (Pasternak, G. W., Clin. Neuropharmacol., 16, 1-18, 1993).

In recent years, considerable attention has been focused on the development of receptor selective κ-agonists as potent and efficacious analgesics devoid of the undesirable side effects of the μ analgesics (Barber, A and Gottschlich, R., Med. Res. Rev., 12, 525-562, 1992). Unlike agonist at δ and μ receptors, agonist at κ-opioid receptors does not elicit constipation and euphoria. The κ-opioid receptors are members of the superfamily of G protein-coupled receptors (GPCRs). Agonist binding to the κ-receptors, activates the intracellular associated Gi protein, which decreases $Ca^{2+}$ channel conductance or inhibits adenylyl cyclase (AC) (Prather, P. L., McGinn, T. M., Claude, P. A., Liu-Chen, L. Y., Loh, H. H and Law, P. Y., Mol. Brain. Res., 29, 336-346, 1995).

κ-opioid agonists have been suggested to have potential for treatment of incisional/inflammatory pain, burn injury pain (Field, M. J., Carrell, A. J., Gonzalez, M. I., McCleary, S., Oles, R. J., Smith, R., Hughes, J and Singh, L., Pain, 80, 383-389, 1999), neuropathic pain (Catheline, G., Guilbaud, G and Kayser, V., Eur. J. Pharmacol., 357, 171-178, 1998), visceral pain including dysmenorrhea or gastrointestinal pain (Delgado Aros S., Chial H. J., Camilleri M., Szarka L. A., Weber F. T., Jacob, J., Ferber, I., McKinzie, S., Burton, D. D and Zinsmeister, A. R., Am. J. Physiol. Gastrointest. Liver Phsyiol., 284, G558-G566, 2002), Irritable bowel syndrome (IBS) (Dapoigny, M., Abitbol, J. L., Fraitag, B., Digest. Dis. Sci., 40, 2244-2249, 1995; Mangel, A. W., Bornstein, J. D., Hamm, L. R., Buda, J., Wang, J., Irish, W., Urso, D., Pharmacol. Ther., 28, 239-249, 2008), rheumatoid arthritis (Endoh, T., Tajima, A., Suzuki, T., Kamei, J., Suzuki, T., Narita, M., Tseng, L and Nagase, H., Eur. J. Pharmacol. 387, 133-140, 2000) and anti-pruritis effects (Peters, G and Gaylor, S., Clin. Pharmacol. Ther., 51, PPF-5, 1989). Walker et al., (Walker, J. S., Adv. Exp. Med. Biol., 521, 148-60, 2003) appraised the anti-inflammatory properties of kappa agonists for treatment of osteoarthritis, rheumatoid arthritis, inflammatory bowel disease and eczema.

Bileviciute-Ljungar et al., (Bileviciute-Ljungar, T. Saxne, and M. Spetea, Rheumatology, 45, 295-302, 2006) describe the reduction of pain and degeneration in Freund's adjuvant-induced arthritis by the kappa agonist U-50,488. Thus, the κ-receptors represent important therapeutic targets (Pan, Z. Z., Tershner, S. A., Fields, H. L., Nature, 389, 382-385, 1997; Chavkin, C., Neuropsychopharmacology, 36, 369-370, 2011).

κ-opioid receptors exist extensively in the central nervous system (CNS) and play important roles in many physiological and pathological functions. Inspite of such potential applications, clinical studies have shown that κ-receptor agonist elicit severe centrally mediated side effects generally described as "dysphoric actions" (Pfeiffer, A., Brantl, V., Herz, A and Emrich, H. M., Science, 233, 774-776, 1986), water diuresis (Dykstra, L. A., Gmerek, D. E., Winger, G and Woods, J. H., J. Pharmacol. Exp. Ther., 242, 413-420, 1987) and psychotomimetic effects (Rimoy, G. H., Wright, D. M., Bhaskar, N. K., Rubin, P. C, Eur. J. Clin. Pharmacol. 46 (3), 203-207, 1994). These side effects have apparently halted further clinical development for this class of compounds. Many studies have shown that opiates have peripheral analgesic effects, especially under inflammatory or hyperalgesic conditions (Barber, A and Gottschlich, R., Med. Res. Rev., 12, 525-562, 1992).

Agonist at κ-opioid receptors have been shown to produce analgesia and decrease inflammation in models of rheumatoid arthritis after local administration (Wilson, J. L., Nayanar, V and Walker, J. S., Br. J. Pharmacol., 118, 1754-1760, 1996). Restricted CNS penetration is a common strategy to reduce central side effects of drugs with beneficial peripheral actions. Attempts have been made to develop peripherally restricted κ-opioid agonists, such as ICI204448 (Shaw, J. S., Carroll, J. A., Alcoc, P and Main, B. G., Br. J. Pharmacol., 96, 986-992, 1989), GR94839 (Rogers, H., Birch, P. J., Harrison, S. M., Palmer, E., Manchee, G. R., Judd, D. B., Naylor, A., Scopes, D. I. C and Hayes, A. G., Br. J. Pharmacol., 106, 783-789, 1992), Cadila Healthcare Ltd., Novel Heterocyclic compounds as Kappa Opioid Agonist (WO2015/119660) and EMD61753/Asimadoline (Barber, A., Bartoszyk, G. D., Bender, H. M., Gottschlich, R., Greiner, H. E., Harting, J., Mauler, F., Minck, K. O., Murray, R. D., Simon, M and Seyfried, C. A., Br. J. Pharmacol., 113, 1317-1327, 1994).

Unfortunately, most of these compounds were discontinued in clinical trials either due to poor bioavailability, lack of efficacy or CNS side effects at analgesic doses (Barber, A and Gottschlich, R., Exp. Opin. Invest. Drugs, 6, 1351-1368, 1997). Asimadoline was designed and synthesized to differentiate itself from other reported peripheral KOR agonists such as ICI 204448, GR94839, and BRL 52974. Asimadoline is an amphiphilic molecule that contains a hydrophobic diphenyl methyl group and a hydrophilic hydroxyl group. Asimadoline successfully passed a phase II clinical trial for irritable bowel syndrome (IBS) indication/treatment and currently, it is under phase III clinical trial for the treatment of patients with diarrhea-predominant IBS (D-IBS).

CR665 and CR845 are tetrapeptides consisting of all D-amino acids that bind very potently and selectively to KOR. Dooley et al., (Dooley, C. T., Ny, P., Bidlack, J. M and Houghten, R. A., J. Biol. Chem., 273, 18848-18856, 1998) reported the discovery of tetrapeptide (FE200041/CR665) as a high affinity and selective κ-opioid agonist. The data demonstrate that FE200041 is a highly selective κ-opioid antinociceptive agent without CNS side effects at doses higher than efficacy doses. The peripheral antinociceptive actions of FE20041 suggest that it is possible to develop peripherally restricted opioid peptides for use in controlling pain. In Phase I study, CR845 appeared to be well tolerated with no signs of dysphoria or psychotomimetic effects. However, in Phase III study CR845 was on clinical hold due to hypematremia (elevated sodium level in blood).

Cara Therapeutics Inc., discloses synthetic peptide amide ligands as peripheral KOR agonist, useful for the treatment of pain and inflammation associated with a variety of diseases and conditions (WO99/32510; US2008/7402564; US2009/0075907; US2009/0156508; US2009/0264373; US2010/7727963; US2010/0075910; US2010/7713937; US2010/7842662; US2010/0029575; US2011/0118186; US2011/0257105; US2011/0212882; US2013/0012448; WO2007/139921; WO2008/060552; WO2013/184794; WO2015/065867 and US2015/0150935). Patent Application from Cara therapeutics (WO2008057608) discloses synthetic peptide amide compounds of the following general formula as κ-opioid receptors.

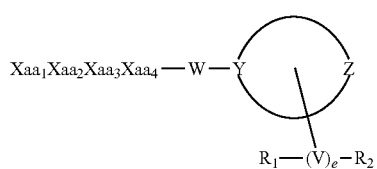

Wherein the moiety

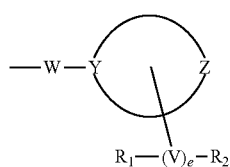

selected from

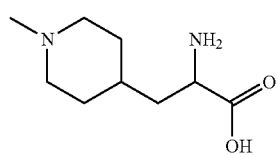

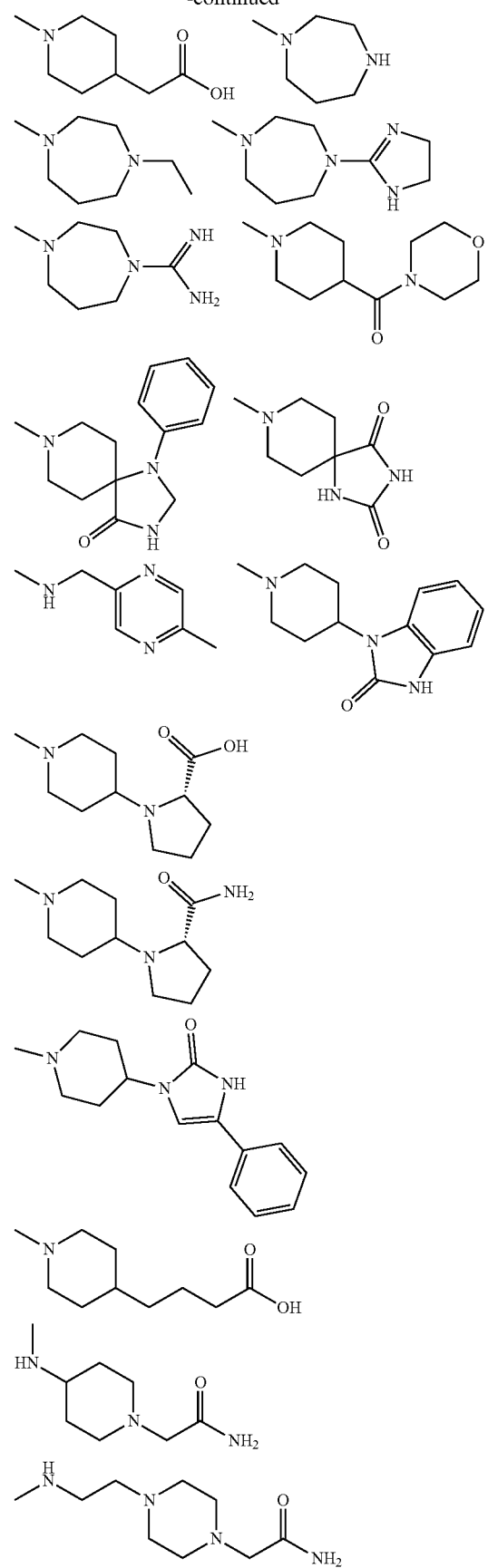

-continued

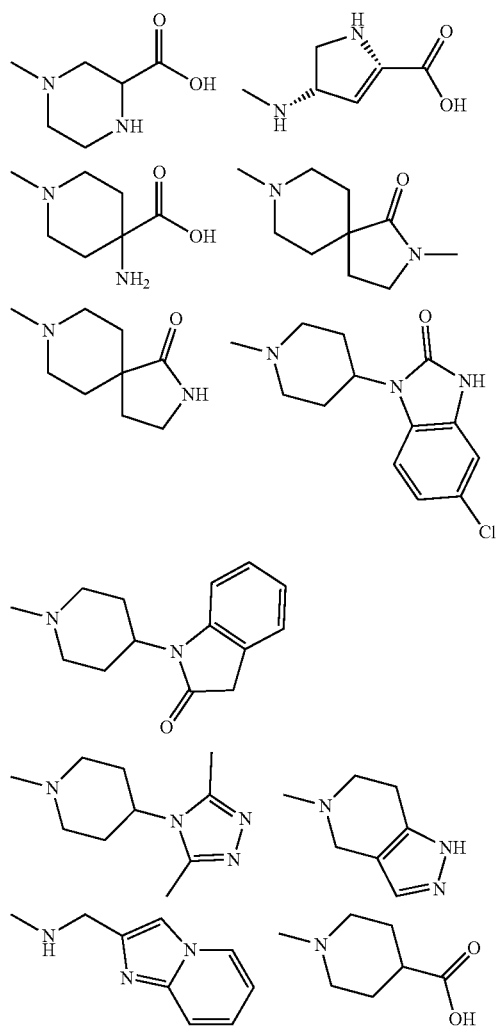

Considering the potential of KOR agonist in controlling/preventing visceral pain, hyperalgesia, rheumatoid arthritic inflammation, osteoarthritic inflammation, IBD inflammation, IBS inflammation, ocular inflammation, otitic inflammation or autoimmune inflammatory conditions, we initially prepared few short-chain peptides (two compounds, as listed in WO2008/057608, Chart-1) and their analogs.

Chart-1: Structures of literature compounds, reported in WO2008/057608

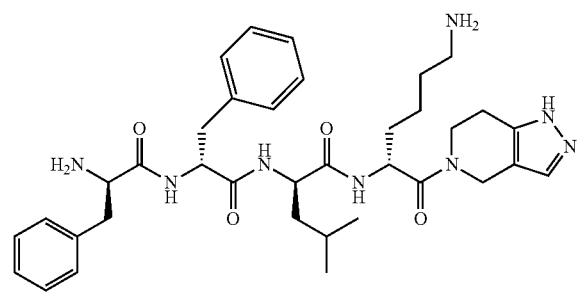

D-Phe-D-Phe-D-Leu-D-Lys-
[4,5,6,7-tetrahydro-1H-pyrazolo[4,3-c]pyridine amide]

-continued

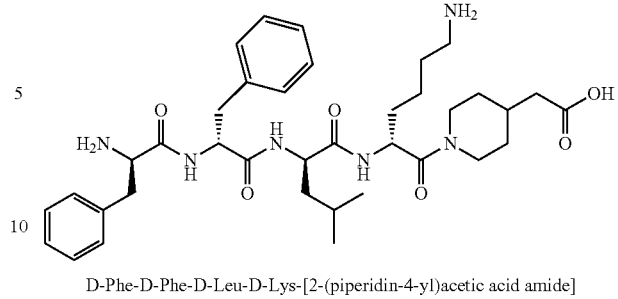

D-Phe-D-Phe-D-Leu-D-Lys-[2-(piperidin-4-yl)acetic acid amide]

However, these synthetic peptides did not show potent in vitro kappa opioid receptor agonistic activity ($EC_{50} > 10$ nM concentration) or in vivo activity in the acetic acid induced writhing model (in vivo antinociceptive activity, $ED_{50} > 3$ mg/kg, iv dose). Surprisingly, certain bicycle containing peptides (such as, compounds 4, 5, 15, 16, 35, 36 and 37, listed in Table 1) showed potent in vitro KOR agonistic activity ($EC_{50} < 100$ pM concentration, Table-4) and in vivo efficacy, in the acetic acid induced writhing model (in vivo antinociceptive activity, $ED_{50} \leq 0.1$ mg/kg, iv dose, Table 5). This clearly indicate that right end of the synthetic peptide (nitrogen containing bicyclic and bridged cyclic ring system) is one of the important factors required to provide potent in vitro KOR agonistic activity and in vivo antinociceptive activity, in this class of molecules.

We herein disclose series of novel short-chain peptides of the general formula (I), which are selective and peripheral KOR agonist, useful for the treatment or prevention of diseases in which the Kappa (κ) opioid receptors (KOR) are involved, such as treatment or prevention of visceral pain, hyperalgesia, rheumatoid arthritic inflammation, osteoarthritic inflammation, IBD inflammation, IBS inflammation, ocular inflammation, otitic inflammation or autoimmune inflammation.

SUMMARY OF THE INVENTION

The present invention relates to novel short-chain peptides of the general formula (I) their tautomeric forms, their enantiomers, their diastereoisomers, their stereoisomers, their pharmaceutically accepted salts, which are useful in the treatment or prevention of diseases in which the Kappa (κ) opioid receptors (KOR) are involved, such as treatment or prevention of visceral pain, hyperalgesia, rheumatoid arthritis inflammation, osteoarthritic inflammation, IBD inflammation, IBS inflammation, ocular inflammation, otitis inflammation or autoimmune inflammation. The invention also relates to process for the manufacture of said compounds, and pharmaceutical compositions containing them and their use.

A-B-C-D-E (Formula I)

EMBODIMENT(S) OF THE INVENTION

An embodiment of the present invention provides novel short-chain peptides of the general formula (I), their tautomeric forms, their enantiomers, their diastereoisomers, their stereoisomers, their pharmaceutically acceptable salts, and pharmaceutical compositions containing them or their suitable mixtures.

In a further embodiment of the present invention is provided pharmaceutical composition containing short-chain peptides of the general formula (I), their tautomeric forms, their enantiomers, their diastereoisomers, their stereoisomers, their pharmaceutically acceptable salts, or their mixtures in combination with suitable carriers, solvents, diluents and other media normally employed in preparing such compositions.

In a still further embodiment is provided the use of novel short-chain peptides of the present invention as KOR agonist, by administering a therapeutically effective and non-toxic amount of short-chain peptides of general formula (I) or their pharmaceutically acceptable compositions to the mammals.

In yet another embodiment are provided processes for the preparation of the short-chain peptides of formula (I) or their pharmaceutically acceptable salts, tautomers and enantiomeric forms.

List of abbreviations used in the description of the preparation of the compounds of the present invention:
AC: Adenylyl cyclase
ACN: Acetonitrile
Ala: Alanine
Asn: Asparagine
Asp: Aspartic acid
Arg: Arginine
Boc: tert-butoxycarbonyl
BOP: Benzotriazole-1-yl-oxy-tris-(dimethylamino)-phosphonium hexafluorophosphate
Cbz: Benzyloxycarbonyl
CNS: Central nervous system
DCC: N,N'-Dicyclohexyl carbodiimide
DIPCDI: N,N'-Diisopropyl carbodiimide
DCM: Dichloromethane
DIPEA: N,N-diisopropylethylamine
DMAP: Dimethyl amino pyridine
DMF: N,N-dimethylformamide
Gln: Glutamine
Glu: Glutamic acid
Gly: Glycine
GPCRs: G protein-coupled receptors
δ: Delta
Har: Homoarginine
His: Histidine
Hlys: Homolysine
HOBt: 1-Hydroxy benzotriazole
HPLC: High performance liquid chromatography
IBD: Inflammatory bowel disease
IBS: Irritable bowel syndrome
κ: Kappa
KOR: Kappa (K) opioid receptors
μ: Mu
Leu: Leucine
Lys: Lysine
NMM: N-methyl morpholine
Orn: Ornithine
PNS: Peripheral nervous system
Ser: Serine
TFA: Trifluoroacetic acid
Thr: Threonine
TIS: Triisopropyl silane
Trt: Trityl
Tyr: Tyrosine
Val: Valine

DESCRIPTION OF THE INVENTION

Accordingly, the present invention relates to novel short-chain peptides of the general formula (I) represented below & includes their pharmaceutically acceptable salts A-B-C-D-E    (Formula I)

Wherein, 'A' and 'B' independently represents a first and second amino acids, that can independently be selected from Phe, α-Me-Phe, Tyr, Phenylglycine, Homophenylalanine, Cyclohexylglycine, Cyclohexylalanine, wherein, the aromatic ring present in any of these amino acids can be substituted with H, Halo, $NO_2$, $NH_2$, alkyl, $CF_3$ and CN.

'C' represent third amino acid that can be selected from Norleucine, Phe, Ala, Leu, α-Me-Leu, homoleucine, Val, 1-Aminocyclohexane carboxylic acid, 1-Aminocyclopentane carboxylic acid, Cyclohexylglycine;

'D' is selected from the group consisting of Arg, Lys, Har, Orn, Ala, Hlys, Norleucine, His;

'E' is selected from group consisting of:

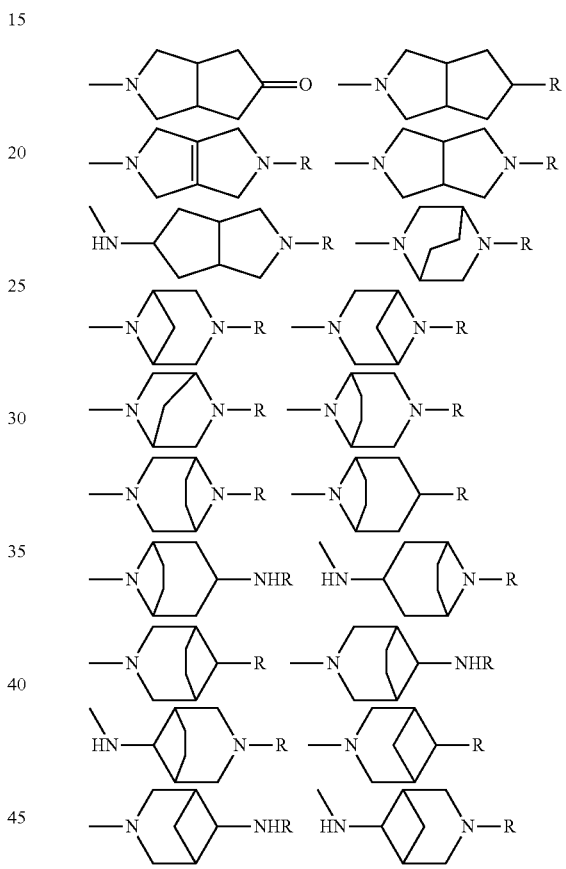

Where R at each occurrence is selected from H, —NR'R", —CN, —COOR', —CONR'R", —CO(CH$_2$)$_n$—OR', —OR', —(CH$_2$)$_n$OR', —SO$_2$R' or —SO$_2$NR'R", —(CH$_2$)$_n$COOR', —(CH$_2$)$_n$CONR'R", —(CH$_2$)$_n$NR'R", —NH(CH$_2$)—COOR', —(CH$_2$)$_n$CONHR, —CH$_2$CON[(CH$_2$)$_n$COOR']$_2$, —CH$_2$CON[(CH$_2$)$_n$OR']$_2$, —COCH$_2$N[(CH$_2$)$_n$COOR']$_2$, —CO(CH$_2$)$_n$—NR'R", —CO(CH$_2$)$_n$COOR', —CO(CH$_2$)$_n$CONR'R", —(CH$_2$)$_n$CONHNR'R", —CO(CH$_2$)$_n$CONHNR'R", —(CH$_2$)$_n$NHNR'R", —(CH$_2$)$_n$CN, —CHR$_1$COOR', —CR$_1$R$_2$COOR', -alkylaryl, aryl, C$_1$-C$_{10}$ alkyl, amidino, C$_1$-C$_6$ alkyl-substituted amidino, wherein each of R' and R" at each occurrence can be independently or both selected from H, C$_1$-C$_{10}$ alkyl, branched alkyl, alkylaryl, aryl, or R' and R" may be combined to form a 4 to 6 membered ring; n=1 to 10, wherein R$_1$ & R$_2$ in each occurrence can be independently or both selected from alkyl & halogen.

In an alternate embodiment, each of R & R' may also represent amino acids selected from the group consisting of Asp, Glu, Asn, Gln, Lys, Arg, His, Ala, Ser, Thr, Leu, Val, Gly, Har, 2-amino heptanedioic acid.

In a preferred embodiments each of 'A' and 'B' is independently selected from Phe, & Tyr; 'C' representing the third amino acid can be preferably selected from Leu, Norleucine, & 1-Aminocyclohexane carboxylic acid; 'D' which represents the fourth amino acid can be preferably selected from Lys, Arg, & Ala.

Particularly useful compounds may be selected from but not limited to the following;

TABLE 1

List of Short-chain peptides as KOR agonist

| Sr. No | Structures |
|---|---|
| 1 | 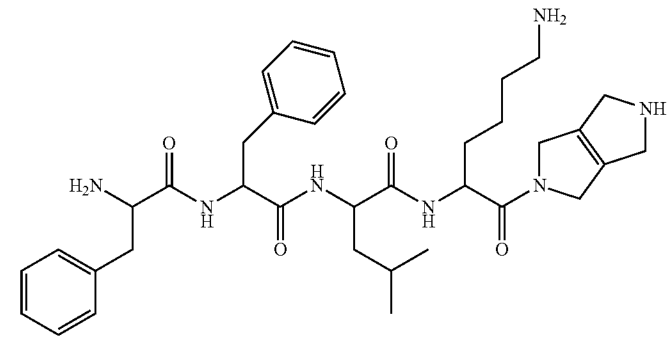 [SMILES: CC(C)CC(NC(=O)C(Cc1ccccc1)NC(=O)C(N)Cc1ccccc1)C(=O)NC(CCCCN)C(=O)N1CC2=C(CNC2)C1] |
| 2 | 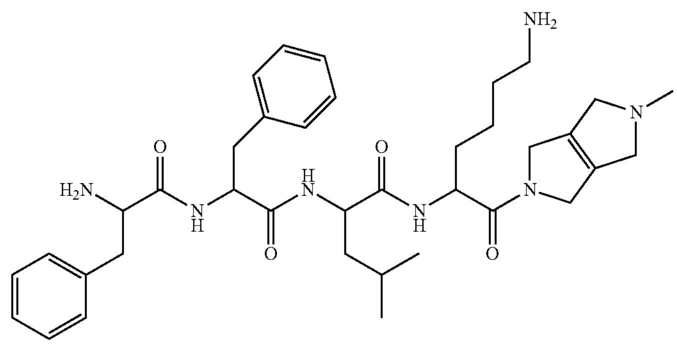 [SMILES: CC(C)CC(NC(=O)C(Cc1ccccc1)NC(=O)C(N)Cc1ccccc1)C(=O)NC(CCCCN)C(=O)N1CC2=C(CN(C)C2)C1] |
| 3 | 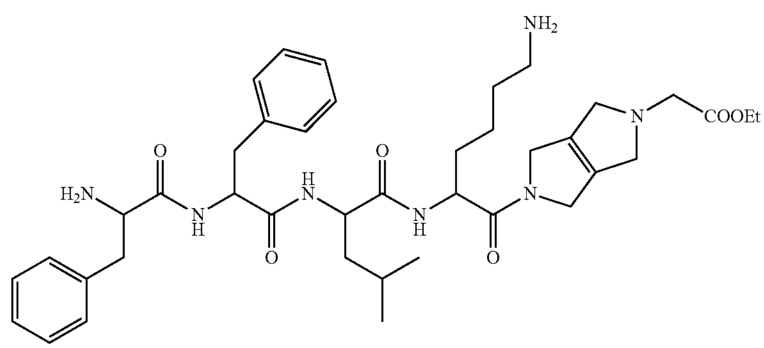 [SMILES: CCOC(=O)CN1CC2=C(C1)CN(C(=O)C(CCCCN)NC(=O)C(CC(C)C)NC(=O)C(Cc1ccccc1)NC(=O)C(N)Cc1ccccc1)C2] |
| 4 | 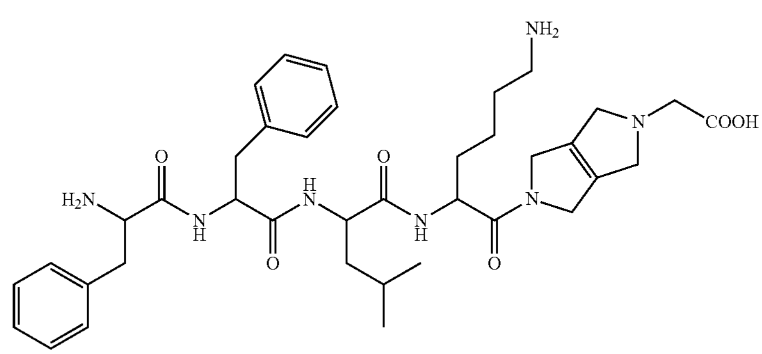 [SMILES: CC(C)CC(NC(=O)C(Cc1ccccc1)NC(=O)C(N)Cc1ccccc1)C(=O)NC(CCCCN)C(=O)N1CC2=C(CN(CC(=O)O)C2)C1] |

TABLE 1-continued

List of Short-chain peptides as KOR agonist

| Sr. No | Structures |
|---|---|
| 5 | 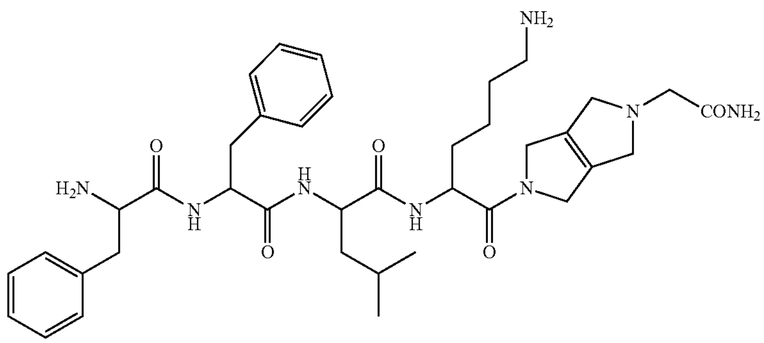 [SMILES: CC(C)CC(NC(=O)C(Cc1ccccc1)NC(=O)C(N)Cc1ccccc1)C(=O)NC(CCCCN)C(=O)N1CC2=C(CN(CC(N)=O)C2)C1] |
| 6 | 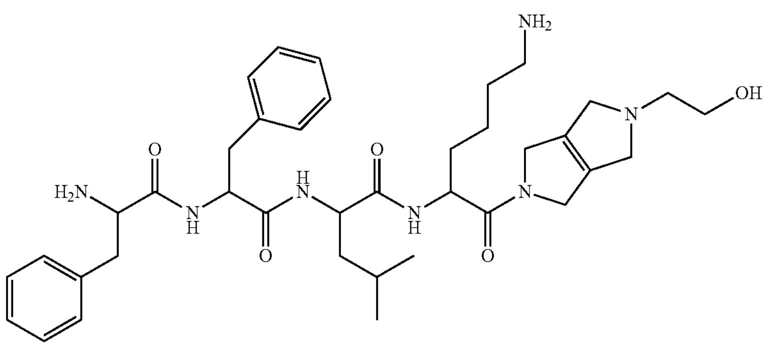 [SMILES: CC(C)CC(NC(=O)C(Cc1ccccc1)NC(=O)C(N)Cc1ccccc1)C(=O)NC(CCCCN)C(=O)N1CC2=C(CN(CCO)C2)C1] |
| 7 | 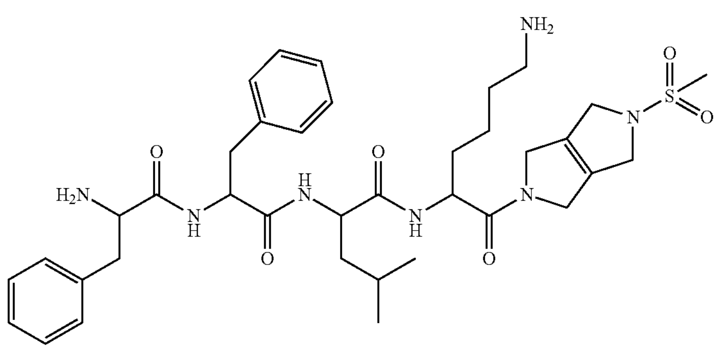 [SMILES: CC(C)CC(NC(=O)C(Cc1ccccc1)NC(=O)C(N)Cc1ccccc1)C(=O)NC(CCCCN)C(=O)N1CC2=C(C1)CN(S(C)(=O)=O)C2] |
| 8 | 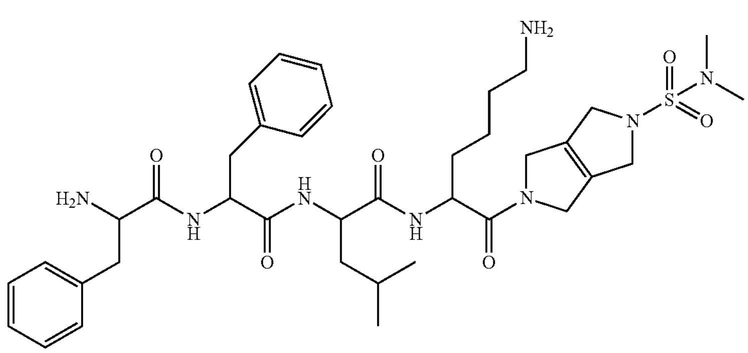 [SMILES: CC(C)CC(NC(=O)C(Cc1ccccc1)NC(=O)C(N)Cc1ccccc1)C(=O)NC(CCCCN)C(=O)N1CC2=C(C1)CN(S(=O)(=O)N(C)C)C2] |

TABLE 1-continued

List of Short-chain peptides as KOR agonist

| Sr. No | Structures |
|---|---|
| 9 | 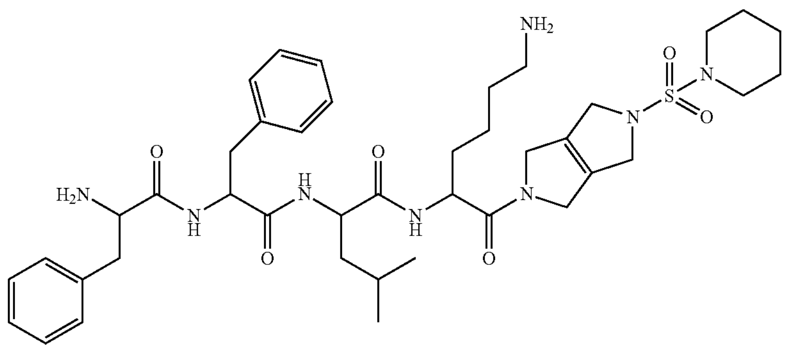 [SMILES: CC(C)CC(NC(=O)C(Cc1ccccc1)NC(=O)C(N)Cc1ccccc1)C(=O)NC(CCCCN)C(=O)N1CC2=C(C1)CN(S(=O)(=O)N1CCCCC1)C2] |
| 10 | 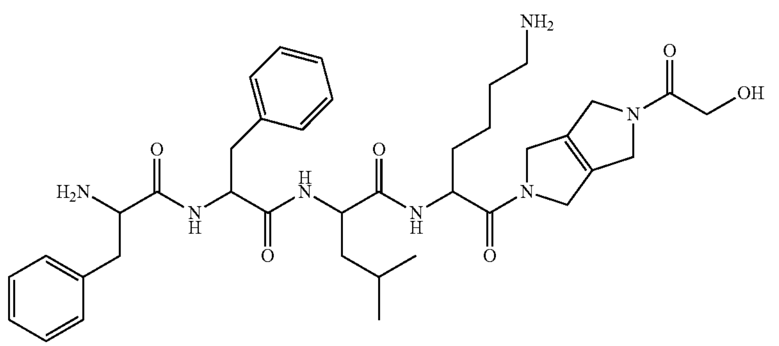 [SMILES: CC(C)CC(NC(=O)C(Cc1ccccc1)NC(=O)C(N)Cc1ccccc1)C(=O)NC(CCCCN)C(=O)N1CC2=C(CN(C(=O)CO)C2)C1] |
| 11 | 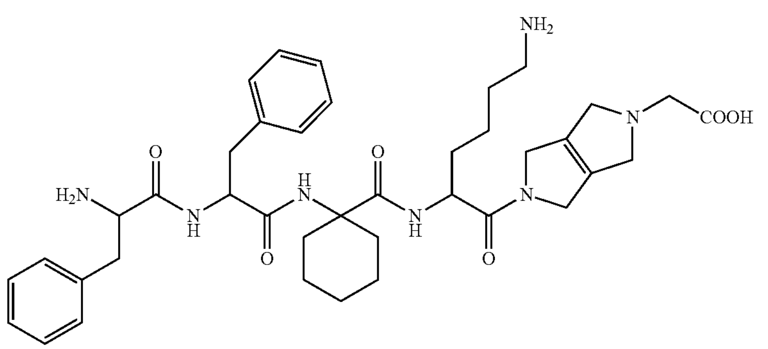 [SMILES: NCCCCC(NC(=O)C1(NC(=O)C(Cc2ccccc2)NC(=O)C(N)Cc2ccccc2)CCCCC1)C(=O)N1CC2=C(CN(CC(=O)O)C2)C1] |
| 12 | 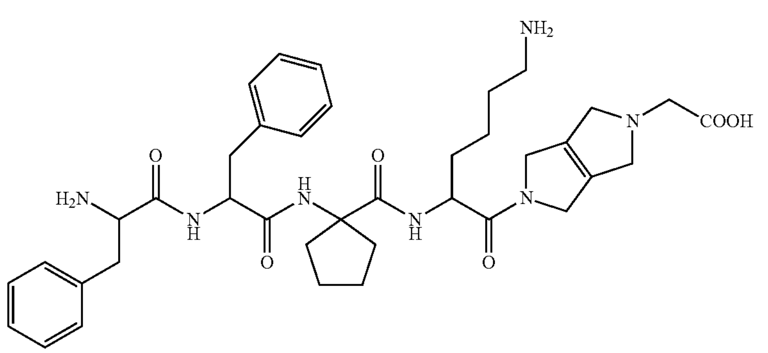 [SMILES: NCCCCC(NC(=O)C1(NC(=O)C(Cc2ccccc2)NC(=O)C(N)Cc2ccccc2)CCCC1)C(=O)N1CC2=C(CN(CC(=O)O)C2)C1] |

TABLE 1-continued
List of Short-chain peptides as KOR agonist
| Sr. No | Structures |
|---|---|
| 13 | 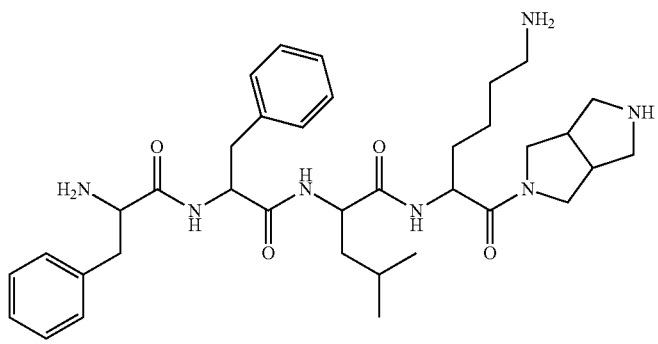 [SMILES: CC(C)CC(NC(=O)C(Cc1ccccc1)NC(=O)C(N)Cc1ccccc1)C(=O)NC(CCCCN)C(=O)N1CC2CNCC2C1] |
| 14 | 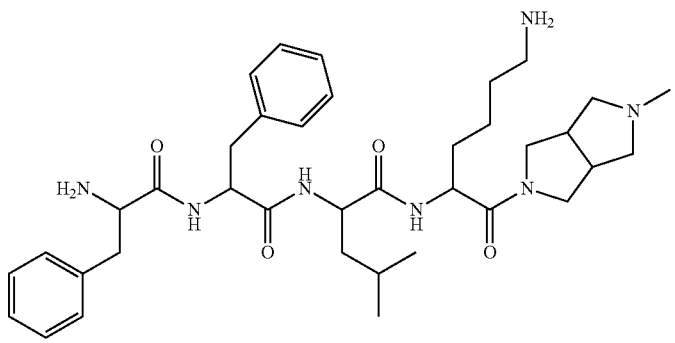 [SMILES: CC(C)CC(NC(=O)C(Cc1ccccc1)NC(=O)C(N)Cc1ccccc1)C(=O)NC(CCCCN)C(=O)N1CC2CN(C)CC2C1] |
| 15 | 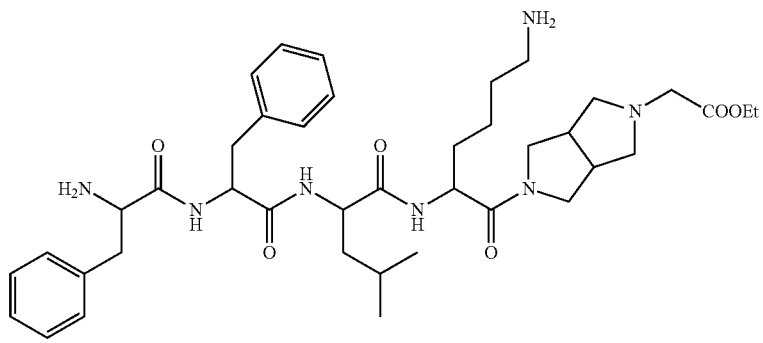 [SMILES: CCOC(=O)CN1CC2CN(C(=O)C(CCCCN)NC(=O)C(CC(C)C)NC(=O)C(Cc3ccccc3)NC(=O)C(N)Cc3ccccc3)CC2C1] |
| 16 | 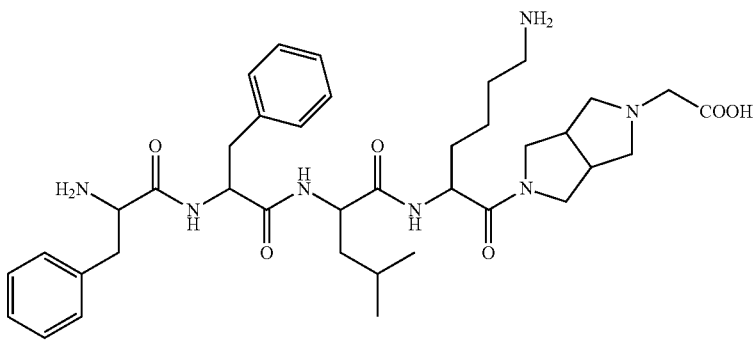 [SMILES: CC(C)CC(NC(=O)C(Cc1ccccc1)NC(=O)C(N)Cc1ccccc1)C(=O)NC(CCCCN)C(=O)N1CC2CN(CC(=O)O)CC2C1] |

TABLE 1-continued
List of Short-chain peptides as KOR agonist
| Sr. No | Structures |
|---|---|
| 17 | 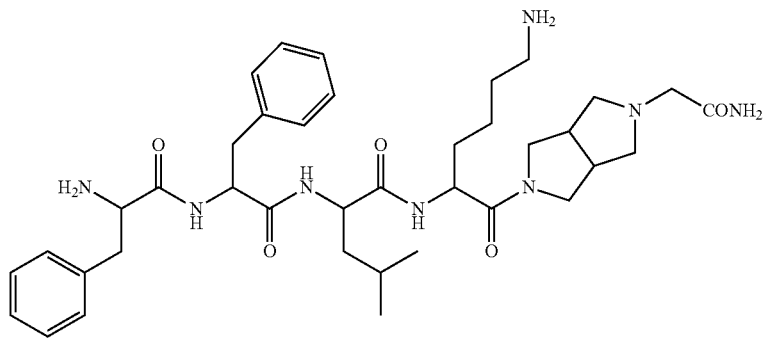 [SMILES: CC(C)CC(NC(=O)C(Cc1ccccc1)NC(=O)C(N)Cc1ccccc1)C(=O)NC(CCCCN)C(=O)N1CC2CN(CC(N)=O)CC2C1] |
| 18 | 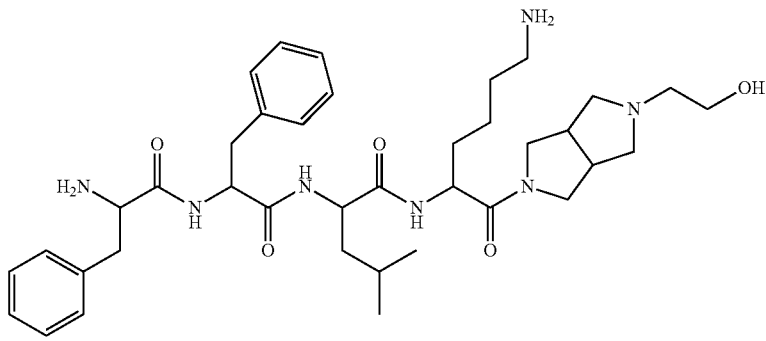 [SMILES: CC(C)CC(NC(=O)C(Cc1ccccc1)NC(=O)C(N)Cc1ccccc1)C(=O)NC(CCCCN)C(=O)N1CC2CN(CCO)CC2C1] |
| 19 | 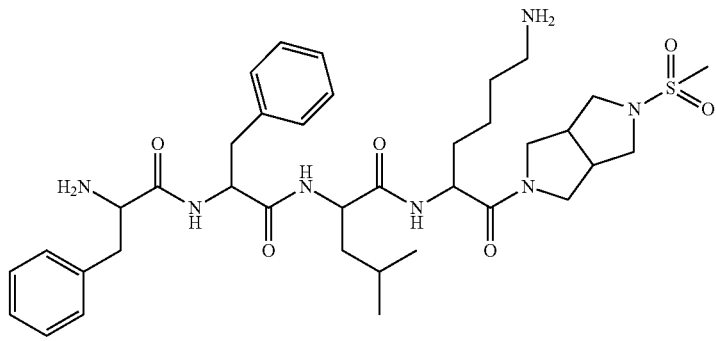 [SMILES: CC(C)CC(NC(=O)C(Cc1ccccc1)NC(=O)C(N)Cc1ccccc1)C(=O)NC(CCCCN)C(=O)N1CC2CN(S(C)(=O)=O)CC2C1] |
| 20 | 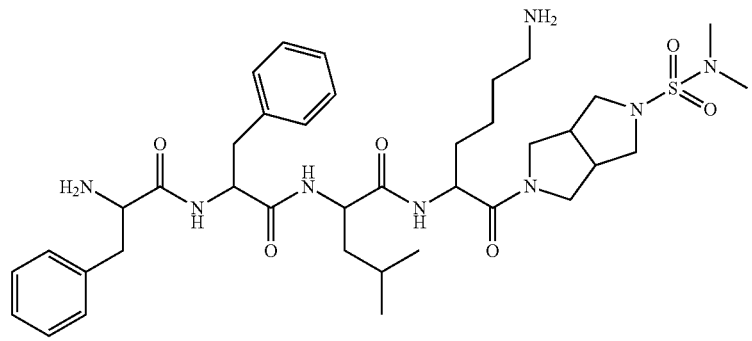 [SMILES: CC(C)CC(NC(=O)C(Cc1ccccc1)NC(=O)C(N)Cc1ccccc1)C(=O)NC(CCCCN)C(=O)N1CC2CN(S(=O)(=O)N(C)C)CC2C1] |

TABLE 1-continued
List of Short-chain peptides as KOR agonist
| Sr. No | Structures |
|---|---|
| 21 | 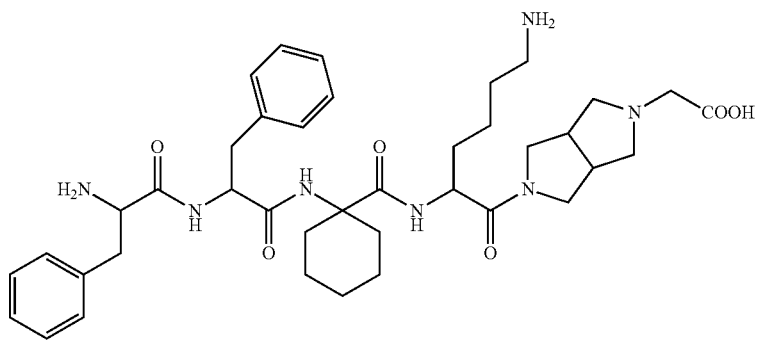 [SMILES: NCCCCC(NC(=O)C1(NC(=O)C(Cc2ccccc2)NC(=O)C(N)Cc2ccccc2)CCCCC1)C(=O)N1CC2CN(CC(=O)O)CC2C1] |
| 22 | 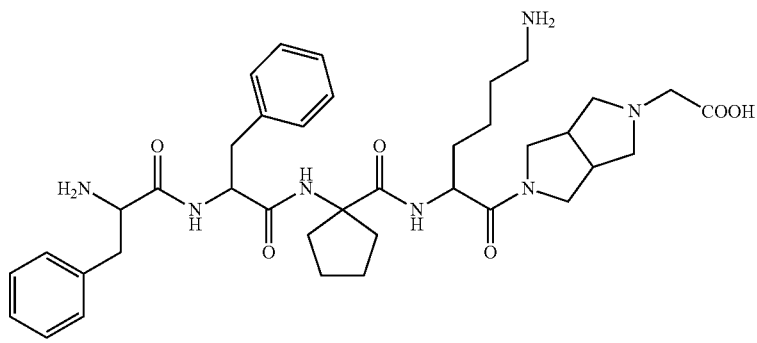 [SMILES: NCCCCC(NC(=O)C1(NC(=O)C(Cc2ccccc2)NC(=O)C(N)Cc2ccccc2)CCCC1)C(=O)N1CC2CN(CC(=O)O)CC2C1] |
| 23 | 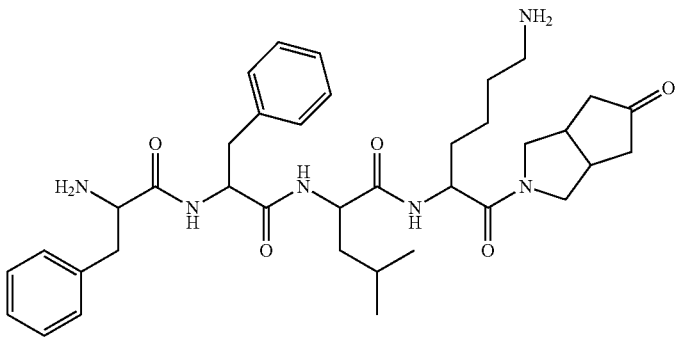 [SMILES: CC(C)CC(NC(=O)C(Cc1ccccc1)NC(=O)C(N)Cc1ccccc1)C(=O)NC(CCCCN)C(=O)N1CC2CC(=O)CC2C1] |
| 24 | 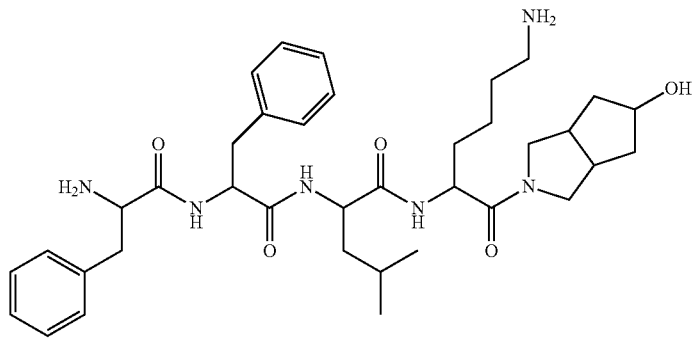 |

TABLE 1-continued
List of Short-chain peptides as KOR agonist
| Sr. No | Structures |
|---|---|
| 25 | 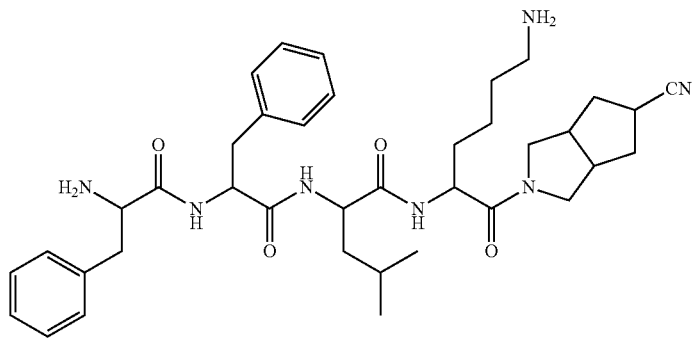 [SMILES: CC(C)CC(NC(=O)C(Cc1ccccc1)NC(=O)C(N)Cc1ccccc1)C(=O)NC(CCCCN)C(=O)N1CC2CC(O)CC2C1] |
| 26 | 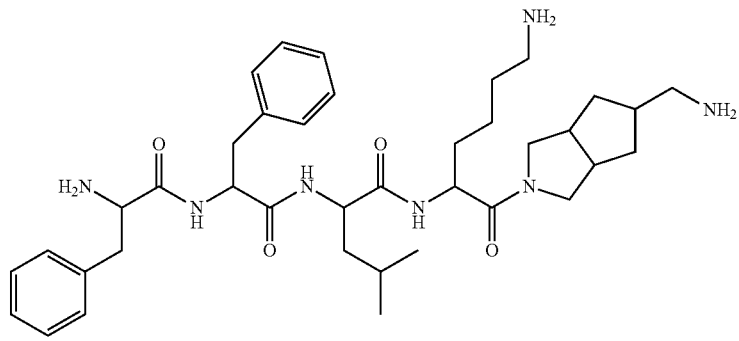 [SMILES: CC(C)CC(NC(=O)C(Cc1ccccc1)NC(=O)C(N)Cc1ccccc1)C(=O)NC(CCCCN)C(=O)N1CC2CC(CN)CC2C1] |
| 27 | 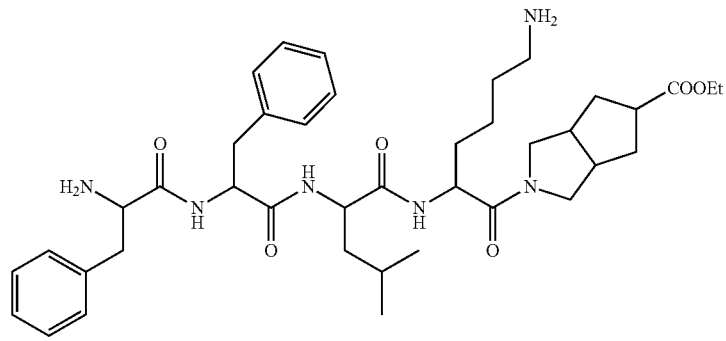 [SMILES: CCOC(=O)C1CC2CN(C(=O)C(CCCCN)NC(=O)C(CC(C)C)NC(=O)C(Cc3ccccc3)NC(=O)C(N)Cc3ccccc3)CC2C1] |
| 28 | 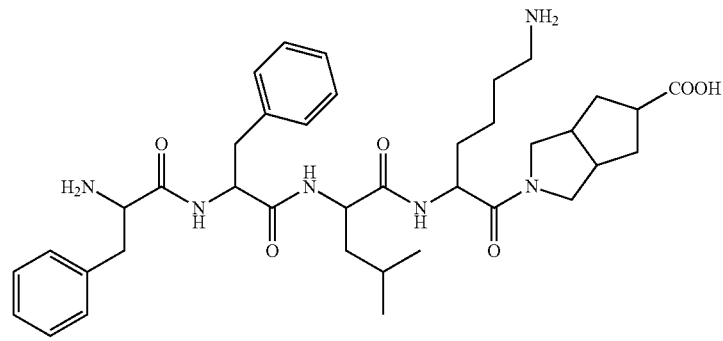 [SMILES: CC(C)CC(NC(=O)C(Cc1ccccc1)NC(=O)C(N)Cc1ccccc1)C(=O)NC(CCCCN)C(=O)N1CC2CC(C(=O)O)CC2C1] |

TABLE 1-continued

List of Short-chain peptides as KOR agonist

| Sr. No | Structures |
|---|---|
| 29 | 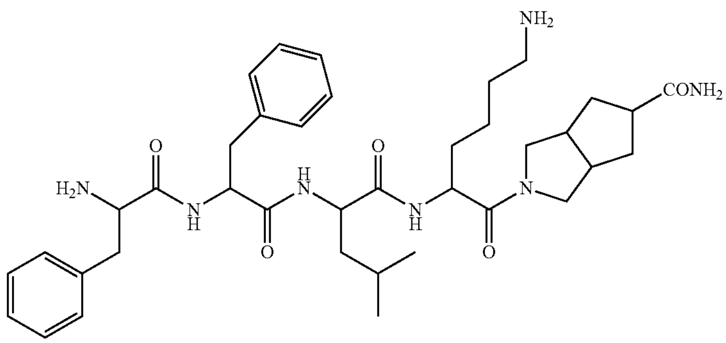 [SMILES: CC(C)CC(NC(=O)C(Cc1ccccc1)NC(=O)C(N)Cc1ccccc1)C(=O)NC(CCCCN)C(=O)N1CC2CC(C(N)=O)CC2C1] |
| 30 | 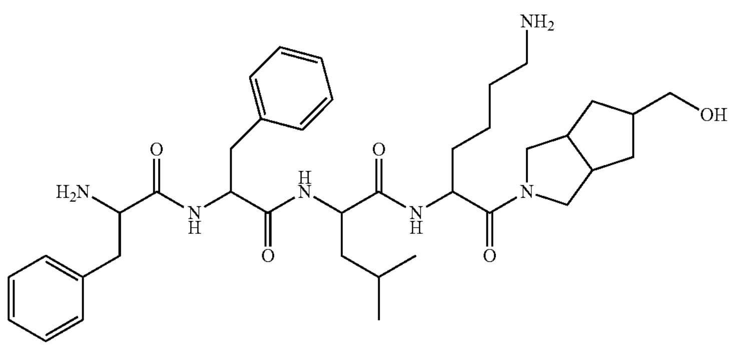 [SMILES: CC(C)CC(NC(=O)C(Cc1ccccc1)NC(=O)C(N)Cc1ccccc1)C(=O)NC(CCCCN)C(=O)N1CC2CC(CO)CC2C1] |
| 31 | 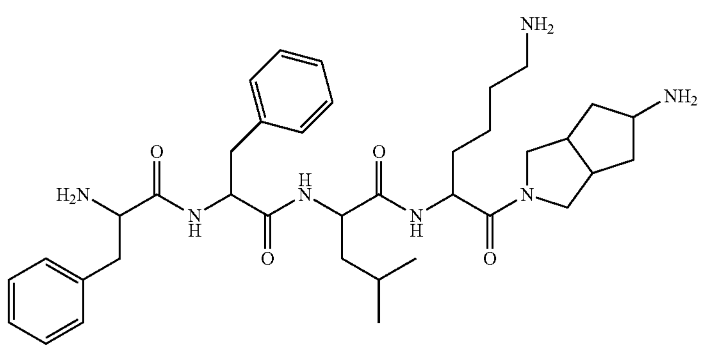 [SMILES: CC(C)CC(NC(=O)C(Cc1ccccc1)NC(=O)C(N)Cc1ccccc1)C(=O)NC(CCCCN)C(=O)N1CC2CC(N)CC2C1] |
| 32 | 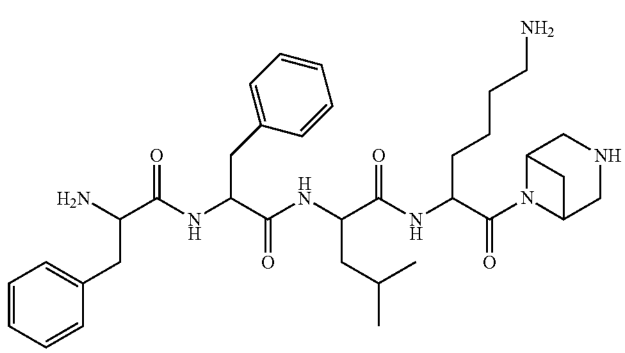 [SMILES: CC(C)CC(NC(=O)C(Cc1ccccc1)NC(=O)C(N)Cc1ccccc1)C(=O)NC(CCCCN)C(=O)N1C2CNCC1C2] |

TABLE 1-continued

List of Short-chain peptides as KOR agonist

| Sr. No | Structures |
|---|---|
| 33 | 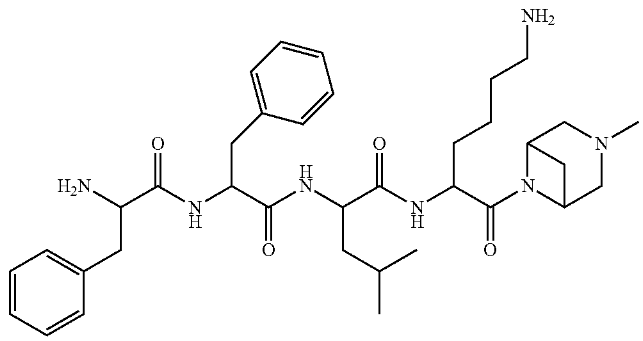 [SMILES: CC(C)CC(NC(=O)C(Cc1ccccc1)NC(=O)C(N)Cc1ccccc1)C(=O)NC(CCCCN)C(=O)N1C2CC1CN(C)C2] |
| 34 | 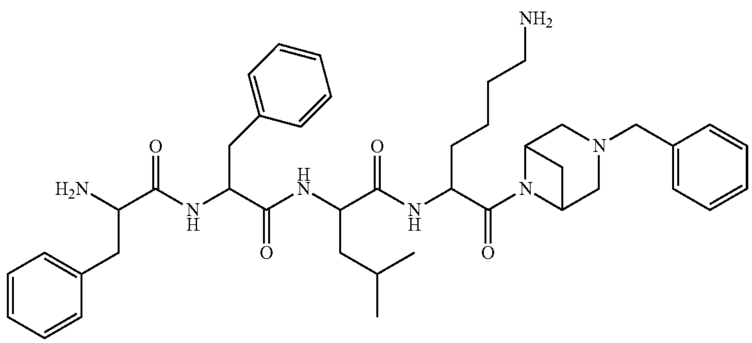 [SMILES: CC(C)CC(NC(=O)C(Cc1ccccc1)NC(=O)C(N)Cc1ccccc1)C(=O)NC(CCCCN)C(=O)N1C2CC1CN(Cc1ccccc1)C2] |
| 35 | 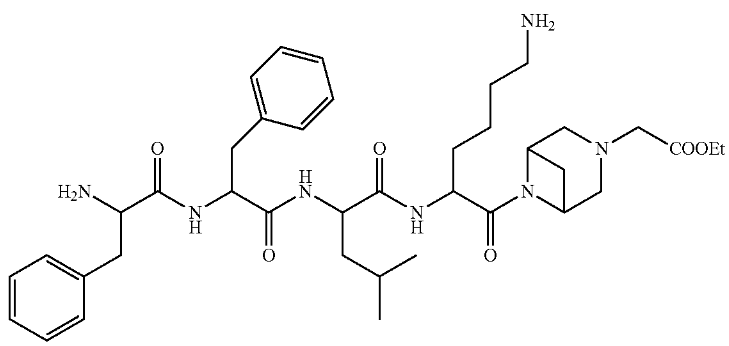 [SMILES: CCOC(=O)CN1CC2CC(C1)N2C(=O)C(CCCCN)NC(=O)C(CC(C)C)NC(=O)C(Cc1ccccc1)NC(=O)C(N)Cc1ccccc1] |
| 36 | 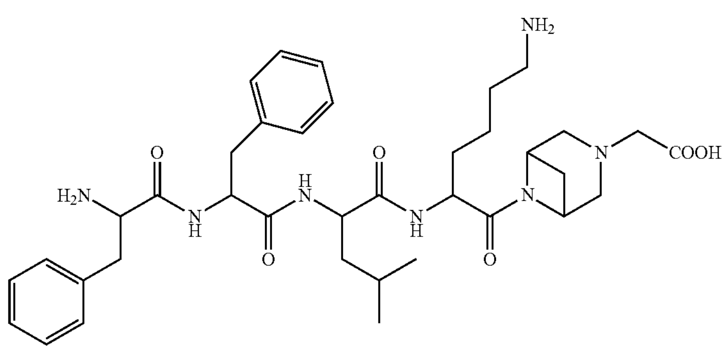 [SMILES: CC(C)CC(NC(=O)C(Cc1ccccc1)NC(=O)C(N)Cc1ccccc1)C(=O)NC(CCCCN)C(=O)N1C2CC1CN(CC(=O)O)C2] |

TABLE 1-continued
List of Short-chain peptides as KOR agonist
| Sr. No | Structures |
|---|---|
| 37 | 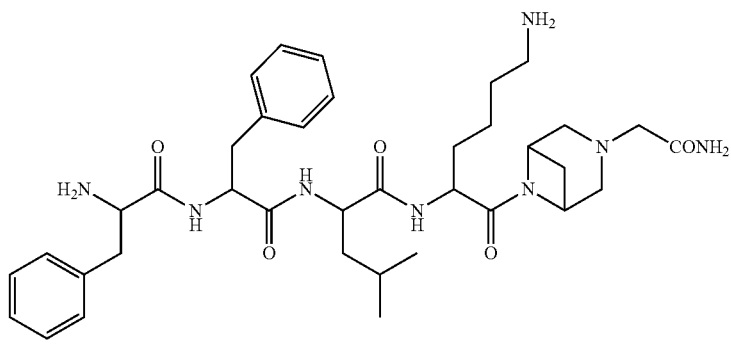 [SMILES: CC(C)CC(NC(=O)C(Cc1ccccc1)NC(=O)C(N)Cc1ccccc1)C(=O)NC(CCCCN)C(=O)N1C2CC1CN(CC(N)=O)C2] |
| 38 | 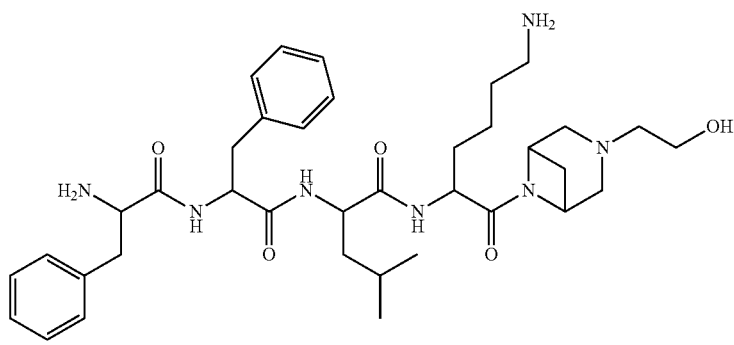 [SMILES: CC(C)CC(NC(=O)C(Cc1ccccc1)NC(=O)C(N)Cc1ccccc1)C(=O)NC(CCCCN)C(=O)N1C2CC1CN(CCO)C2] |
| 39 | 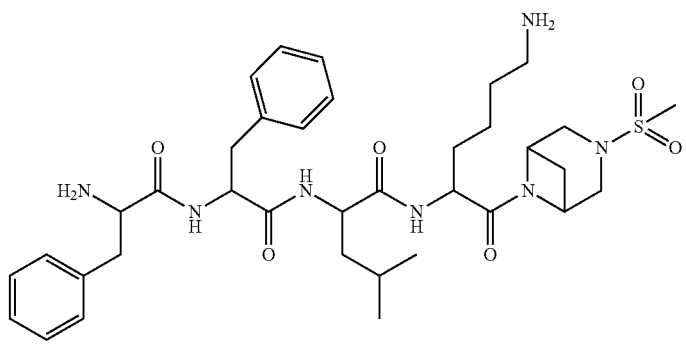 [SMILES: CC(C)CC(NC(=O)C(Cc1ccccc1)NC(=O)C(N)Cc1ccccc1)C(=O)NC(CCCCN)C(=O)N1C2CC1CN(S(C)(=O)=O)C2] |
| 40 | 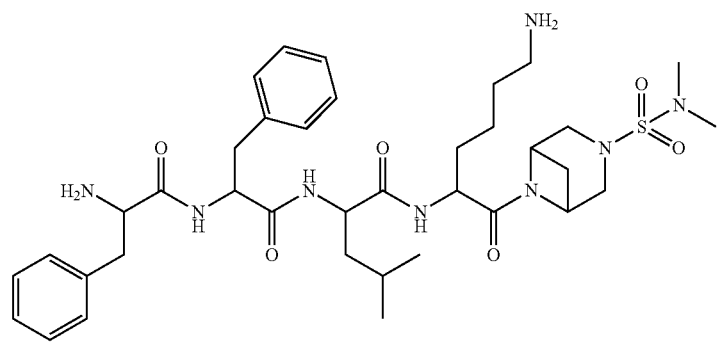 [SMILES: CC(C)CC(NC(=O)C(Cc1ccccc1)NC(=O)C(N)Cc1ccccc1)C(=O)NC(CCCCN)C(=O)N1C2CC1CN(S(=O)(=O)N(C)C)C2] |

TABLE 1-continued
List of Short-chain peptides as KOR agonist
| Sr. No | Structures |
|---|---|
| 41 | 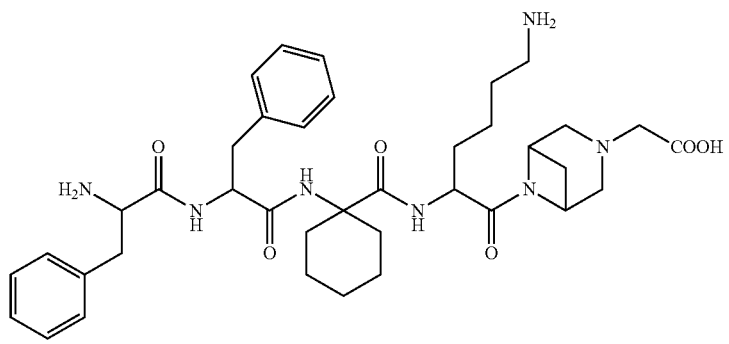 [SMILES: NCCCCC(NC(=O)C1(NC(=O)C(Cc2ccccc2)NC(=O)C(N)Cc2ccccc2)CCCCC1)C(=O)N1C2CC1CN(CC(=O)O)C2] |
| 42 | 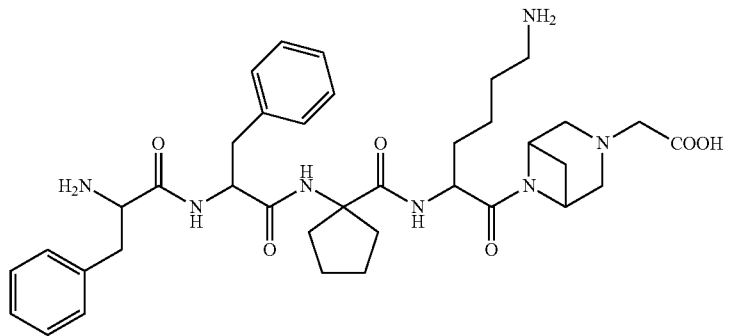 [SMILES: NCCCCC(NC(=O)C1(NC(=O)C(Cc2ccccc2)NC(=O)C(N)Cc2ccccc2)CCCC1)C(=O)N1C2CC1CN(CC(=O)O)C2] |
| 43 | 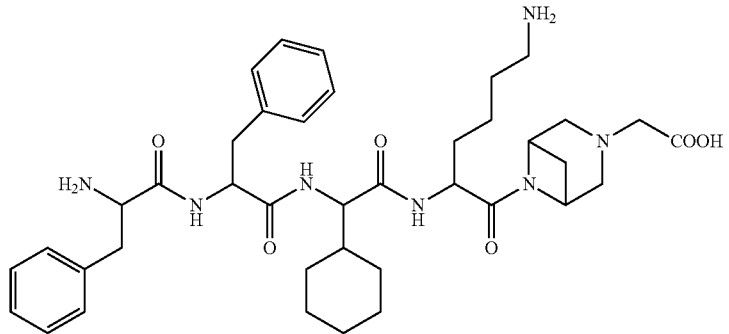 [SMILES: NCCCCC(NC(=O)C(NC(=O)C(Cc1ccccc1)NC(=O)C(N)Cc1ccccc1)C1CCCCC1)C(=O)N1C2CC1CN(CC(=O)O)C2] |
| 44 | 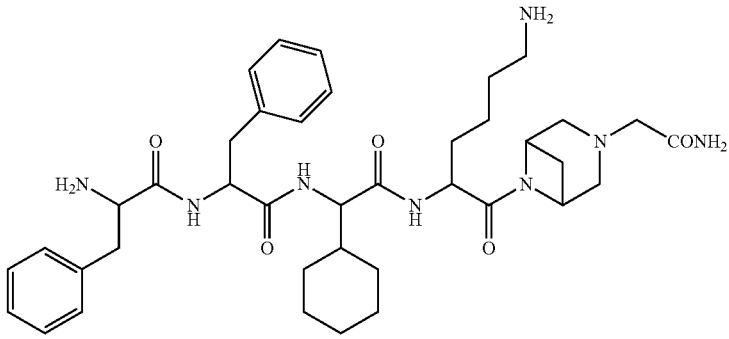 [SMILES: NCCCCC(NC(=O)C(NC(=O)C(Cc1ccccc1)NC(=O)C(N)Cc1ccccc1)C1CCCCC1)C(=O)N1C2CC1CN(CC(N)=O)C2] |

TABLE 1-continued
List of Short-chain peptides as KOR agonist
| Sr. No | Structures |
|---|---|
| 45 | 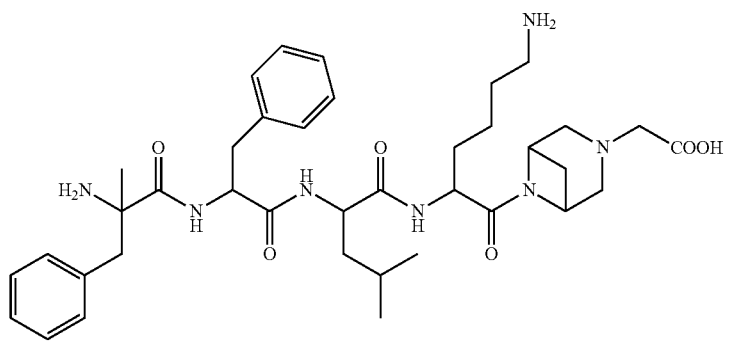 [SMILES: CC(C)CC(NC(=O)C(Cc1ccccc1)NC(=O)C(C)(N)Cc1ccccc1)C(=O)NC(CCCCN)C(=O)N1C2CC1CN(CC(=O)O)C2] |
| 46 | 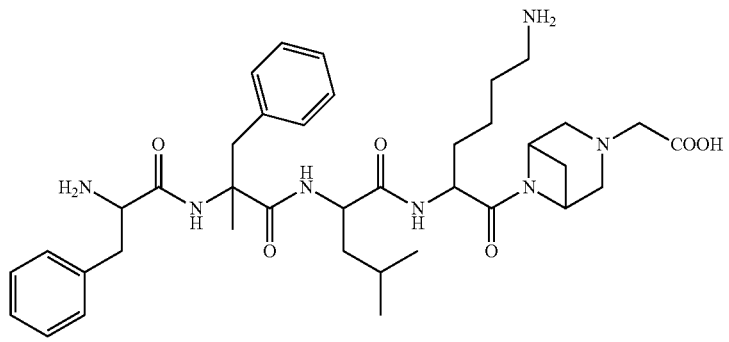 [SMILES: CC(C)CC(NC(=O)C(C)(Cc1ccccc1)NC(=O)C(N)Cc1ccccc1)C(=O)NC(CCCCN)C(=O)N1C2CC1CN(CC(=O)O)C2] |
| 47 | 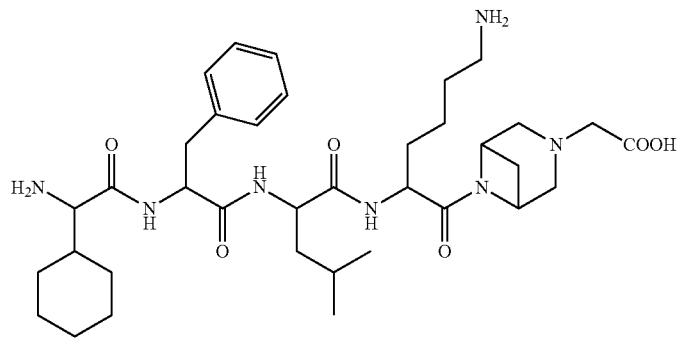 [SMILES: CC(C)CC(NC(=O)C(Cc1ccccc1)NC(=O)C(N)C1CCCCC1)C(=O)NC(CCCCN)C(=O)N1C2CC1CN(CC(=O)O)C2] |
| 48 | 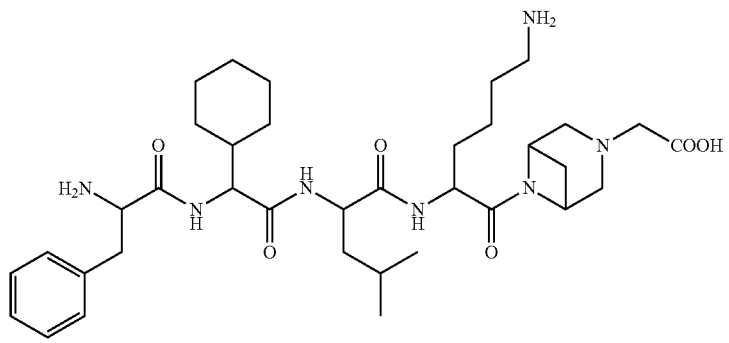 [SMILES: CC(C)CC(NC(=O)C(NC(=O)C(N)Cc1ccccc1)C1CCCCC1)C(=O)NC(CCCCN)C(=O)N1C2CC1CN(CC(=O)O)C2] |

TABLE 1-continued
List of Short-chain peptides as KOR agonist
| Sr. No | Structures |
|---|---|
| 49 | 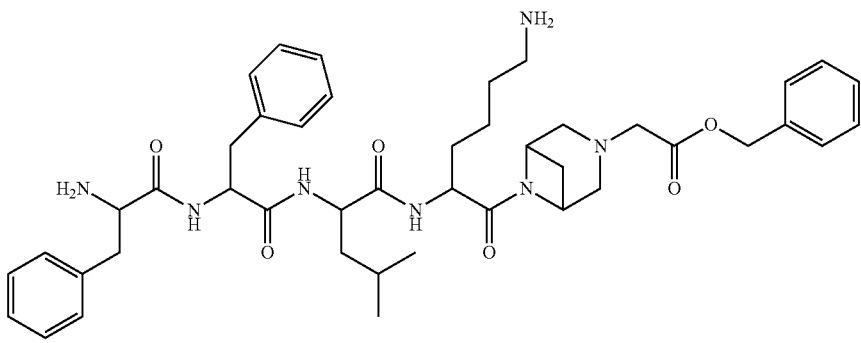 [SMILES: CC(C)CC(NC(=O)C(Cc1ccccc1)NC(=O)C(N)Cc1ccccc1)C(=O)NC(CCCCN)C(=O)N1C2CC1CN(CC(=O)OCc1ccccc1)C2] |
| 50 | 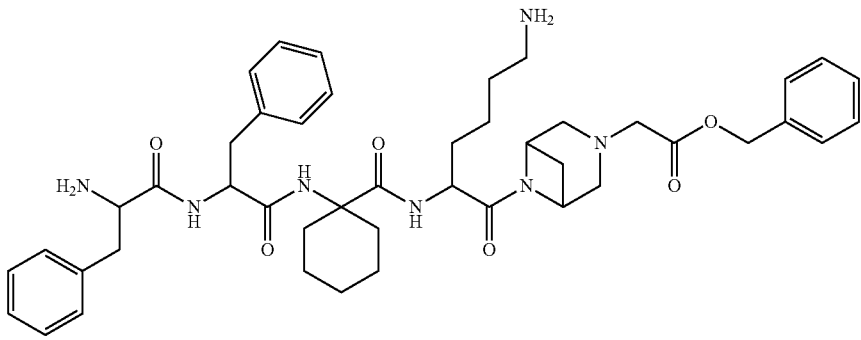 [SMILES: NCCCCC(NC(=O)C1(NC(=O)C(Cc2ccccc2)NC(=O)C(N)Cc2ccccc2)CCCCC1)C(=O)N1C2CC1CN(CC(=O)OCc1ccccc1)C2] |
| 51 | 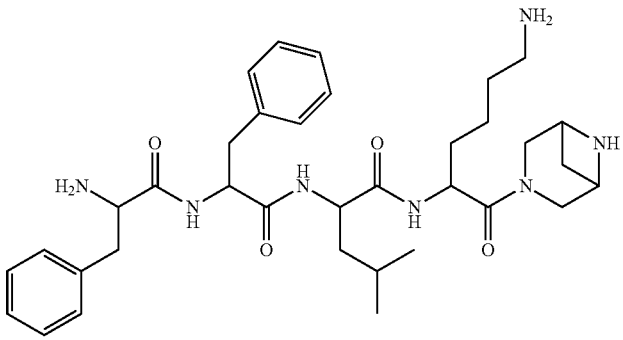 [SMILES: CC(C)CC(NC(=O)C(Cc1ccccc1)NC(=O)C(N)Cc1ccccc1)C(=O)NC(CCCCN)C(=O)N1CC2CC(C1)N2] |
| 52 | 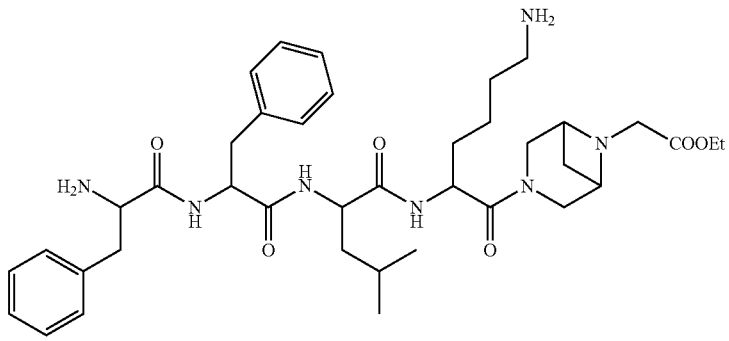 [SMILES: CCOC(=O)CN1C2CC1CN(C(=O)C(CCCCN)NC(=O)C(CC(C)C)NC(=O)C(Cc1ccccc1)NC(=O)C(N)Cc1ccccc1)C2] |

TABLE 1-continued
List of Short-chain peptides as KOR agonist
| Sr. No | Structures |
|---|---|
| 53 | 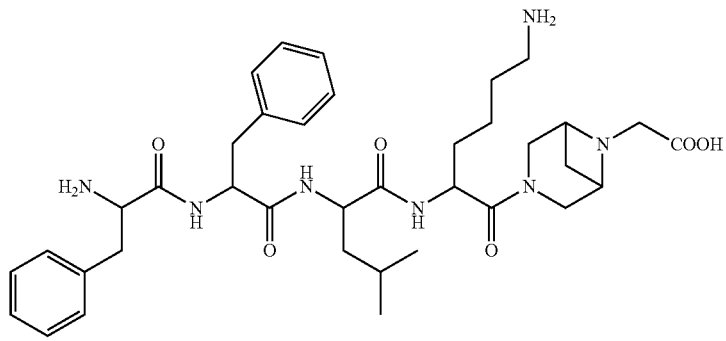 |
| 54 | 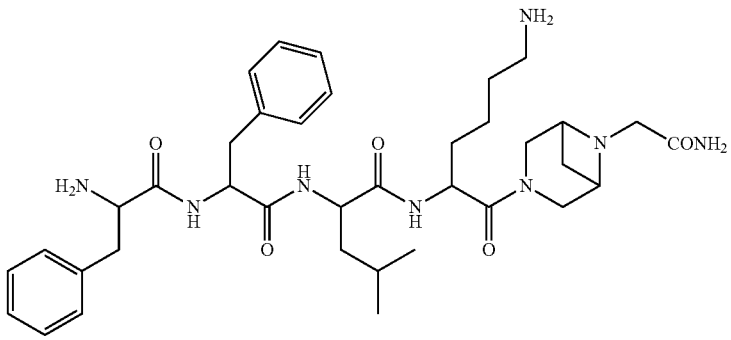 [SMILES: CC(C)CC(NC(=O)C(Cc1ccccc1)NC(=O)C(N)Cc1ccccc1)C(=O)NC(CCCCN)C(=O)N1CC2CC(C1)N2CC(N)=O] |
| 55 | 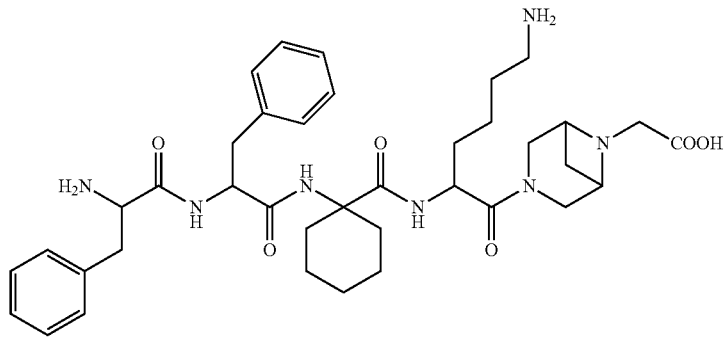 [SMILES: NCCCCC(NC(=O)C1(NC(=O)C(Cc2ccccc2)NC(=O)C(N)Cc2ccccc2)CCCCC1)C(=O)N1CC2CC(C1)N2CC(=O)O] |
| 56 | 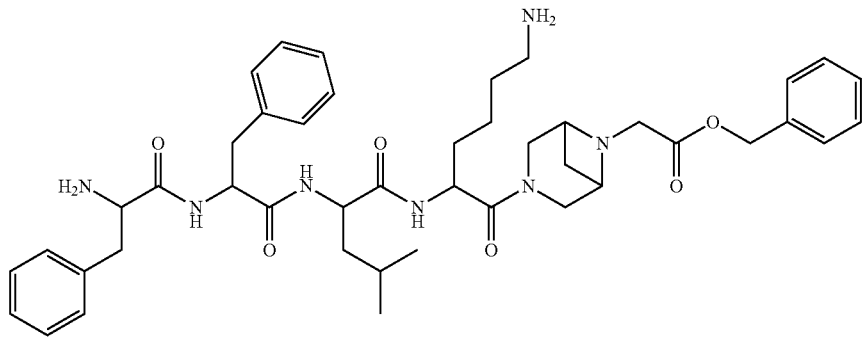 [SMILES: CC(C)CC(NC(=O)C(Cc1ccccc1)NC(=O)C(N)Cc1ccccc1)C(=O)NC(CCCCN)C(=O)N1CC2CC(C1)N2CC(=O)OCc1ccccc1] |

TABLE 1-continued

List of Short-chain peptides as KOR agonist

| Sr. No | Structures |
|---|---|
| 57 | 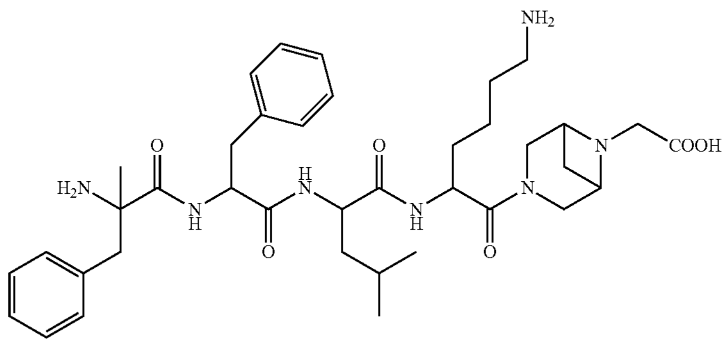 [SMILES: CC(C)CC(NC(=O)C(Cc1ccccc1)NC(=O)C(C)(N)Cc1ccccc1)C(=O)NC(CCCCN)C(=O)N1CC2CC(C1)N2CC(=O)O] |
| 58 | 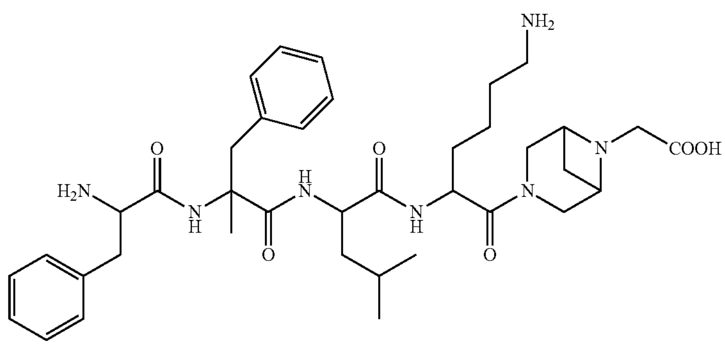 [SMILES: CC(C)CC(NC(=O)C(C)(Cc1ccccc1)NC(=O)C(N)Cc1ccccc1)C(=O)NC(CCCCN)C(=O)N1CC2CC(C1)N2CC(=O)O] |
| 59 | 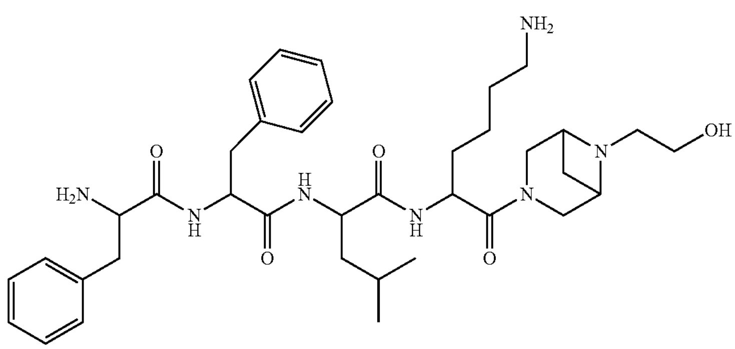 [SMILES: CC(C)CC(NC(=O)C(Cc1ccccc1)NC(=O)C(N)Cc1ccccc1)C(=O)NC(CCCCN)C(=O)N1CC2CC(C1)N2CCO] |
| 60 | 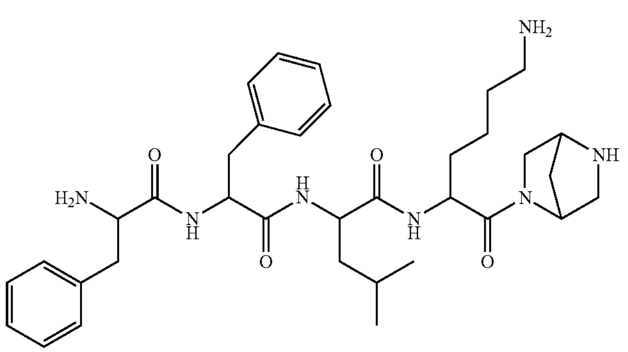 [SMILES: CC(C)CC(NC(=O)C(Cc1ccccc1)NC(=O)C(N)Cc1ccccc1)C(=O)NC(CCCCN)C(=O)N1CC2CC1CN2] |

TABLE 1-continued
List of Short-chain peptides as KOR agonist
| Sr. No | Structures |
|---|---|
| 61 | 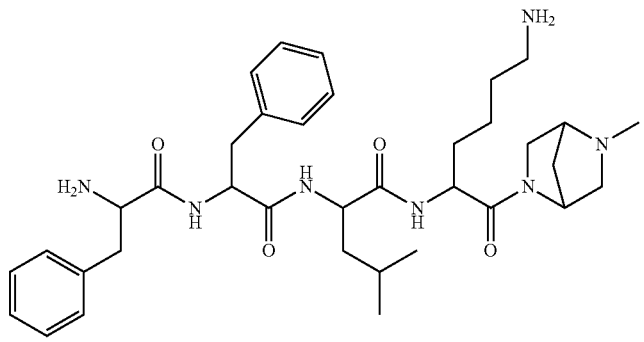 [SMILES: CC(C)CC(NC(=O)C(Cc1ccccc1)NC(=O)C(N)Cc1ccccc1)C(=O)NC(CCCCN)C(=O)N1CC2CC1CN2C] |
| 62 | 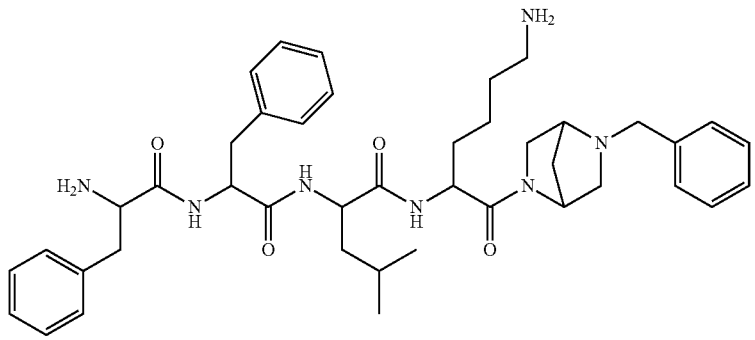 [SMILES: CC(C)CC(NC(=O)C(Cc1ccccc1)NC(=O)C(N)Cc1ccccc1)C(=O)NC(CCCCN)C(=O)N1CC2CC1CN2Cc1ccccc1] |
| 63 | 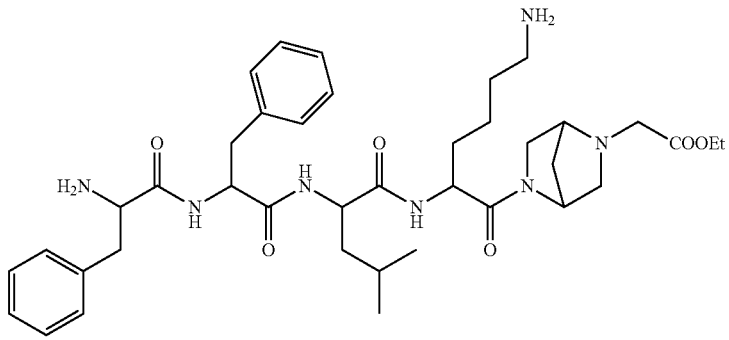 [SMILES: CCOC(=O)CN1CC2CC1CN2C(=O)C(CCCCN)NC(=O)C(CC(C)C)NC(=O)C(Cc1ccccc1)NC(=O)C(N)Cc1ccccc1] |
| 64 | 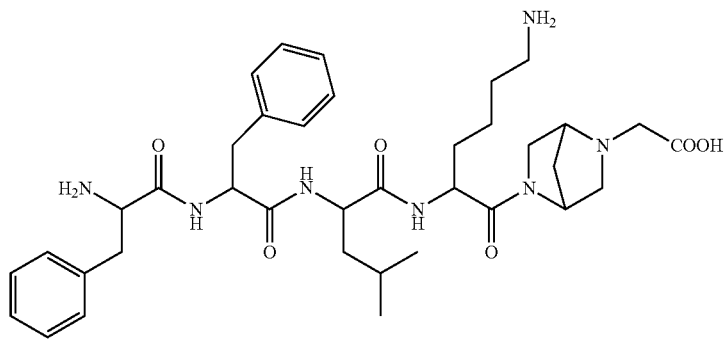 [SMILES: CC(C)CC(NC(=O)C(Cc1ccccc1)NC(=O)C(N)Cc1ccccc1)C(=O)NC(CCCCN)C(=O)N1CC2CC1CN2CC(=O)O] |

TABLE 1-continued

List of Short-chain peptides as KOR agonist

| Sr. No | Structures |
|---|---|
| 65 | 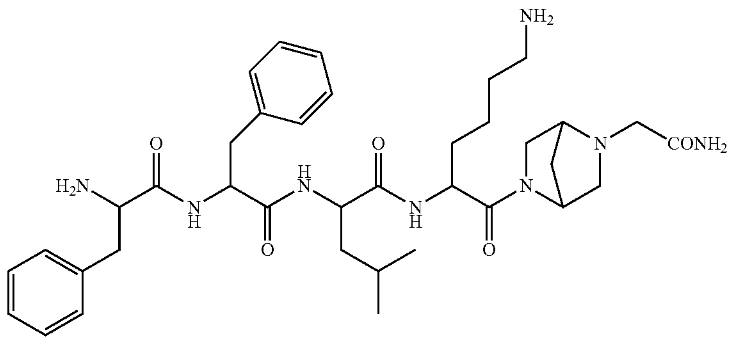 [SMILES: CC(C)CC(NC(=O)C(Cc1ccccc1)NC(=O)C(N)Cc1ccccc1)C(=O)NC(CCCCN)C(=O)N1CC2CC1CN2CC(N)=O] |
| 66 | 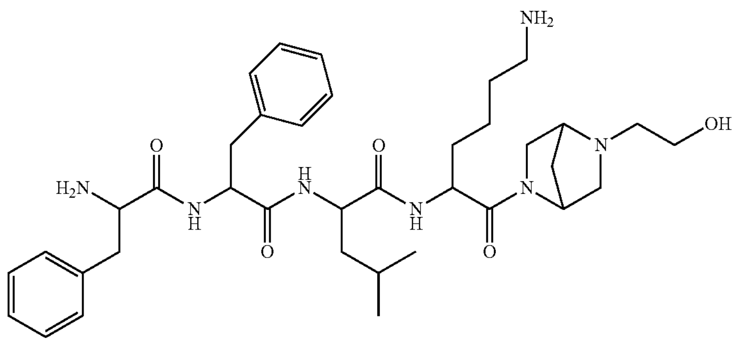 [SMILES: CC(C)CC(NC(=O)C(Cc1ccccc1)NC(=O)C(N)Cc1ccccc1)C(=O)NC(CCCCN)C(=O)N1CC2CC1CN2CCO] |
| 67 | 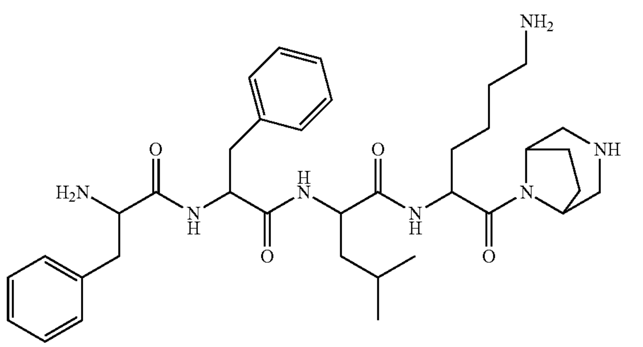 [SMILES: CC(C)CC(NC(=O)C(Cc1ccccc1)NC(=O)C(N)Cc1ccccc1)C(=O)NC(CCCCN)C(=O)N1C2CCC1CNC2] |
| 68 | 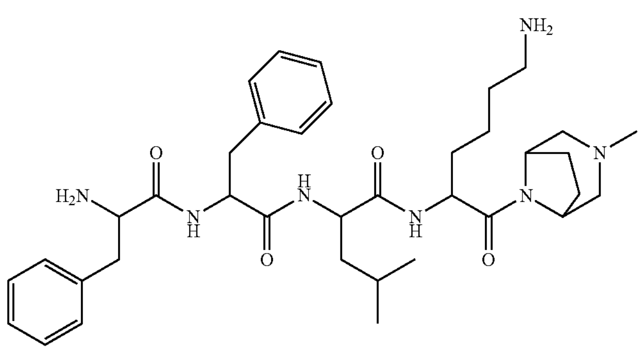 [SMILES: CC(C)CC(NC(=O)C(Cc1ccccc1)NC(=O)C(N)Cc1ccccc1)C(=O)NC(CCCCN)C(=O)N1C2CCC1CN(C)C2] |

TABLE 1-continued

List of Short-chain peptides as KOR agonist

| Sr. No | Structures |
|---|---|
| 69 | 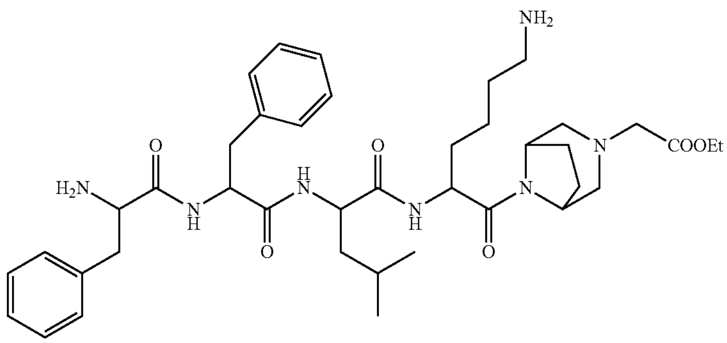 [SMILES: CCOC(=O)CN1CC2CCC(C1)N2C(=O)C(CCCCN)NC(=O)C(CC(C)C)NC(=O)C(Cc1ccccc1)NC(=O)C(N)Cc1ccccc1] |
| 70 | 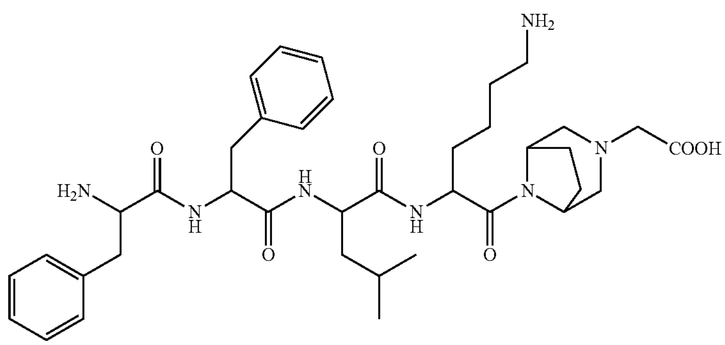 [SMILES: CC(C)CC(NC(=O)C(Cc1ccccc1)NC(=O)C(N)Cc1ccccc1)C(=O)NC(CCCCN)C(=O)N1C2CCC1CN(CC(=O)O)C2] |
| 71 | 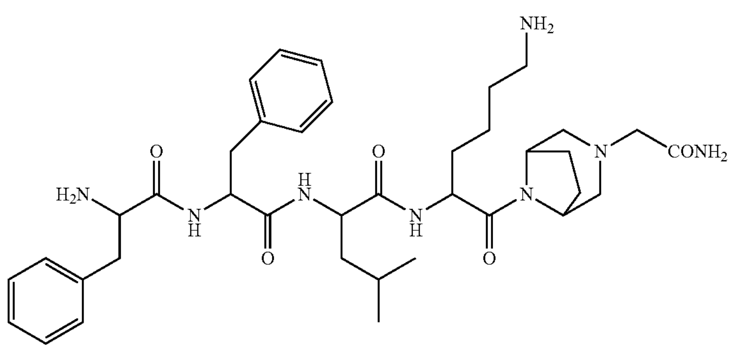 [SMILES: CC(C)CC(NC(=O)C(Cc1ccccc1)NC(=O)C(N)Cc1ccccc1)C(=O)NC(CCCCN)C(=O)N1C2CCC1CN(CC(N)=O)C2] |
| 72 | 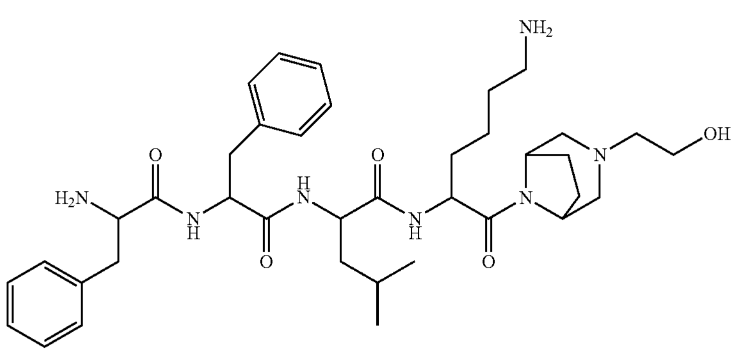 [SMILES: CC(C)CC(NC(=O)C(Cc1ccccc1)NC(=O)C(N)Cc1ccccc1)C(=O)NC(CCCCN)C(=O)N1C2CCC1CN(CCO)C2] |

TABLE 1-continued
List of Short-chain peptides as KOR agonist
| Sr. No | Structures |
|---|---|
| 73 | 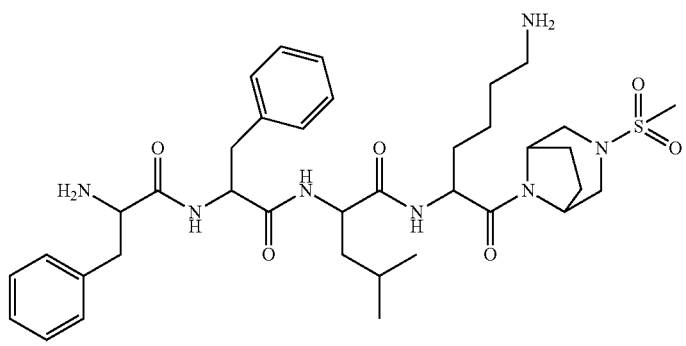 [SMILES: CC(C)CC(NC(=O)C(Cc1ccccc1)NC(=O)C(N)Cc1ccccc1)C(=O)NC(CCCCN)C(=O)N1C2CCC1CN(S(C)(=O)=O)C2] |
| 74 | 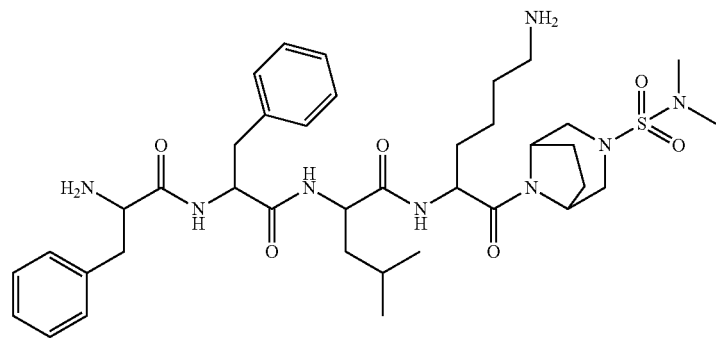 [SMILES: CC(C)CC(NC(=O)C(Cc1ccccc1)NC(=O)C(N)Cc1ccccc1)C(=O)NC(CCCCN)C(=O)N1C2CCC1CN(S(=O)(=O)N(C)C)C2] |
| 75 | 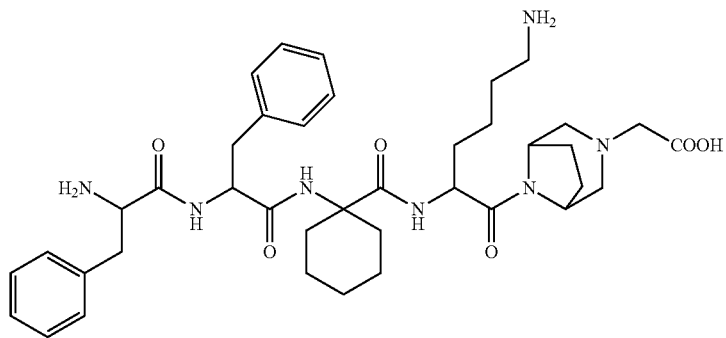 [SMILES: NCCCCC(NC(=O)C1(NC(=O)C(Cc2ccccc2)NC(=O)C(N)Cc2ccccc2)CCCCC1)C(=O)N1C2CCC1CN(CC(=O)O)C2] |
| 76 | 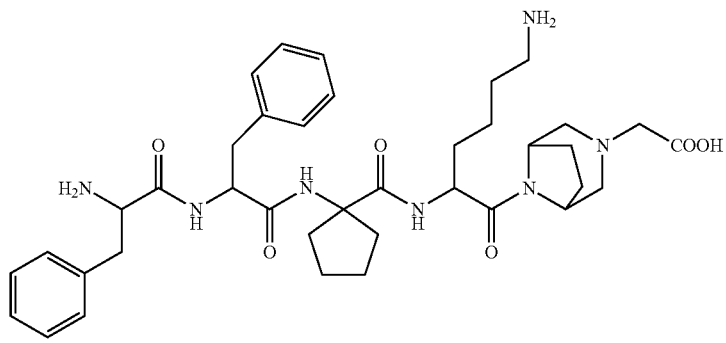 [SMILES: NCCCCC(NC(=O)C1(NC(=O)C(Cc2ccccc2)NC(=O)C(N)Cc2ccccc2)CCCC1)C(=O)N1C2CCC1CN(CC(=O)O)C2] |

TABLE 1-continued
List of Short-chain peptides as KOR agonist
| Sr. No | Structures |
|---|---|
| 77 | 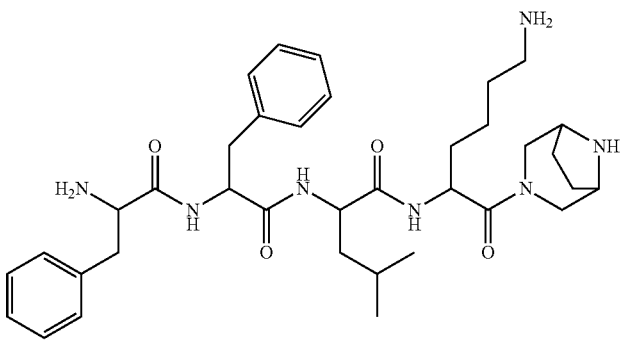 [SMILES: CC(C)CC(NC(=O)C(Cc1ccccc1)NC(=O)C(N)Cc1ccccc1)C(=O)NC(CCCCN)C(=O)N1CC2CCC(C1)N2] |
| 78 | 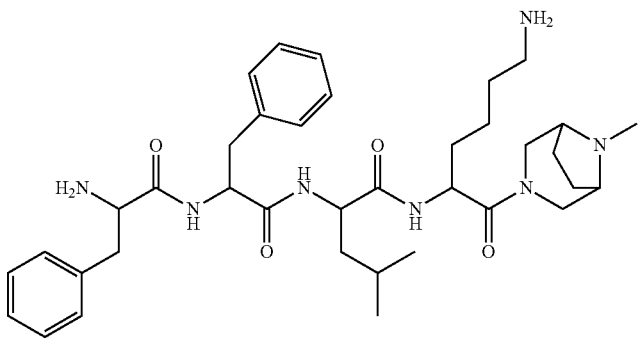 [SMILES: CC(C)CC(NC(=O)C(Cc1ccccc1)NC(=O)C(N)Cc1ccccc1)C(=O)NC(CCCCN)C(=O)N1CC2CCC(C1)N2C] |
| 79 | 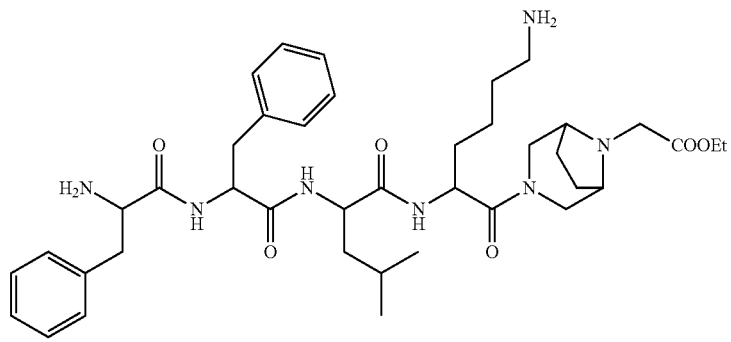 [SMILES: CCOC(=O)CN1C2CCC1CN(C(=O)C(CCCCN)NC(=O)C(CC(C)C)NC(=O)C(Cc1ccccc1)NC(=O)C(N)Cc1ccccc1)C2] |
| 80 | 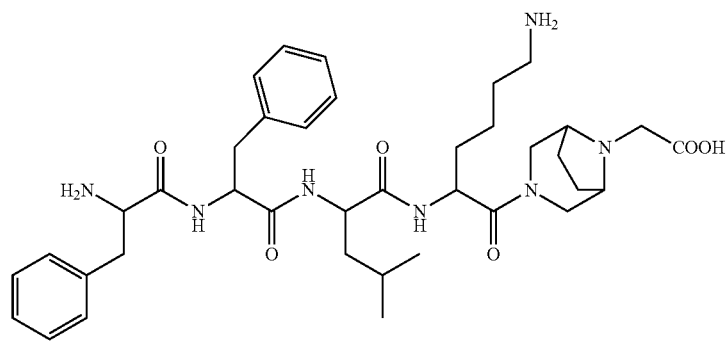 [SMILES: CC(C)CC(NC(=O)C(Cc1ccccc1)NC(=O)C(N)Cc1ccccc1)C(=O)NC(CCCCN)C(=O)N1CC2CCC(C1)N2CC(=O)O] |

TABLE 1-continued
List of Short-chain peptides as KOR agonist
| Sr. No | Structures |
|---|---|
| 81 | 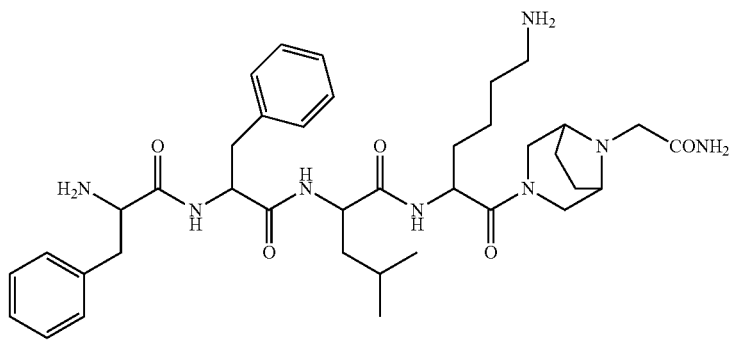 [SMILES: CC(C)CC(NC(=O)C(Cc1ccccc1)NC(=O)C(N)Cc1ccccc1)C(=O)NC(CCCCN)C(=O)N1CC2CCC(C1)N2CC(N)=O] |
| 82 | 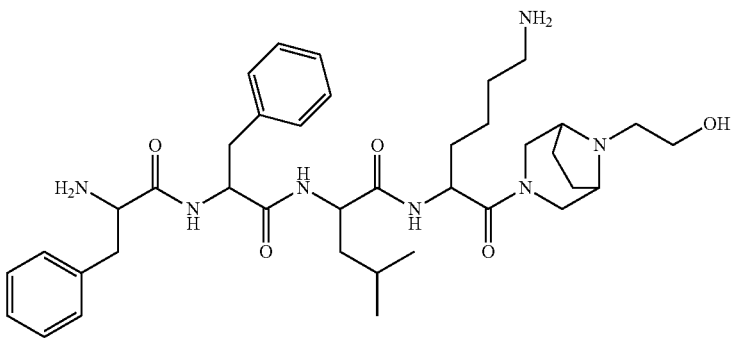 [SMILES: CC(C)CC(NC(=O)C(Cc1ccccc1)NC(=O)C(N)Cc1ccccc1)C(=O)NC(CCCCN)C(=O)N1CC2CCC(C1)N2CCO] |
| 83 | 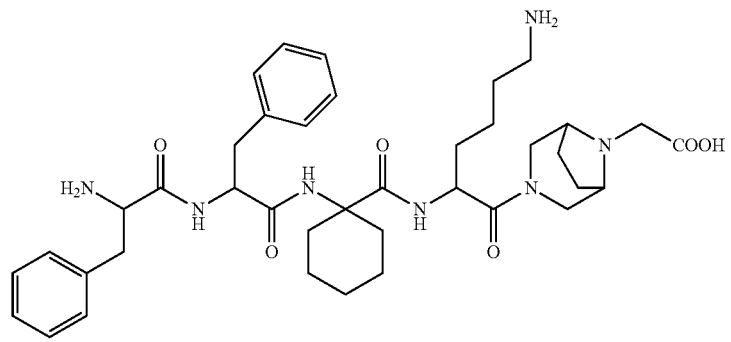 [SMILES: NCCCCC(NC(=O)C1(NC(=O)C(Cc2ccccc2)NC(=O)C(N)Cc2ccccc2)CCCCC1)C(=O)N1CC2CCC(C1)N2CC(=O)O] |
| 84 | 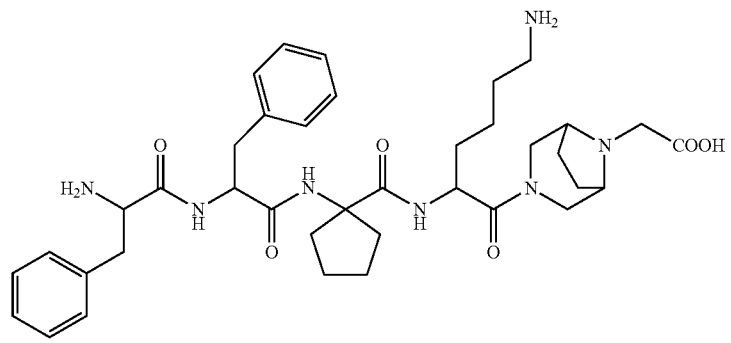 [SMILES: NCCCCC(NC(=O)C1(NC(=O)C(Cc2ccccc2)NC(=O)C(N)Cc2ccccc2)CCCC1)C(=O)N1CC2CCC(C1)N2CC(=O)O] |

TABLE 1-continued
List of Short-chain peptides as KOR agonist
| Sr. No | Structures |
|---|---|
| 85 | 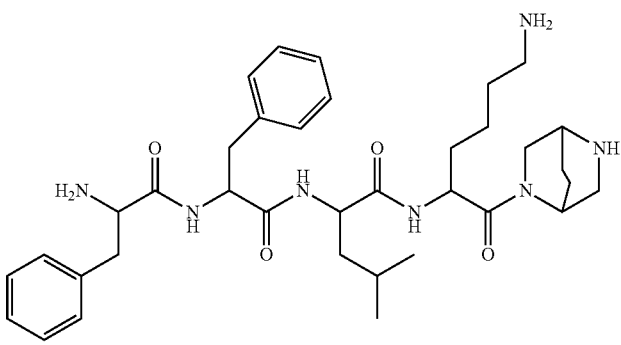 [SMILES: CC(C)CC(NC(=O)C(Cc1ccccc1)NC(=O)C(N)Cc1ccccc1)C(=O)NC(CCCCN)C(=O)N1CC2CCC1CN2] |
| 86 | 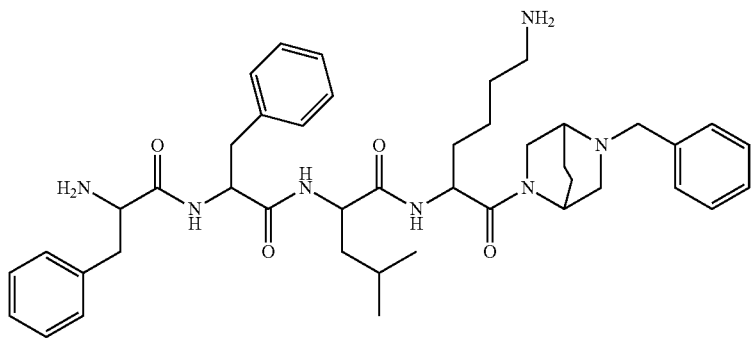 [SMILES: CC(C)CC(NC(=O)C(Cc1ccccc1)NC(=O)C(N)Cc1ccccc1)C(=O)NC(CCCCN)C(=O)N1CC2CCC1CN2Cc1ccccc1] |
| 87 | 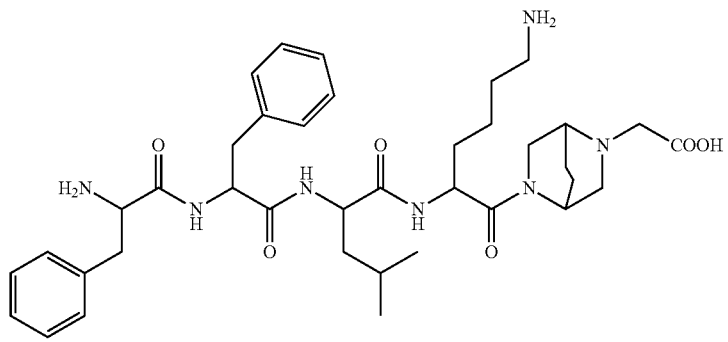 [SMILES: CC(C)CC(NC(=O)C(Cc1ccccc1)NC(=O)C(N)Cc1ccccc1)C(=O)NC(CCCCN)C(=O)N1CC2CCC1CN2CC(=O)O] |
| 88 | 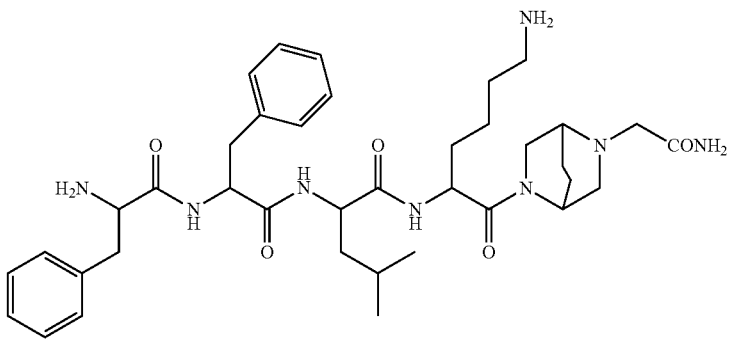 [SMILES: CC(C)CC(NC(=O)C(Cc1ccccc1)NC(=O)C(N)Cc1ccccc1)C(=O)NC(CCCCN)C(=O)N1CC2CCC1CN2CC(N)=O] |

TABLE 1-continued

List of Short-chain peptides as KOR agonist

| Sr. No | Structures |
|---|---|
| 89 | 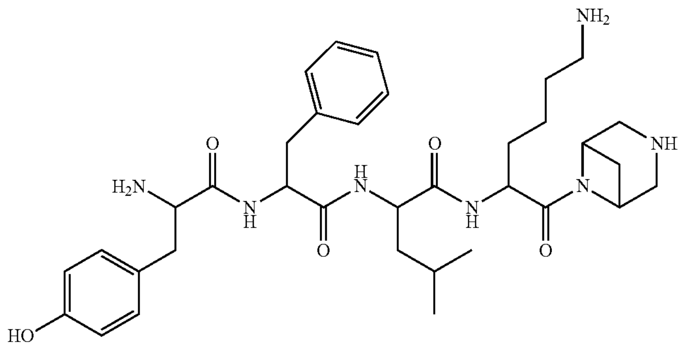 [SMILES: CC(C)CC(NC(=O)C(Cc1ccccc1)NC(=O)C(N)Cc1ccc(O)cc1)C(=O)NC(CCCCN)C(=O)N1C2CNCC1C2] |
| 90 | 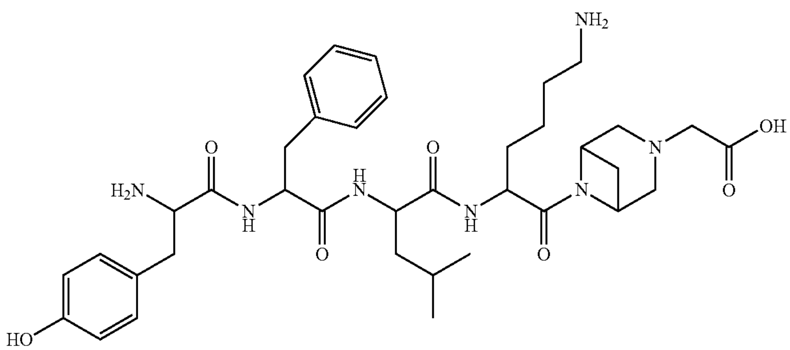 [SMILES: CC(C)CC(NC(=O)C(Cc1ccccc1)NC(=O)C(N)Cc1ccc(O)cc1)C(=O)NC(CCCCN)C(=O)N1C2CC1CN(CC(=O)O)C2] |
| 91 | 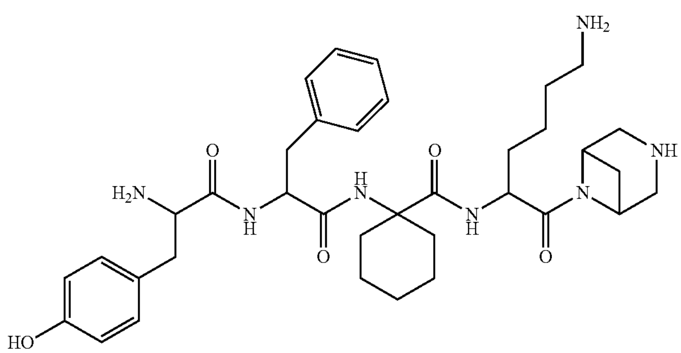 [SMILES: NCCCCC(NC(=O)C1(NC(=O)C(Cc2ccccc2)NC(=O)C(N)Cc2ccc(O)cc2)CCCCC1)C(=O)N1C2CNCC1C2] |
| 92 | 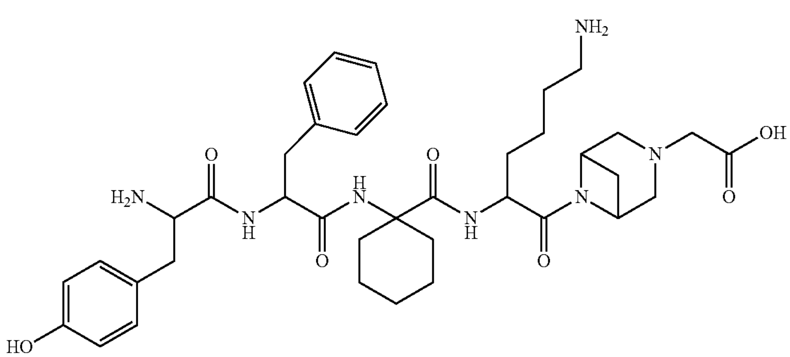 [SMILES: NCCCCC(NC(=O)C1(NC(=O)C(Cc2ccccc2)NC(=O)C(N)Cc2ccc(O)cc2)CCCCC1)C(=O)N1C2CC1CN(CC(=O)O)C2] |

TABLE 1-continued
List of Short-chain peptides as KOR agonist
| Sr. No | Structures |
|---|---|
| 93 | 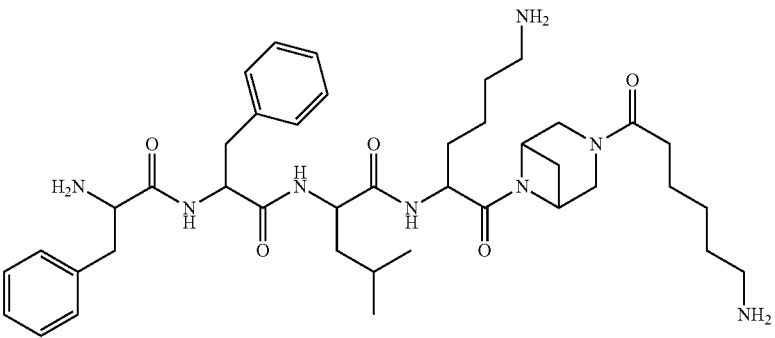 [SMILES: CC(C)CC(NC(=O)C(Cc1ccccc1)NC(=O)C(N)Cc1ccccc1)C(=O)NC(CCCCN)C(=O)N1C2CC1CN(C(=O)CCCCCN)C2] |
| 94 | 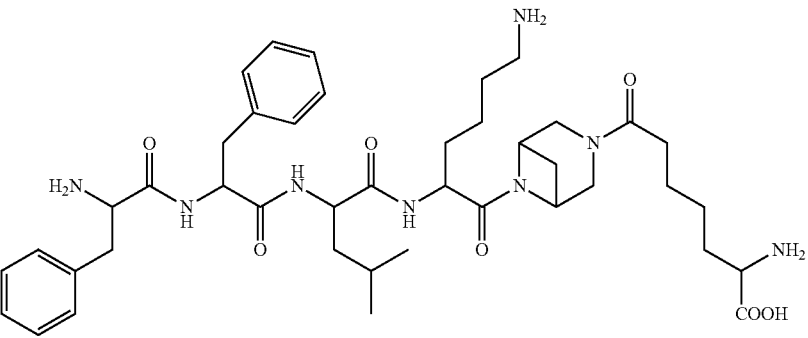 [SMILES: CC(C)CC(NC(=O)C(Cc1ccccc1)NC(=O)C(N)Cc1ccccc1)C(=O)NC(CCCCN)C(=O)N1C2CC1CN(C(=O)CCCCC(N)C(=O)O)C2] |
| 95 | 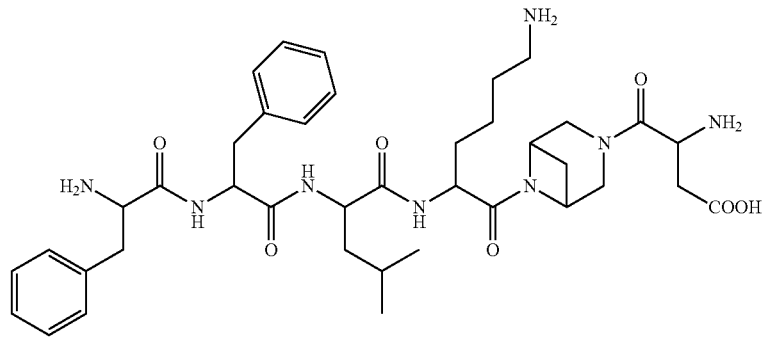 [SMILES: CC(C)CC(NC(=O)C(Cc1ccccc1)NC(=O)C(N)Cc1ccccc1)C(=O)NC(CCCCN)C(=O)N1C2CC1CN(C(=O)C(N)CC(=O)O)C2] |
| 96 | 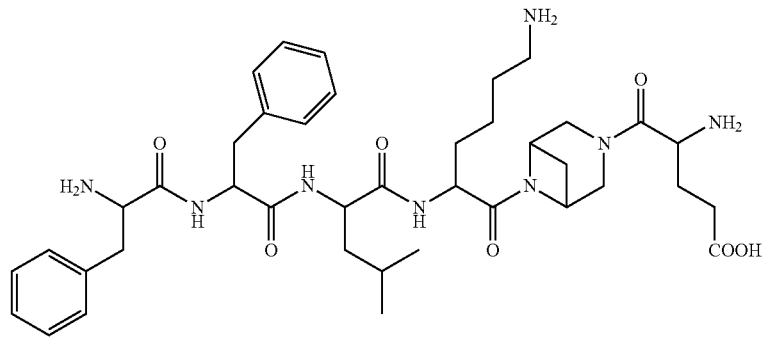 [SMILES: CC(C)CC(NC(=O)C(Cc1ccccc1)NC(=O)C(N)Cc1ccccc1)C(=O)NC(CCCCN)C(=O)N1C2CC1CN(C(=O)C(N)CCC(=O)O)C2] |

TABLE 1-continued
List of Short-chain peptides as KOR agonist
| Sr. No | Structures |
|---|---|
| 97 | 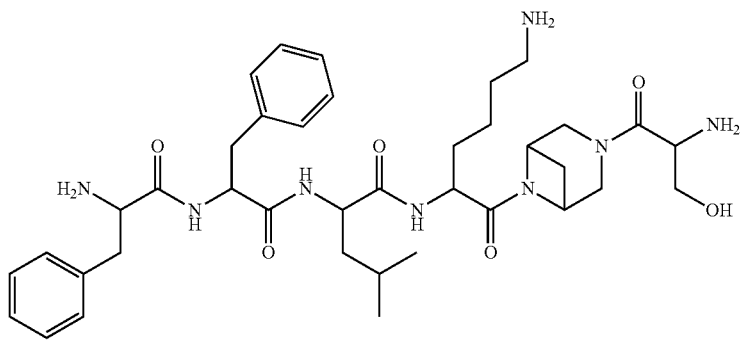 [SMILES: CC(C)CC(NC(=O)C(Cc1ccccc1)NC(=O)C(N)Cc1ccccc1)C(=O)NC(CCCCN)C(=O)N1C2CC1CN(C(=O)C(N)CO)C2] |
| 98 | 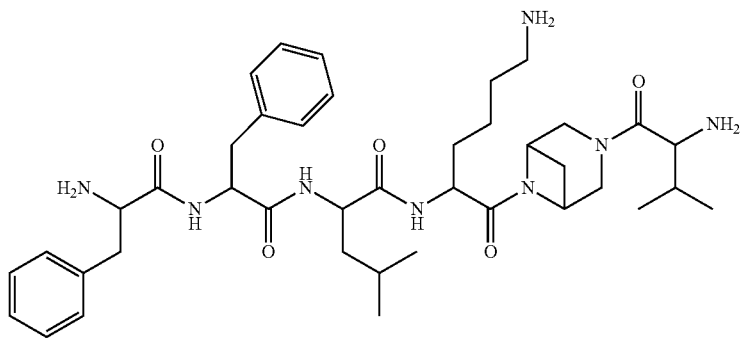 [SMILES: CC(C)CC(NC(=O)C(Cc1ccccc1)NC(=O)C(N)Cc1ccccc1)C(=O)NC(CCCCN)C(=O)N1C2CC1CN(C(=O)C(N)C(C)C)C2] |
| 99 | 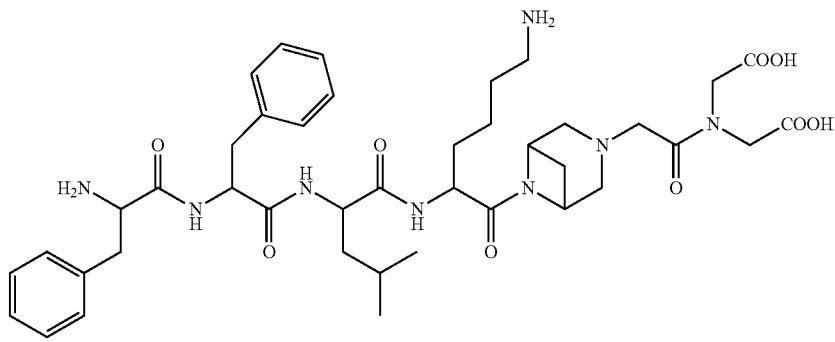 [SMILES: CC(C)CC(NC(=O)C(Cc1ccccc1)NC(=O)C(N)Cc1ccccc1)C(=O)NC(CCCCN)C(=O)N1C2CC1CN(CC(=O)N(CC(=O)O)CC(=O)O)C2] |
| 100 | 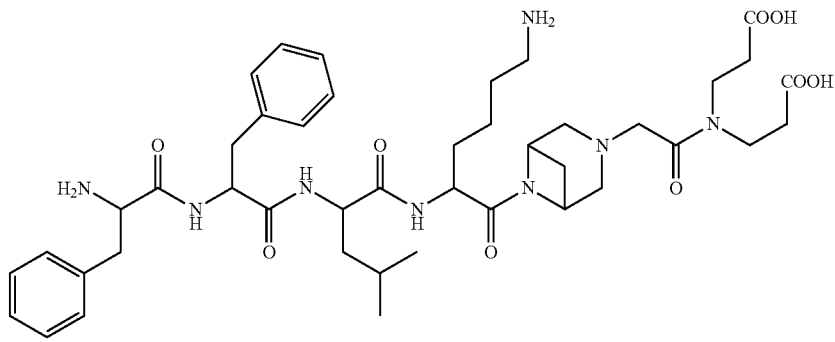 [SMILES: CC(C)CC(NC(=O)C(Cc1ccccc1)NC(=O)C(N)Cc1ccccc1)C(=O)NC(CCCCN)C(=O)N1C2CC1CN(CC(=O)N(CCC(=O)O)CCC(=O)O)C2] |

TABLE 1-continued

List of Short-chain peptides as KOR agonist

| Sr. No | Structures |
|---|---|
| 101 | 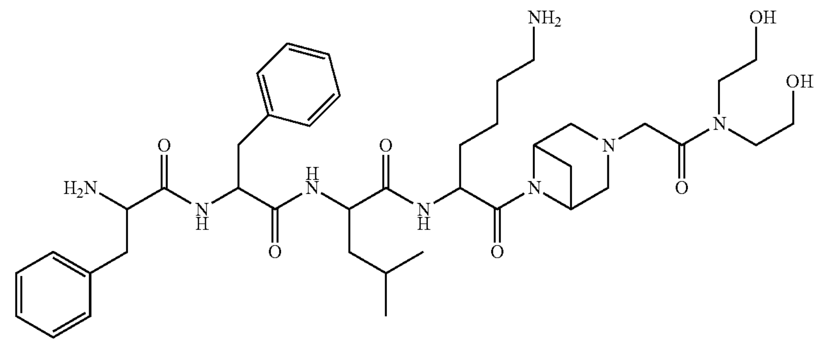 [SMILES: CC(C)CC(NC(=O)C(Cc1ccccc1)NC(=O)C(N)Cc1ccccc1)C(=O)NC(CCCCN)C(=O)N1C2CC1CN(CC(=O)N(CCO)CCO)C2] |
| 102 | 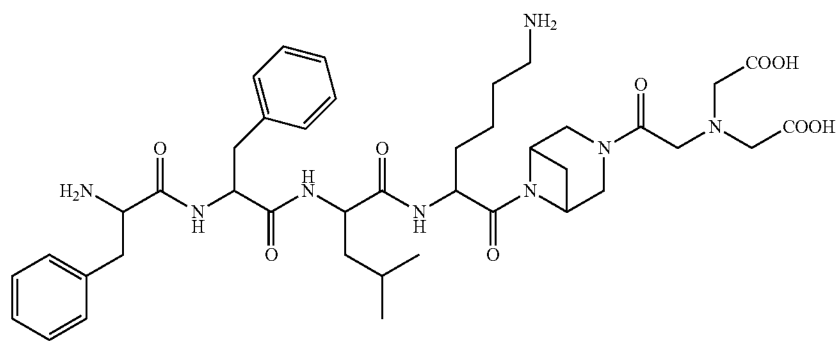 [SMILES: CC(C)CC(NC(=O)C(Cc1ccccc1)NC(=O)C(N)Cc1ccccc1)C(=O)NC(CCCCN)C(=O)N1C2CC1CN(C(=O)CN(CC(=O)O)CC(=O)O)C2] |
| 103 | 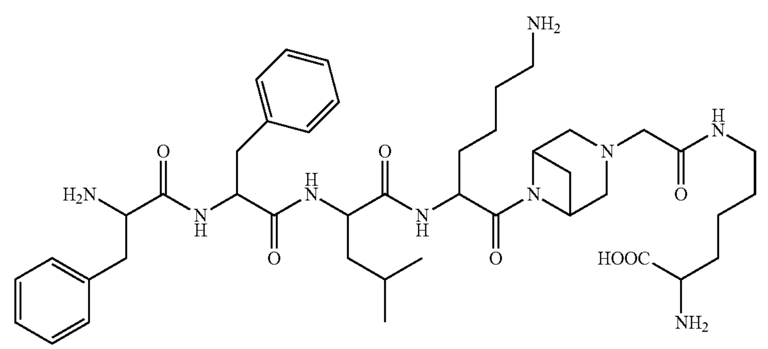 [SMILES: CC(C)CC(NC(=O)C(Cc1ccccc1)NC(=O)C(N)Cc1ccccc1)C(=O)NC(CCCCN)C(=O)N1C2CC1CN(CC(=O)NCCCCC(N)C(=O)O)C2] |
| 104 | 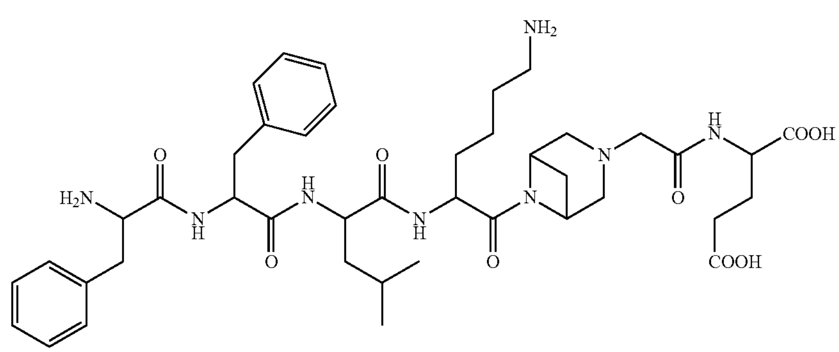 [SMILES: CC(C)CC(NC(=O)C(Cc1ccccc1)NC(=O)C(N)Cc1ccccc1)C(=O)NC(CCCCN)C(=O)N1C2CC1CN(CC(=O)NC(CCC(=O)O)C(=O)O)C2] |

TABLE 1-continued

List of Short-chain peptides as KOR agonist

| Sr. No | Structures |
|---|---|
| 105 | 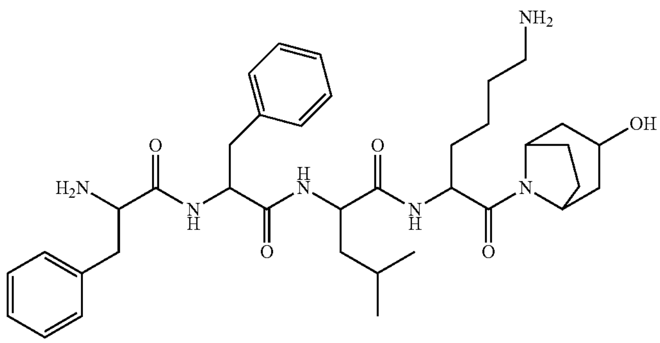 |
| 106 | 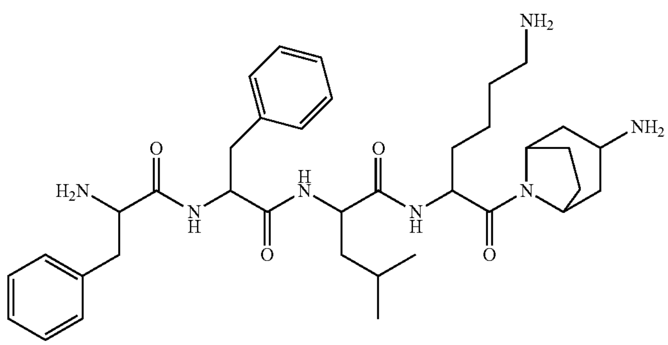 [SMILES: CC(C)CC(NC(=O)C(Cc1ccccc1)NC(=O)C(N)Cc1ccccc1)C(=O)NC(CCCCN)C(=O)N1C2CCC1CC(N)C2] |
| 107 | 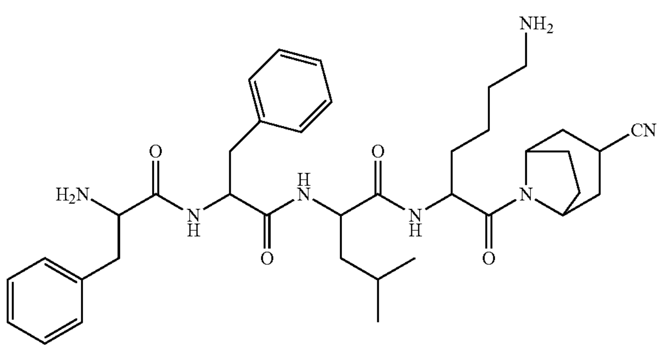 [SMILES: CC(C)CC(NC(=O)C(Cc1ccccc1)NC(=O)C(N)Cc1ccccc1)C(=O)NC(CCCCN)C(=O)N1C2CCC1CC(C#N)C2] |
| 108 | 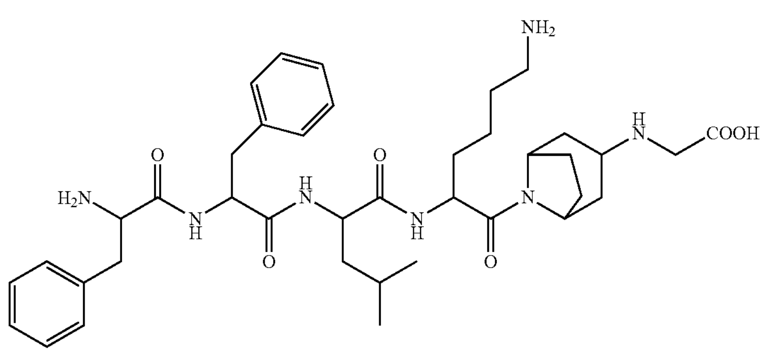 [SMILES: CC(C)CC(NC(=O)C(Cc1ccccc1)NC(=O)C(N)Cc1ccccc1)C(=O)NC(CCCCN)C(=O)N1C2CCC1CC(NCC(=O)O)C2] |

TABLE 1-continued
List of Short-chain peptides as KOR agonist
| Sr. No | Structures |
|---|---|
| 109 | 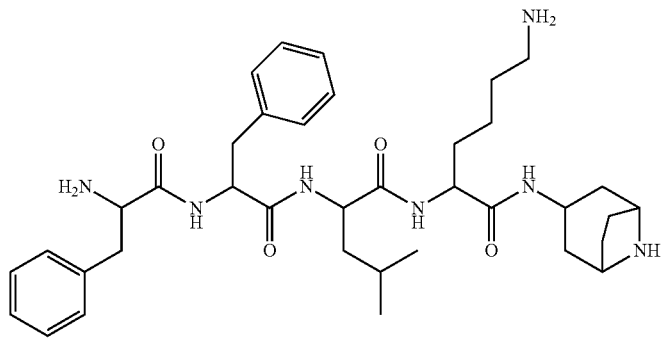 [SMILES: CC(C)CC(NC(=O)C(Cc1ccccc1)NC(=O)C(N)Cc1ccccc1)C(=O)NC(CCCCN)C(=O)NC1CC2CCC(C1)N2] |
| 110 | 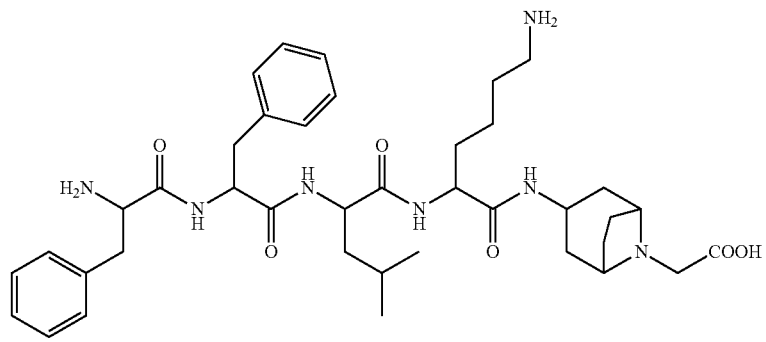 [SMILES: CC(C)CC(NC(=O)C(Cc1ccccc1)NC(=O)C(N)Cc1ccccc1)C(=O)NC(CCCCN)C(=O)NC1CC2CCC(C1)N2CC(=O)O] |
| 111 | 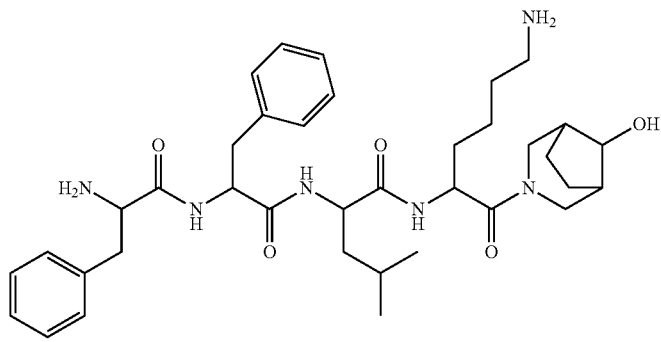 |
| 112 | 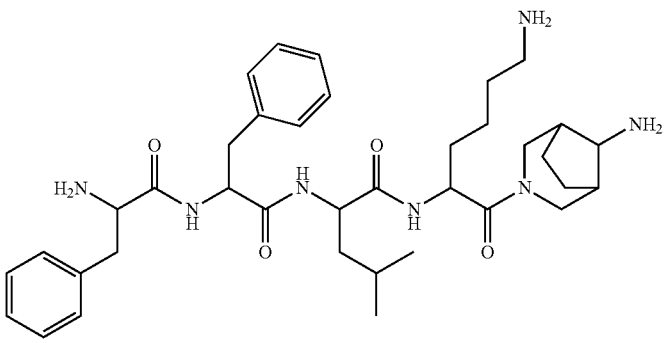 [SMILES: CC(C)CC(NC(=O)C(Cc1ccccc1)NC(=O)C(N)Cc1ccccc1)C(=O)NC(CCCCN)C(=O)N1CC2CCC(C1)C2N] |

TABLE 1-continued

List of Short-chain peptides as KOR agonist

| Sr. No | Structures |
|---|---|
| 113 | 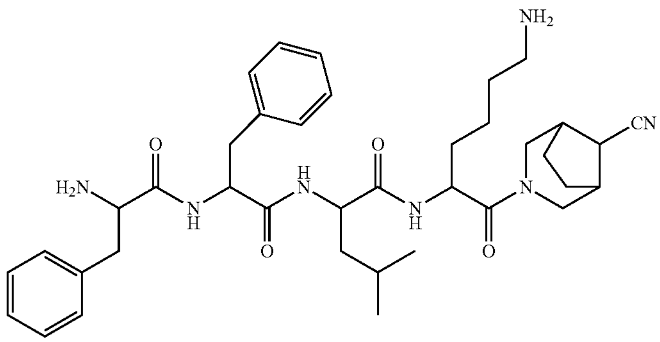 [SMILES: CC(C)CC(NC(=O)C(Cc1ccccc1)NC(=O)C(N)Cc1ccccc1)C(=O)NC(CCCCN)C(=O)N1CC2CCC(C1)C2C#N] |
| 114 | 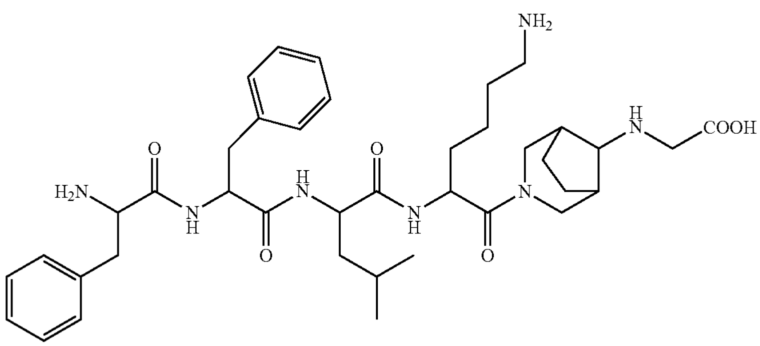 [SMILES: CC(C)CC(NC(=O)C(Cc1ccccc1)NC(=O)C(N)Cc1ccccc1)C(=O)NC(CCCCN)C(=O)N1CC2CCC(C1)C2NCC(=O)O] |
| 115 | 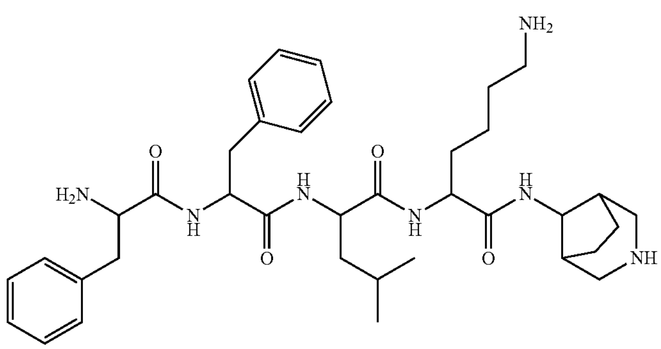 [SMILES: CC(C)CC(NC(=O)C(Cc1ccccc1)NC(=O)C(N)Cc1ccccc1)C(=O)NC(CCCCN)C(=O)NC1C2CCC1CNC2] |
| 116 | 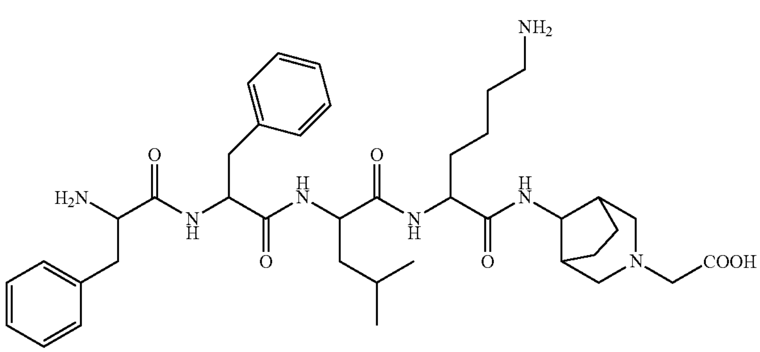 [SMILES: CC(C)CC(NC(=O)C(Cc1ccccc1)NC(=O)C(N)Cc1ccccc1)C(=O)NC(CCCCN)C(=O)NC1C2CCC1CN(CC(=O)O)C2] |

Preparation of the Short Chain Peptides:

Several synthetic routes can be employed to prepare the short chain peptides of the present invention. The short chain peptides of formula (I), where all symbols are as defined earlier can be synthesized, using the methods described below, together with conventional techniques known to those skilled in the art of peptide synthesis, or variations thereon as appreciated by those skilled in the art. Referred methods include, but not limited to those described below. The short chain peptides described herein may be produced by chemical synthesis using suitable variations of both the solution-phase (preferably, using Boc-chemistry; as generally described in M. Bodansky, A. Bodansky, "The practice of peptide synthesis", Springer-Verlag, Berlim, 1984; E. Gross, J. Meinhofer, "The peptide synthesis, analysis, biology", Vol. 1, Academic Press, London, 1979) and/or solid-phase techniques, such as those described generally in G. Barany & R. B. Merrifield, "The peptides: Analysis, synthesis, Biology"; Volume 2—"Special methods in peptide synthesis, Part A", pp. 3-284, E. Gross & J. Meienhofer, Eds., Academic Press, New York, 1980; and in J. M. Stewart and J. D. Young, "Solid-phase peptide synthesis" 2nd Ed., Pierce chemical Co., Rockford, Il., 1984.

The preferred strategy for preparing the short chain peptides of this invention is based on the use of solid phase and/or solution phase approach.

Solid Phase Peptide Synthesis (SPPS):

The compounds of the formula (I) can be prepared by solid phase synthesis as described in Scheme-1, along with suitable modifications/variations, which are well within the scope of a person skilled in the art.

The use of Fmoc-based SPPS approach, wherein Fmoc (9-fluorenylmethoxycarbonyl) group is used for temporary protection of the α-amino group, in combination with the acid labile protecting groups, such as tert-butoxycarbonyl (Boc), tert-butyl (Bu$^t$), Trityl (Trt) groups (FIG. 1), for temporary protection of the amino acid side chains, if present (see for example E. Atherton & R. C. Sheppard, "The Fluorenylmethoxycarbonyl amino protecting group", in "The peptides: Analysis, synthesis, Biology"; Volume 9—"Special methods in peptide synthesis, Part C", pp. 1-38, S. Undenfriend & J. Meienhofer, Eds., Academic Press, San Diego, 1987).

The short chain peptides can be synthesized in a stepwise manner on an insoluble polymer support (resin), starting from the C-terminus of the peptide. In an embodiment, the synthesis is initiated by appending the C-terminal amino acid of the peptide to the resin through formation of an amide, ester or ether linkage. This allows the eventual release of the resulting peptide as a C-terminal amide, carboxylic acid or alcohol, respectively.

In the Fmoc-based SPPS, the C-terminal amino acid and all other amino acids used in the synthesis are required to have their α-amino groups and side chain functionalities (if present) differentially protected (orthogonal protection), such that the α-amino protecting group may be selectively removed during the synthesis, using suitable base such as 20% piperidine solution, without any premature cleavage of peptide from resin or deprotection of side chain protecting groups, usually protected with the acid labile protecting groups.

The coupling of an amino acid is performed by activation of its carboxyl group as an active ester and reaction thereof with unblocked α-amino group of the N-terminal amino acid appended to the resin. After every coupling and deprotection, peptidyl-resin was washed with the excess of solvents, such as DMF, DCM and diethyl ether. The sequence of α-amino group deprotection and coupling is repeated until the desired peptide sequence is assembled (Scheme 1). The peptide is then cleaved from the resin with concomitant deprotection of the side chain functionalities, using an appropriate cleavage mixture, usually in the presence of appropriate scavengers to limit side reactions. The resulting peptide is finally purified by reverse phase HPLC.

The synthesis of the peptidyl-resins required as precursors to the final peptides utilizes commercially available cross-linked polystyrene polymer resins (Novabiochem, San Diego, Calif.). Preferred for use in this invention is Fmoc-PAL-PEG-PS resin, 4-(2',4'-dimethoxyphenyl-Fmoc-aminomethyl)-phenoxyacetyl-p-methyl benzhydrylamine resin (Fmoc-Rink amide MBHA resin), 2-chloro-Trityl-chloride resin or p-benzyloxybenzyl alcohol resin (HMP resin), trichloroacedimidate resin, p-Nitrophenylcarbonate wang resin to which the C-terminal amino acid may or may not be already attached. If the C-terminal amino acid is not attached, its attachment may be achieved by HOBt active ester of the Fmoc-protected amino acid formed by its reaction with DIPCDI. In case of 2-Chloro-trityl resin, coupling of first Fmoc-protected amino acid was achieved, using DIPEA. For the assembly of next amino acid, N-terminal protection of peptidyl resin was selectively deprotected using 10-20% piperidine solution. After every coupling and deprotection, excess of amino acids and coupling reagents were removed by washing with DMF, DCM and ether. Coupling of the subsequent amino acids can be accomplished using HOBt or HOAt active esters produced from DIPCDI/HOBt or DIPCDI/HOAt, respectively. In case of some difficult coupling, especially coupling of those amino acids, which are hydrophobic or amino acids with bulky side chain protection; complete coupling can be achieved using a combination of highly efficient coupling agents such as HBTU, PyBOP or TBTU, with additives such as DIPEA.

The synthesis of the short chain peptides described herein can be carried out by using batchwise or continuous flow peptide synthesis apparatus, such as CS-Bio or AAPPTEC peptide synthesizer, utilizing the Fmoc/trityl protection strategy. The non-natural non-commercial amino acids present at different position were incorporated into the peptide chain, using one or more methods known in the art. In one approach, Fmoc-protected non-natural amino acid was prepared in solution, using appropriate literature procedures.

FIG. 1: Examples of some of the protected amino acids used in Fmoc based-solid phase peptide synthesis (SPPS) of short chain peptides

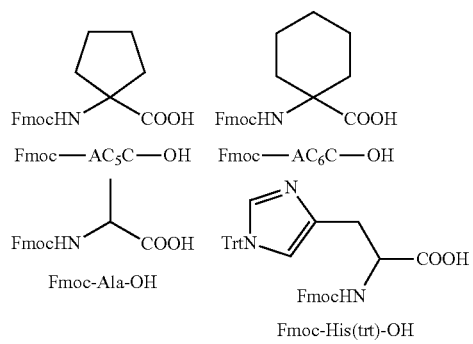

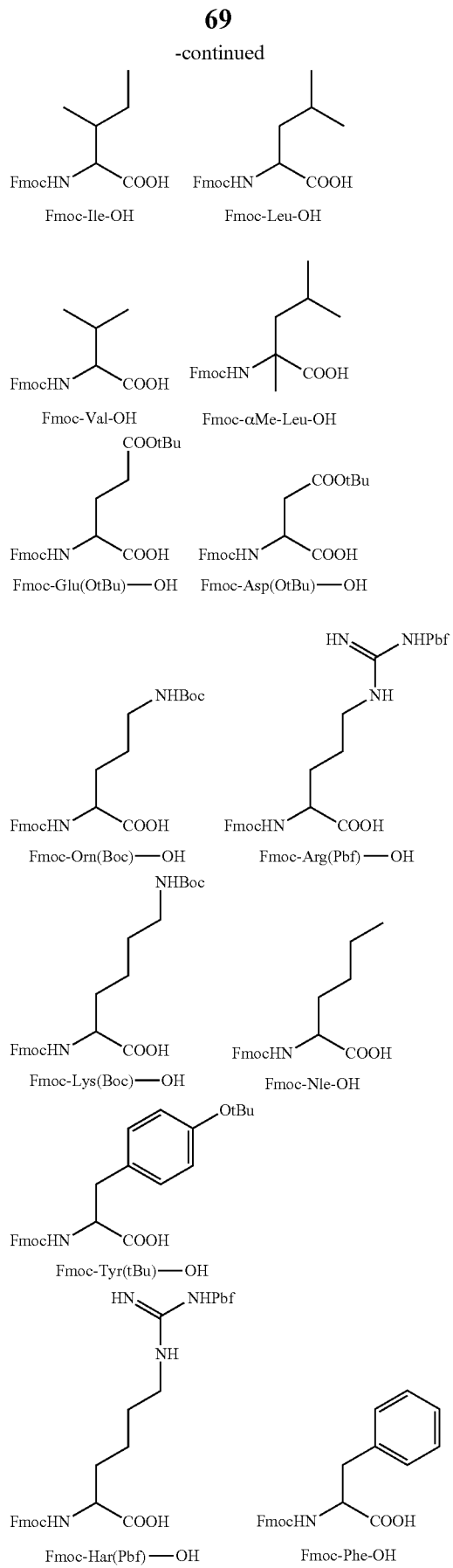

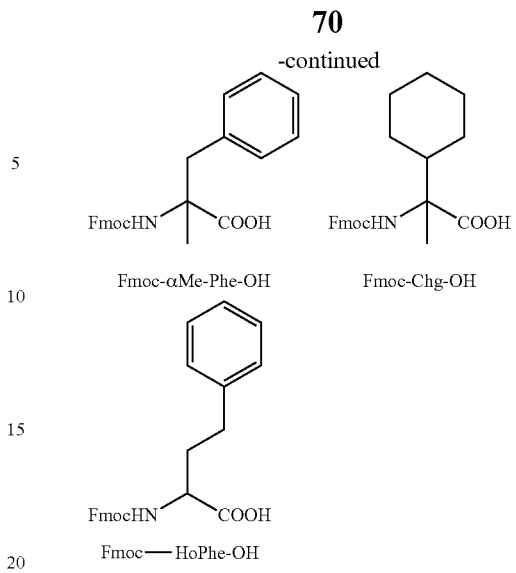

The Fmoc-protected α-methylated amino acids were prepared using asymmetric Strecker synthesis (Boesten, W. H. J., et al., Org. Lett., 3(8), 2001, 1121-1124; Cativiela C., Diaz-de-villegas M. D., Tetrahedran Asymmetry, 9, 1988, 3517-3599). The resulting derivative was then used in the step-wise synthesis of the peptide. Alternatively, the required non-natural amino acid was built on the resin directly using synthetic organic chemistry procedures and a linear peptide chain were building.

The peptide-resin precursors for their respective short-chain peptides may be cleaved and deprotected using suitable variations of any of the standard cleavage procedures described in the literature (King D. S., et al., Int. J. Peptide Protein Res., 1990, 36, 255-266). A preferred method for use in this invention is the use of TFA cleavage mixture, in the presence of water and TIPS as scavengers. Typically, the peptidyl-resin was incubated in TFA/Water/TIPS (95:2.5:2.5) for 1.5-4 hrs at room temperature. The cleaved resin is then filtered off and the TFA solution is concentrated or dried under reduced pressure. The resulting crude peptide is either precipitated or washed with $Et_2O$ or is re-dissolved directly into DMF or 50% aqueous acetic acid for purification by preparative HPLC.

The short chain peptides with the desired purity can be obtained by purification using preparative HPLC. The solution of crude peptide is injected into a semi-Prep column (Luna 10μ; $C_{18}$; 100 A°), dimension 250×50 mm and eluted with a linear gradient of ACN in water, both buffered with 0.1% TFA, using a flow rate of 40 mL/min with effluent monitoring by PDA detector at 220 nm. The structures of the purified short chain peptides can be confirmed by Electrospray Mass Spectroscopy (ES-MS) analysis.

All the peptide prepared were isolated as trifluoro-acetate salt, with TFA as a counter ion, after the Prep-HPLC purification. However, some peptides were subjected for desalting, by passing through a suitable ion exchange resin bed, preferably through anion-exchange resin Dowex SBR P(Cl) or an equivalent basic anion-exchange resin. In some cases, TFA counter ions were replaced with acetate ions, by passing through suitable ion-exchange resin: eluted with dilute acetic acid buffer. For the preparation of the hydrochloride salt of peptides, in the last stage of the manufacturing, selected peptides, with the acetate salt was treated with 4 M HCl. The resulting solution was filtered through a membrane filter (0.2 □m) and subsequently lyophilized to yield the white to off-white HCl salt. Following similar techniques and/or such suitable modifications, which are well within the scope of persons skilled in the art, other suitable pharmaceutically acceptable salts of the short chain peptides of the present invention were prepared.

Scheme 1: General scheme for the synthesis of compounds of formula (I) by solid phase method.

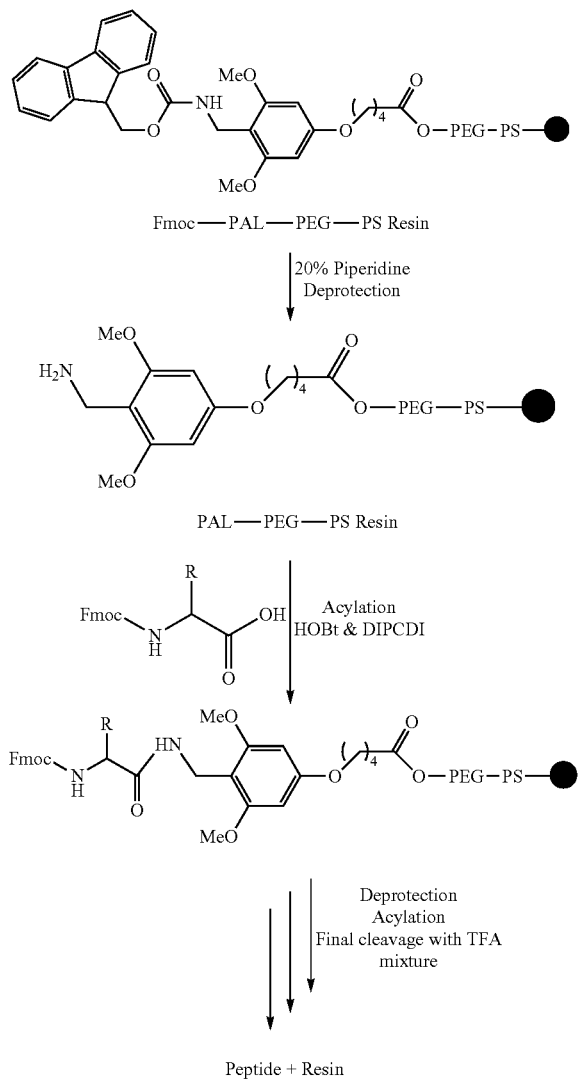

General Method of Preparation of Short Chain Peptides, Using SPPS Approach:
Assembly of Short Chain Peptides on Resin:

Sufficient quantity (50-100 mg) of Fmoc-PAL-PEG-PS resin or Fmoc-Rink amide MBHA resin, or 2-chloro-trityl resin loading: 0.5-1.0 mmol/g was swelled in DMF (1-10 mL/100 mg of resin) for 2-10 minutes. The Fmoc-group on resin was removed by incubation of resin with 10-30% piperidine in DMF (10-30 mL/100 mg of resin), for 10-30 minutes. Deprotected resin was filtered and washed excess of DMF, DCM and ether. Washed resin was incubated in freshly distilled DMF (1 mL/100 mg of resin), under nitrogen atmosphere for 5 minutes. A 0.5 M solution of first Fmoc-protected amino acid (1-3 eq.), pre-activated with HOBt (1-3 eq.) and DIPCDI (1-2 eq.) in DMF was added to the resin, and the resin was then shaken for 1-3 hrs, under nitrogen atmosphere. Coupling completion was monitored using a qualitative ninhydrin test. After the coupling of first amino acid, the resin was washed with DMF, DCM and Diethyl ether. For the coupling of next amino acid, firstly, the Fmoc-protection on first amino acid, coupled with resin was deprotected, using a 10-20% piperidine solution, followed by the coupling the Fmoc-protected second amino acid, using a suitable coupling agents, and as described above. The repeated cycles of deprotection, washing, coupling and washing were performed until the desired peptide chain was assembled on resin, as per general Scheme 1 above. Finally, the Fmoc-protected peptidyl-resin prepared above was deprotected by 20% piperidine treatment as described above and the peptidyl-resins were washed with DMF, DCM and Diethyl ether. Resin containing desired peptide was dried under nitrogen pressure for 10-15 minutes and subjected for cleavage/deprotection.

Using above protocol and suitable variations thereof which are within the scope of a person skilled in the art, the short-chain peptides designed in the present invention were prepared, using Fmoc-SPPS approach. Furthermore, resin bound short chain peptides were cleaved and deprotected, purified and characterized using following protocol.

Cleavage and Deprotection:

The desired short chain peptides were cleaved and deprotected from their respective peptidyl-resins by treatment with TFA cleavage mixture as follows. A solution of TFA/Water/Triisopropylsilane (95:2.5:2.5) (10 mL/100 mg of peptidyl-resin) was added to peptidyl-resins and the mixture was kept at room temperature with occasional starring. The resin was filtered, washed with a cleavage mixture and the combined filtrate was evaporated to dryness. Residue obtained was dissolved in 10 mL of water and the aqueous layer was extracted 3 times with ether (20 mL each) and finally the aqueous layer was freeze-dried. Crude peptide obtained after freeze-drying was purified by preparative HPLC as follows:

Preparative HPLC Purification of the Crude Short Chain Peptides:

Preparative HPLC was carried out on a Shimadzu LC-8A liquid chromatograph. A solution of crude peptide dissolved in DMF or water was injected into a semi-Prep column (Luna 10☐; $C_{18}$; 100 A°), dimension 250×50 mm and eluted with a linear gradient of ACN in water, both buffered with 0.1% TFA, using a flow rate of 15-50 mL/min, with effluent monitoring by PDA detector at 220 nm. A typical gradient of 20% to 70% of water-ACN mixture, buffered with 0.1% TFA was used, over a period of 50 minutes, with 1% gradient change per minute. The desired product eluted were collected in a single 10-20 mL fraction and pure short-chain peptides were obtained as amorphous white powders by lyophilisation of respective HPLC fractions.

HPLC Analysis of the Purified Short Chain Peptides

After purification by preparative HPLC as described above, each peptide was analyzed by analytical RP-HPLC on a Shimadzu LC-10AD analytical HPLC system. For analytical HPLC analysis of short-chain peptides, Luna 5 ☐; $C_{18}$; 100 A°, dimension 250×4.6 mm column was used, with a linear gradient of 0.1% TFA and ACN buffer and the acquisition of chromatogram was carried out at 220 nm, using a PDA detector.

Characterization by Mass Spectrometry

Each peptide was characterized by electrospray ionisation mass spectrometry (ESI-MS), either in flow injection or LC/MS mode. Triple quadrupole mass spectrometers (API-3000 (MDS-SCIES, Canada) was used in all analyses in positive and negative ion electrospray mode. Full scan data was acquired over the mass range of quadrupole, operated at unit resolution. In all cases, the experimentally measured molecular weight was within 0.5 Daltons of the calculated monoisotopic molecular weight. Quantification of the mass chromatogram was done using Analyst 1.4.1 software.

Representative Example of Automated Solid Phase Synthesis of Compound No. 17

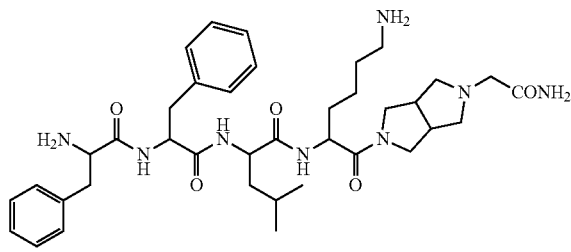 [SMILES: CC(C)CC(NC(=O)C(Cc1ccccc1)NC(=O)C(N)Cc1ccccc1)C(=O)NC(CCCCN)C(=O)N1CC2CN(CC(N)=O)CC2C1]

The linear short-chain peptide, H$_2$N-Phe-Phe-Leu-Lys-Hpp-PAL-PEG-PS was assembled on an automated CS-Bio 536 PepSynthesiser™ using Fmoc solid phase peptide synthesis (SPPS) approach (Scheme 2). The Fmoc amino acids and the 2-(1H-Benzotriazol-1-yl)-1,1,3,3-tetramethyluroniumtetrafluoroborate (TBTU) were packed together in vials and positioned in the amino acid module of the synthesizer.

A stock solution of diisopropylethylamine (DIPEA; 0.9 M) and DMF were stored in reagent bottles, under dry nitrogen atmosphere. The resin; Fmoc-PAL-PEG-PS (0.38 mmol/g; 1 g) was dried over P$_2$O$_5$, in vacuo (1 hr) and swollen in freshly distilled DMF (5 mL). The swollen resin was slurry packed into a glass column and positioned in the synthesizer. All the synthetic cycles were carried out at a flow rate of 5 mL min$^{-1}$, Table 1. The resin was washed with freshly distilled DMF for 10 minutes. Deprotection of Fmoc group was performed with 20% piperidine in DMF for 10 minutes and the deprotection was monitored by UV detection of the column effluent at 304 nm.

TABLE 2

Automated cycles for solid phase peptide synthesis

| Step | Function | Reagent/Solvent | Number of cycles | Time (Minute) |
|---|---|---|---|---|
| 1 | Wash | Dimethylformamide (DMF) | 2 | 10 |
| 2 | Deprotection | 20% piperidine in DMF | 3 | 15 |
| 3 | Wash | DMF | 3 | 15 |
| 4 | Acylation | Amino acid; TBTU and diisopropylethylamine (in DMF) | Recycle | 120 |
| 5 | Wash | Dimethylformamide | 4 | 10 |

Excess piperidine was removed by three auxiliary wash cycles and a distilled DMF wash cycle, with each cycle of 15 minutes. The amino group was treated with Fmoc-amino acid (4 equivalent), preactivated with TBTU (3.9 equivalent) in the presence of DIPEA (8 equivalent) and recycled for 120 minutes. The excess amino acid and soluble by-products were removed from column and loop by four auxiliary wash cycles and distilled DMF wash cycles, with each cycle of 10 minutes.

Scheme 2: SPPS of Compound No. 17

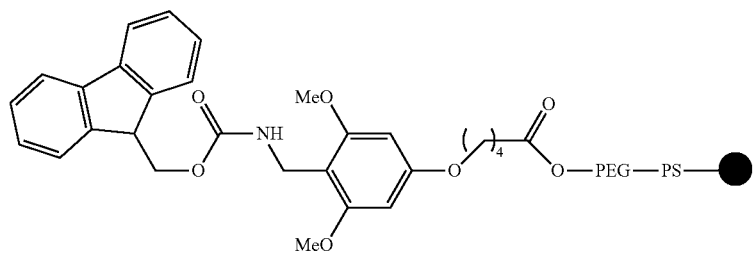

Fmoc—PAL—PEG—PS Resin

1) Piperidine (Fmoc deprotection)
2) Fmoc-Hpp-OH (4 eq.); DMF; TBTU (4 eq.); DIPEA (8 eq); 2 h 3) Washing with DMF and DCM
4) Repeat step 1-3, with follwoing amino acids:
 Fmoc-Lys(Boc)—OH Fmoc-Leu-OH Fmoc-Phe-OH Fmoc-Phe-OH
5) Piperidine (Fmoc deprotection)
6) TFA cleavage
7) RP—HPLC purification

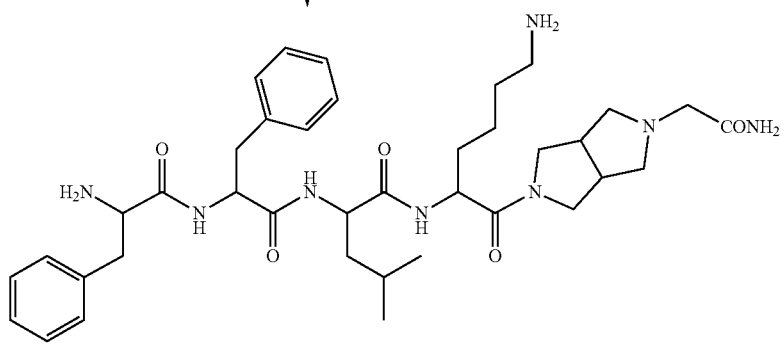

H$_2$N-Phe-Phe-Leu-Lys-Hpp-CONH$_2$
(Compound No. 17)

Furthermore, synthetic cycles (deprotection, wash, acylation and wash) were repeated for complete assembly of linear peptide. Final deprotection cycle was performed with 20% piperidine in DMF for 15 minutes to remove the terminal Fmoc group, followed by wash cycle (10×4 minutes). Completed peptide-resin was filtered through sintered glass filter, washed three times successively with DMF, DCM, methanol, DMF and diethyl ether (100 mL each). Peptide-resin was dried in vacuo over $P_2O_5$ (2 hr) and stored at −20° C.

Ninhydrin resin test was carried out to check the N-terminal free amino group of resin bound peptide. Appearance of blue-purple colouration of the solution and the resin beads indicates the presence of free amino group on resin bound peptide and was considered to be a positive test.

Small-scale cleavage was carried out to assess the purity of resin bound peptide. The dried Peptide-resin (ca 10-mg) was treated with mixture (1 mL) of TFA, water, triisopropylsilane (95:2.5:2.5 v/v), for 90 minutes at room temperature with gentle occasional swirling. The resin was filtered, washed thoroughly with neat TFA (1 mL) and the entire filtrate was evaporated under reduced pressure. Residual TFA was azeotroped three times with diethyl ether (2 mL). Residue obtained was suspended in distilled water (2 mL) and the aqueous layer was extracted three times with diethyl ether (3 mL). The aqueous layer was separated and freeze-dried to yield the crude peptide $H_2N$-Phe-Phe-Leu-Lys-Hpp-$CONH_2$. The lyophilised peptide $H_2N$-Phe-Phe-Leu-Lys-Hpp-$CONH_2$ was dissolved in 0.1% aqueous TFA (ca 1 mg/1 mL) and its purity was analyzed by analytical RP-HPLC and characterized by electrospray ionisation mass spectrometry (ESI-MS). Purity by HPLC: 85% (crude peptide). ESI-MS; Calcd. for $H_2N$-Phe-Phe-Leu-Lys-Hpp-$CONH_2$; 706.8 (M+H$^+$), 728.8 (M+Na$^+$) and 744.8 (M+K$^+$); Found (m/z): 706.8 (M+H$^+$), 728.8 (M+Na$^+$) and 744.8 (M+K$^+$); Purity by HPLC: 99.18% (Pure peptide).

Solution Phase Peptide Synthesis:

The compounds of the formula (I) can be prepared by solution phase synthesis as described in Scheme-3, along with suitable modifications/variations, which are well within the scope of a person skilled in the art.

Step i: Condensation of compound (1) with compound (2) using suitable coupling agents such as EDCl/HOBt, HATU, BOP, PyBOP, DCC/HOBt, and the like, in a suitable solvent such as DCM, DMF and the like, in the presence or absence of base like DMAP, DIPEA can yield a compound (3).

Step ii: Compound (3) can be hydrolysed to compound (4) using suitable base such as LiOH, NaOH, KOH, and the like, in suitable solvent such as THF, MeOH, EtOH, and the like.

Step iii: Condensation of compound (4) with compound (5) using suitable coupling agents such as EDCl/HOBt, HATU, BOP, PyBOP, DCC/HOBt, and the like, in a suitable solvent such as DCM, DMF and the like, in the presence or absence of base like DMAP, DIPEA can yield a compound (6).

Scheme 3: General scheme for the synthesis of compounds of formula (I) by solution phase method.

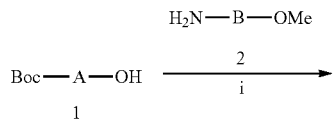

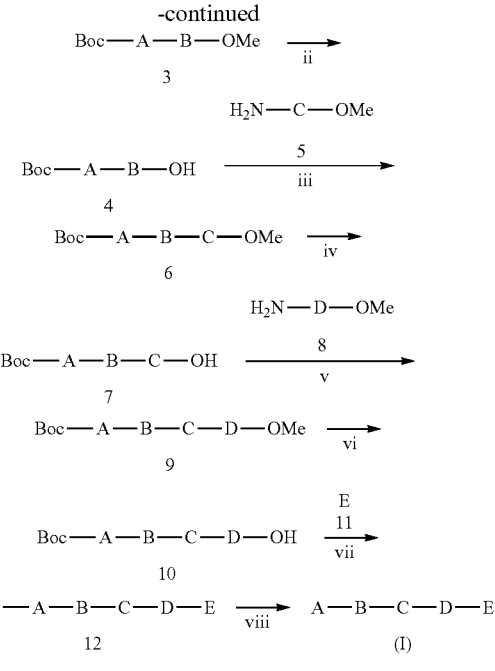

i), iii), v), vii) HOBt, DCC, DCM
ii), iv), vi) NaOH, MeOH
viii) TFA, DCM

Where, A, B, C, D, & E described in description of the invention.

Step iv: Compound (6) can be hydrolysed to compound (7) using suitable base such as LiOH, NaOH, KOH and the like, in suitable solvent such as THF, MeOH, EtOH, and the like.

Step v: Condensation of compound (7) with compound (8) using suitable coupling agents such as EDCl/HOBt, HATU, BOP, PyBOP, DCC/HOBt, and the like, in a suitable solvent such as DCM, DMF and the like, in the presence or absence of base like DMAP, DIPEA can yield a compound (9).

Step vi: Compound (9) can be hydrolysed to compound (10) using suitable base such as LiOH, NaOH, KOH and the like, in suitable solvent such as THF, MeOH, EtOH, and the like.

Step vii: Condensation of compound (10) with compound (11) using suitable coupling agents such as EDCl/HOBt, HATU, BOP, PyBOP, DCC/HOBt, and the like, in a suitable solvent such as DCM, DMF and the like, in the presence or absence of base like DMAP, DIPEA can yield a compound (12).

Step viii: The Boc protecting group of compound (12) can be removed by TFA in suitable solvent such as DCM, and the like, yield a compound of formula (I).

Utilizing the synthetic methods described herein along with other commonly known techniques and suitable variations thereof, the following novel short chain peptides were prepared. This list is indicative of the various groups of short chain peptides, which can be prepared according to the present invention, and are expected to at least include obvious variations of these short chain peptides. However, such disclosure should not be construed as limiting the scope of the invention in any way.

Representative Example of Solution Phase Synthesis of Compound No. 34

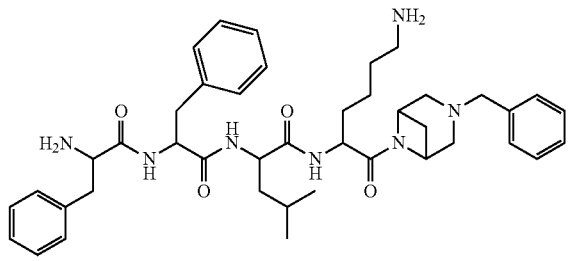 [SMILES: CC(C)CC(NC(=O)C(Cc1ccccc1)NC(=O)C(N)Cc1ccccc1)C(=O)NC(CCCCN)C(=O)N1C2CC1CN(Cc1ccccc1)C2]

Step i: Synthesis of methyl 2-(2-((tert-butoxycarbonyl)amino)-3-phenylpropanamido)-3-phenylpropanoate

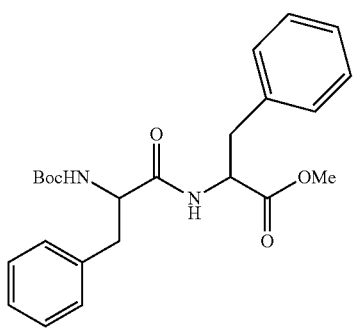 [SMILES: COC(=O)C(Cc1ccccc1)NC(=O)C(Cc1ccccc1)NC(=O)OC(C)(C)C]

To a solution of Boc-Phe-OH (2.0 g, 7.53 mmol) in DCM (20 ml), HOBt (1.02 g, 7.53 mmol) and DCC (1.55 g, 7.53 mmol) was added at 25-30° C. The mixture was stirred for 10 min., and to it H$_2$N-Phe-OMe (1.35 g, 7.53 mmol) was added. The reaction mixture was stirred for 24 h at 25-30° C., filtered and the filtrate was diluted with DCM. Organic layer was washed with saturated NaHCO$_3$ solution, citric acid solution and brine, dried over Na$_2$SO$_4$ and evaporated to get the crude product. Crude product was purified by column chromatography using 0 to 2% MeOH in DCM as an eluent system, to get the title compound as a white solid (3.0 g, 94% yield); ESI-MS: 427.2 (M+H$^+$).

Step ii: Synthesis of 2-(2-((tert-butoxycarbonyl)amino)-3-phenylpropanamido)-3-phenylpropanoic acid

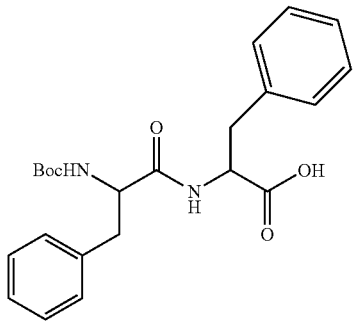 [SMILES: CC(C)(C)OC(=O)NC(Cc1ccccc1)C(=O)NC(Cc1ccccc1)C(=O)O]

To a solution of methyl 2-(2-((tert-butoxycarbonyl)amino)-3-phenylpropanamido)-3-phenylpropanoate (2.0 g, 4.69 mmol) in MeOH (20 ml), NaOH (0.38 g, 9.38 mmol) in H$_2$O (10 ml) was added at 25-30° C. The reaction mixture was stirred for 1 h at 25-30° C. After 1 h MeOH was evaporated & aqueous layer was acidified with citric acid solution, solid was obtained. Filter the solid & dried it to get the title compound as a white solid (1.89, 98% yield); ESI-MS: 413.2 (M+H$^+$).

Step iii: Synthesis of methyl 6,9-dibenzyl-12-isobutyl-2,2-dimethyl-4,7,10-trioxo-3-oxa-5,8,11-triazatridecan-13-oate

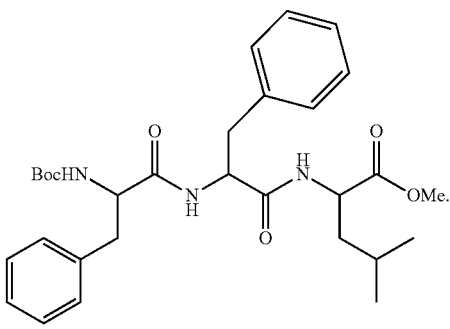 [SMILES: COC(=O)C(CC(C)C)NC(=O)C(Cc1ccccc1)NC(=O)C(Cc1ccccc1)NC(=O)OC(C)(C)C]

To a solution of 2-(2-((tert-butoxycarbonyl)amino)-3-phenylpropanamido)-3-phenylpropanoic acid (1.5 g, 3.64 mmol) in DCM (15 ml), HOBt (0.49 g, 3.64 mmol) and DCC (0.75 g, 3.64 mmol) was added at 25-30° C. The mixture was stirred for 10 min., and to it H$_2$N-Leu-OMe (0.52 g, 3.64 mmol) was added. The reaction mixture was stirred for 24 h at 25-30° C., filtered and the filtrate was diluted with DCM. Organic layer was washed with saturated NaHCO$_3$ solution, citric acid solution and brine, dried over Na$_2$SO$_4$ and evaporated to get the crude product. Crude product was purified by column chromatography using 0 to 2% MeOH in DCM as an eluent system, to get the title compound as a white solid (1.82, 93% yield); ESI-MS: 541.1 (M+H$^+$).

Step iv: Synthesis of 6,9-dibenzyl-12-isobutyl-2,2-dimethyl-4,7,10-trioxo-3-oxa-5,8,11-triazatridecan-13-oic acid

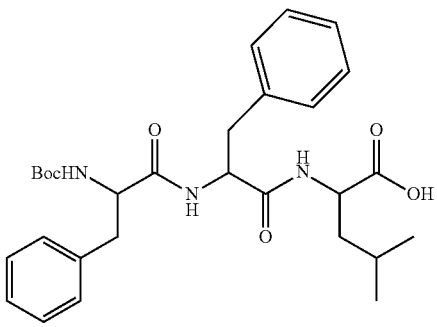 [SMILES: CC(C)CC(NC(=O)C(Cc1ccccc1)NC(=O)C(Cc1ccccc1)NC(=O)OC(C)(C)C)C(=O)O]

To a solution of methyl 6,9-dibenzyl-12-isobutyl-2,2-dimethyl-4,7,10-trioxo-3-oxa-5,8,11-triazatridecan-13-oate (1.3 g, 2.41 mmol) in MeOH (13 ml), NaOH (0.19 g, 4.82 mmol) in H₂O (7 ml) was added at 25-30° C. The reaction mixture was stirred for 1 h at 25-30° C. After 1 h MeOH was evaporated & aqueous layer was acidified with citric acid solution, solid was obtained. Filter the solid & dried it to get the title compound as a white solid (1.22 g, 96% yield); ESI-MS: 527.0 (M+H⁺).

Step v: Synthesis of methyl 6,9-dibenzyl-15-(4-((tert-butoxycarbonyl)amino)butyl)-12-isobutyl-2,2-dimethyl-4,7,10,13-tetraoxo-3-oxa-5,8,11,14-tetraazahexadecan-16-oate

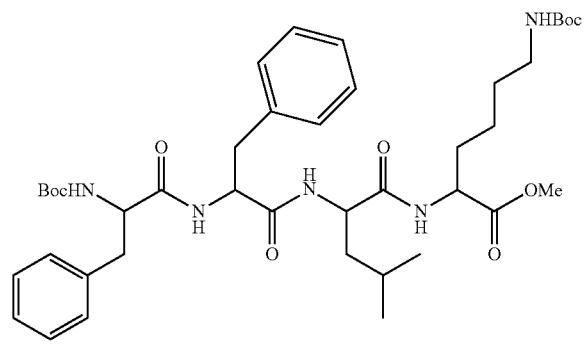 [SMILES: COC(=O)C(CCCCNC(=O)OC(C)(C)C)NC(=O)C(CC(C)C)NC(=O)C(Cc1ccccc1)NC(=O)C(Cc1ccccc1)NC(=O)OC(C)(C)C]

To a solution of 6,9-dibenzyl-12-isobutyl-2,2-dimethyl-4,7,10-trioxo-3-oxa-5,8,11-triazatridecan-13-oic acid (1.0 g, 1.90 mmol) in DCM (10 ml), HOBt (0.26 g, 1.90 mmol) and DCC (0.39 g, 1.90 mmol) was added at 25-30° C. The mixture was stirred for 10 min., and to it H₂N-Lys(Boc)—OMe (0.49 g, 1.90 mmol) was added. The reaction mixture was stirred for 24 h at 25-30° C., filtered and the filtrate was diluted with DCM. Organic layer was washed with saturated NaHCO₃ solution, citric acid solution and brine, dried over Na₂SO₄ and evaporated to get the crude product. Crude product was purified by column chromatography using 0 to 2% MeOH in DCM as an eluent system, to get the title compound as a white solid (1.34, 92% yield); ESI-MS: 768.4 (M+H⁺).

Step vi: Synthesis of 6,9-dibenzyl-15-(4-((tert-butoxycarbonyl)amino)butyl)-12-isobutyl-2,2-dimethyl-4,7,10,13-tetraoxo-3-oxa-5,8,11,14-tetraazahexadecan-16-oic acid

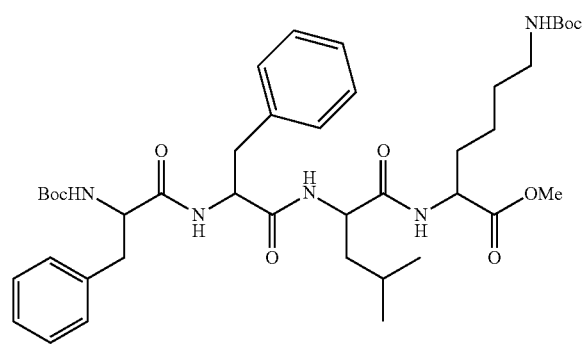 [SMILES: COC(=O)C(CCCCNC(=O)OC(C)(C)C)NC(=O)C(CC(C)C)NC(=O)C(Cc1ccccc1)NC(=O)C(Cc1ccccc1)NC(=O)OC(C)(C)C]

To a solution of methyl 6,9-dibenzyl-15-(4-((tert-butoxycarbonyl)amino)butyl)-12-isobutyl-2,2-dimethyl-4,7,10,13-tetraoxo-3-oxa-5,8,11,14-tetraazahexadecan-16-oate (1.0 g, 1.33 mmol) in MeOH (10 ml), NaOH (0.11 g, 2.66 mmol) in H₂O (5 ml) was added at 25-30° C. The reaction mixture was stirred for 1 h at 25-30° C. After 1 h MeOH was evaporated & aqueous layer was acidified with citric acid solution, solid was obtained. Filter the solid & dried it to get the title compound as a white solid (0.95 g, 97% yield); ESI-MS: 754.4 (M+H⁺).

Step vii: Synthesis of bis-Boc-N-(6-amino-1-(3-benzyl-3,6-diazabicyclo[3.1.1]heptan-6-yl)-1-oxohexan-2-yl)-2-(2-(2-amino-3-phenylpropanamido)-3-phenylpropanamido)-4-methylpentanamide

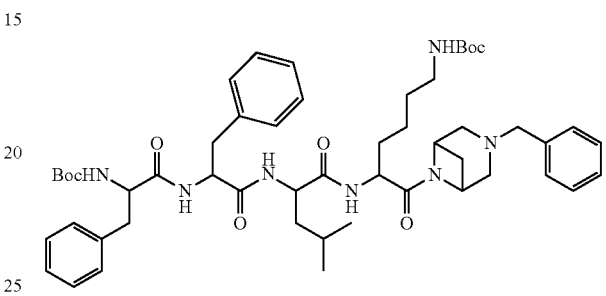

To a solution of 6,9-dibenzyl-15-(4-((tert-butoxycarbonyl)amino)butyl)-12-isobutyl-2,2-dimethyl-4,7,10,13-tetraoxo-3-oxa-5,8,11,14-tetraazahexadecan-16-oic acid (0.2 g, 0.26 mmol) in DCM (2 ml), HOBt (0.04 g, 0.26 mmol) and DCC (0.06 g, 0.26 mmol) was added at 25-30° C. The mixture was stirred for 10 min., and to it 3-benzyl-3,6-diazabicyclo[3.1.1]heptane (0.05 g, 0.26 mmol)[prepared according to ref: TL 53, 6332-6334, 2012] was added. The reaction mixture was stirred for 24 h at 25-30° C., filtered and the filtrate was diluted with DCM. Organic layer was washed with saturated NaHCO₃ solution, citric acid solution and brine, dried over Na₂SO₄ and evaporated to get the crude product. Crude product was purified by column chromatography using 0 to 3% MeOH in DCM as an eluent system, to get the title compound as a white solid (0.22 g, 89% yield); ESI-MS: 924.6 (M+H⁺).

Step viii: Synthesis of N-(6-amino-1-(3-benzyl-3,6-diazabicyclo[3.1.1]heptan-6-yl)-1-oxohexan-2-yl)-2-(2-(2-amino-3-phenylpropanamido)-3-phenylpropanamido)-4-methylpentanamide

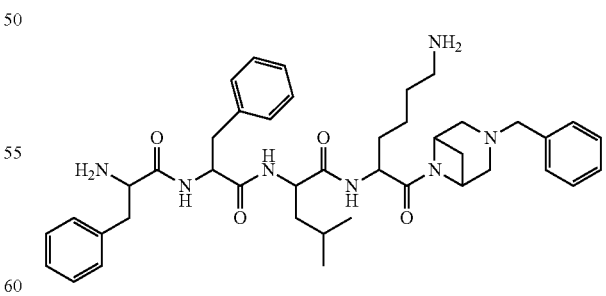

To a solution of bis-Boc-N-(6-amino-1-(3-benzyl-3,6-diazabicyclo[3.1.1]heptan-6-yl)-1-oxohexan-2-yl)-2-(2-(2-amino-3-phenylpropanamido)-3-phenylpropanamido)-4-methylpentanamide (0.18 g, 0.19 mmol) in DCM (2 ml), TFA (2 ml) was added at 25-30° C. The reaction mixture was stirred for 3 h at 25-30° C. After 3 h solvent was evaporated, residue obtained was washed with diethylether. The crude compound was purified by preparative HPLC, pure fractions were collected & lypholized it to get title compound as a white solid (0.12 g, 84% yield); ESI-MS: 725.0 (M+H$^+$).

The other compounds of the invention as described in Table-1 were synthesized by the processes described above in combination with routine variations as were necessary, which are well within the scope of a skilled person. The compounds were characterized through mass spectra which are provided below (Table-3).

The mass spectral data of representative compounds are listed in Table-3

TABLE 3

Mass spectral [ESI-MS] data of representative compounds

| Compd No. | ESI-MS [M + H]$^+$ | Compd No. | ESI-MS [M + H]$^+$ | Compd No. | ESI-MS [M + H]$^+$ |
|---|---|---|---|---|---|
| 1 | 646.5 | 2 | 660.4 | 3 | 733.0 |
| 4 | 703.8 | 5 | 702.6 | 6 | 690.6 |
| 7 | 724.6 | 8 | 754.5 | 9 | 795.0 |
| 10 | 704.6 | 11 | 716.5 | 12 | 702.8 |
| 13 | 648.7 | 14 | 662.4 | 15 | 734.9 |
| 16 | 706.9 | 17 | 706.8 | 18 | 692.8 |
| 19 | 726.8 | 20 | 755.6 | 21 | 718.8 |
| 22 | 704.3 | 23 | 661.7 | 24 | 663.6 |
| 25 | 673.2 | 26 | 676.9 | 27 | 719.7 |
| 28 | 691.3 | 29 | 690.4 | 30 | 677.4 |
| 31 | 662.4 | 32 | 634.9 | 33 | 647.9 |
| 34 | 725.0 | 35 | 720.5 | 36 | 692.4 |
| 37 | 691.4 | 38 | 678.6 | 39 | 712.6 |
| 40 | 741.9 | 41 | 705.6 | 42 | 690.7 |
| 43 | 719.0 | 44 | 717.6 | 45 | 706.6 |
| 46 | 706.8 | 47 | 684.7 | 48 | 684.6 |
| 49 | 782.4 | 50 | 794.4 | 51 | 633.4 |
| 52 | 720.4 | 53 | 692.7 | 54 | 691.5 |
| 55 | 705.0 | 56 | 782.4 | 57 | 706.9 |
| 58 | 706.8 | 59 | 678.4 | 60 | 634.8 |
| 61 | 648.5 | 62 | 724.4 | 63 | 721.0 |
| 64 | 693.3 | 65 | 691.4 | 66 | 680.0 |
| 67 | 648.6 | 68 | 662.4 | 69 | 734.4 |
| 70 | 706.9 | 71 | 705.3 | 72 | 692.4 |
| 73 | 726.3 | 74 | 755.5 | 75 | 119.0 |
| 76 | 704.4 | 77 | 648.4 | 78 | 662.6 |
| 79 | 734.4 | 80 | 706.9 | 81 | 705.4 |
| 82 | 692.4 | 83 | 718.8 | 84 | 705.0 |
| 85 | 648.4 | 86 | 738.6 | 87 | 706.4 |
| 88 | 705.4 | 89 | 650.3 | 90 | 708.6 |
| 91 | 662.3 | 92 | 720.5 | 93 | 747.8 |
| 94 | 792.0 | 95 | 749.0 | 96 | 763.7 |
| 97 | 721.5 | 98 | 733.0 | 99 | 807.3 |
| 100 | 835.3 | 101 | 780.4 | 102 | 807.4 |
| 103 | 821.3 | 104 | 821.8 | 105 | 663.8 |
| 106 | 662.4 | 107 | 704.6 | 108 | 720.3 |
| 109 | 662.3 | 110 | 720.3 | 111 | 663.8 |
| 112 | 662.6 | 113 | 705.0 | 114 | 720.4 |
| 115 | 662.6 | 116 | 720.8 | | |

The synthesized compounds were tested for their biological activities as provided below:

Biological Activity Screening:

a) In Vitro (EC$_{50}$) Determination, Using cAMP Based Functional Assay:

In vitro, KOR agonistic activity of test compounds were assessed using cAMP based functional assay. A 96-well plate was seeded at the density of 30,000 cells/well in 100 µl/well of complete Ham's F-12 medium. After seeding, the plates were incubated overnight at 37° C., 5% CO$_2$, in CO$_2$ Incubator. Overnight medium was discarded and plate washed with 100 µl/well of sterile PBS. Then 90 µl of 0.1 mM IBMX containing 0.5% Fatty acid free BSA in plain HamsF12 was added to each well. This was allowed to incubate for 30 minutes at 37° C., 5% CO$_2$. Forskolin 20 µM in 0.5% Fatty acid free BSA was added to each well and allowed to incubate at room temperature for 5 minutes. Dilution of test compounds was made at 200× in DMSO and then diluted 1:10 times in BSA containing plain HamsF12. Agonist (test compounds, in 10% DMSO) was added to each well (5 µl) and allowed to incubate for 20 minutes at 37° C., 5% CO$_2$. After 20 minutes, media was aspirated from the wells and the wells were washed with 1×PBS. Cell lysis buffer 4× (Arbor Assays, Cat # X074-60 ML) was diluted 1:4 in MilliQ and 90 µl of this buffer was added per well. Cells were allowed to shake at 500 rpm, room temperature for 20 minutes. Cell lysate was collected in 1.5 ml eppendorf tubes and centrifuged at 13.2 k rpm, 4° C. for 15 minutes. 50 µl of the supernatant of cell lysate was then used for cAMP estimation by cAMP direct ELISA kit (Arbor Assays, Cat # K019-H5). The in vitro kappa opioid receptor agonistic activities (EC$_{50}$) for representative compounds are listed in Table 4

TABLE 4

In-vitro (EC$_{50}$) data of representative compounds

| Compd No. | In-vitro EC$_{50}$ PM |
|---|---|
| 4 | 47 |
| 5 | 9 |
| 10 | 400 |
| 15 | 7 |
| 16 | 4 |
| 17 | 380 |
| 23 | 85 |
| 26 | 220 |
| 27 | 9 |
| 32 | 20 |
| 33 | 9 |
| 34 | 88 |
| 35 | 10 |
| 36 | 15 |
| 37 | 83 |
| 41 | 15 |
| 49 | 16 |
| 50 | 8 |
| 51 | 12 |
| 92 | 18 |
| 99 | 16 |
| 100 | 15 |
| 101 | 12 |
| 102 | 12 |
| 105 | 2 |

Test compounds of the invention were tested in a similar assay for potency on the human mu and delta opioid receptors. Each compound tested had and EC$_{50}$, for the human mu and delta opioid receptors greater than or equal to 10 µM, which indicates selective kappa opioid receptor agonistic activity.

In Vivo Efficacy Studies:

Animals

Animals were housed in groups of 6 animals per cage, for a week, in order to habituate them to vivarium conditions (25±4° C., 60-65% relative humidity, 12:12 h light: dark cycle, with lights on at 7.30 am). All the animal experiments were carried out according to the internationally valid guidelines following approval by the 'Zydus Research Center animal ethical committee'.

Pain Models

In Vivo (ED$_{50}$) Determination, Using Acetic Acid-Induced Writhing Model

The acetic acid induced writhing assay can detect antinociceptive activity for opioid drug, acting at peripheral, spinal and supraspinal levels. Animals were fasted 12 to 16 h prior testing. The nociceptive response (abdominal contractions or writhes) was induced by diluted acetic acid (0.6%, 10 ml/kg, for mice and 2.5%, 0.5 ml/rat) administered intraperitoneally (i.p.) at time 0 min.

In mouse experiments, compounds were administered orally, intravenously (i.v.) or subcutaneously (s.c.). To determine the antinociceptive potency and efficacy, full dose-response curves were constructed with test compounds, given 5 min prior to acetic acid administration. The duration of action was determined by using increasing pretreatment time (5, 60, and 120 min.), prior to acetic acid administration, for a sub-maximally effective dose defined during the dose-response curve study. In rat experiments, compounds were administered orally, intravenously (i.v.) or subcutaneously (s.c.), 15 min prior to acetic acid administration. The number of writhes was counted over the 15 min period following acetic acid administration. A writhe is defined as a constriction of the abdominal area, often with extension of the hind legs. Percentage maximum possible effect (MPE) was calculated as: % MPE=100−[(No. of writhes in test compound treated animal/No. of writhes in vehicle treated animal)]×100. $ED_{50}$ dose was determined using GraphPad Prism. Representative data ($ED_{50}$) of some of the test compounds are listed in Table-5.

TABLE 5

In-vivo $ED_{50}$ in acetic acid induced pain model data of representative compounds, in ICR mice (n = 6)

| Compound No. | In-vivo $ED_{50}$ (mpk, iv) |
| --- | --- |
| 4 | 0.09 |
| 5 | 0.07 |
| 13 | 1 |
| 15 | 0.1 |
| 16 | 0.1 |
| 18 | 1 |
| 19 | 0.28 |
| 35 | 0.03 |
| 36 | 0.04 |
| 37 | 0.08 |
| 38 | 0.04 |
| 39 | 0.18 |
| 42 | 0.23 |
| 57 | 0.26 |
| 62 | 0.31 |
| 64 | 0.16 |
| 90 | 0.98 |
| 93 | 0.11 |
| 97 | 0.42 |
| 104 | 0.07 |

Assessment of CNS Effects of Test Compounds

Test compounds were dissolved in normal saline, administered orally, intravenously (i.v.) or subcutaneously (s.c.) routes. The first dose of 3 mg/kg was injected and animal (rat or mice) was observed for spontaneous locomotion, sedation and catalepsy. The dose is scaled down or up if pharmacodynamic effect is present or absent respectively. The lowest dose which shows pharmacodynamic effect was considered threshold dose (TD).

Analgesic Effect Vs Sedative Effects of Test Compounds:

Inhibition of acetic acid induced writhing by test compound is an indication of an analgesic effect, while reduction in spontaneous locomotion, sedation and catalepsy, caused by test compound can be used as a measure of its general sedative effect. Safety Index (SI) can be calculated as ratio of TD vs $ED_{50}$ doses. Representative compounds (Compound 4, 5, 15, 35 and 36) showed 50-100 fold safety index, which indicates that test compounds are devoid of CNS side effects, mainly associated with other opioid receptor agonist.

These compounds are useful in alleviating the pain and suffering inflicted by chronic inflammatory diseases such as rheumatoid arthritis as well as the treatment of gastrointestinal motility disorders such as ileus induced by surgery or peritonitis. A preferred utility is to produce peripheral analgesia without the CNS-mediated side effects of opioids. For example, the abdominal pain induced by laproscopic surgery can be reduced.

The present invention provides a method of treating or preventing a kappa opioid receptor-associated disease or condition in a mammal, such as a human, wherein the method includes administering to the mammal a composition comprising an effective amount of compounds of the general formula (I) of the invention. In another embodiment the kappa opioid receptor-associated conditions are pain, inflammation, pruritis, edema, ileus, tussis or glaucoma.

The novel compounds of the present invention can be formulated into suitable pharmaceutically acceptable compositions by combining with suitable excipients by techniques and processes and concentrations as are well known.

The compounds of formula (I) or pharmaceutical compositions containing them are useful as a medicament as KOR agonist and suitable for humans and other warm blooded animals, and may be administered either by oral, topical or parenteral administration.

Thus, a pharmaceutical composition comprising the compounds of the present invention may comprise a suitable binder, suitable bulking agent &/or diluent and any other suitable agents as may be necessary. Optionally, the pharmaceutical composition may be suitably coated with suitable coating agents.

The compounds of the present invention (I) are KOR agonist and are useful in the treatment or prevention of diseases in which the Kappa (κ) opioid receptors (KOR) are involved, such as treatment or prevention of visceral pain, hyperalgesia, rheumatoid arthritic inflammation, osteoarthritic inflammation, IBD inflammation, IBS inflammation, ocular inflammation, otitic inflammation or autoimmune inflammation.

In one of the embodiments, the present invention of formula (I) can be co-administered in combination with one or more suitable pharmaceutically active agents. In a particular embodiment, the pharmaceutical compositions of the invention can be co-administered with or can include one or more other therapeutic compounds or adjuvants, such as but not limited to other opioids, cannabinoids, antidepressants, anticonvulsants, neuroleptics, antihistamines, acetaminophen, corticosteroids, ion channel blocking agents, non-steroidal anti-inflammatory drugs (NSAIDs) and diuretics, many of which are synergistic in effect with the compounds of the present invention.

Suitable opioids, include, without limitation, alfentanil, alphaprodine, anileridine, bremazocine, codine, dextromoramide; dezocine, diamorphine, dihydrocodeine, dihydromorphine, ethylketazocine, ethylmorphine, fentanyl, hydrocodone, hydromorphone, loperamide, methadone, morphine, nalorphine, oxycodone, oxymorphone, propiram and tramadol.

One embodiment of the invention is co-formulation and/or co-administration of compounds of formula (I) with mu opioid receptor agonist, such as morphine, fentanyl or oxycodone, for the purpose of a mu opioid dose-sparing effect, where the dose of the mu opioid is reduced to minimize common mu opioid side effects, which include constipation, nausea, vomiting, sedation, respiratory depression, itching, mental confusion and seizures.

Suitable antidepressants that can be co-administered with or incorporated into the pharmaceutical compositions of the invention include for example, tricyclic antidepressants such as imipramine, desipramine, trimipramine and clomipramine. Suitable neuroleptics that can be co-administered with or incorporated into the pharmaceutical compositions of the invention include any neuroleptic, for example a compound with D2 dopamine receptor antagonist activity such as domperidone, metoclopramide, zotepine, chlorpromazine, acetophenazine, prochlorperazine and thiothixene. Anticonvulsants such as phenobarbital, phenytoin, carbamazepine, valporic acid, gabapentin and topiramate can also be incorporated into the pharmaceutical compositions of the invention. Muscle relaxants such as methocarbamol, diazepam and chlorzoxazone; anti-migraine agents such as sumitriptan, analeptics sucah as caffeine; antihistamines such as chloropheniramine and pyrilamine; ion channel blocking agents such as sodium ion channel blocker, carbamazepine, calcium ion channel blocker, such as ziconotide; suitable NSAIDs such as aminoarylcarboxylic acid derivatives, arylacetic acid derivatives, arylbutyric acid derivatives, arylpropionic acid derivatives, phenylalkanoic acid derivatives and salicylic acid derivatives, as well as corticosteroids such as methyl-prednisolone, hydrocortisone, cortisone and triameinolone can be incorporated into the pharmaceutical compositions of the present invention.

The quantity of active component, that is, the compounds of Formula (I) according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

While the present invention has been described in terms of its specific embodiments, certain modifications and equivalents will be apparent to those skilled in the art and are intended to be included within the scope of the present invention.

We claim:

1. An isolated short-chain peptides having general formula (I)

A-B-C-D-E    (Formula I)

or their tautomeric forms, their enantiomers, their diastereoisomers, their stereomers, their pharmaceutical acceptable salt and pharmaceutical compositions containing them wherein, each of 'A' and 'B' at each occurrence is independently selected from Phe, α-Me-Phe, Tyr, Phenylglycine, Homophenylalanine, Cyclohexylglycine, Cyclohexylalanine, Wherein, the aromatic ring present in any of these amino acids can be substituted with H, Halo, $NO_2$, $NH_2$, alkyl, $CF_3$ and CN, 'C' is selected from Norleucine, Phe, Ala, Leu, α-Me-Leu, homoleucine, Val, 1-Aminocyclohexane carboxylic acid, 1-Aminocyclopentane carboxylic acid, Cyclohexylglycine;

'D' is selected from the group consisting of Arg, Lys, Har, Orn, Ala, Hlys, Norleucine, His;

'E' is selected from group consisting of:

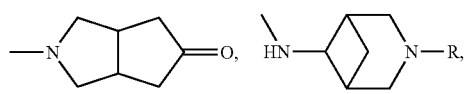

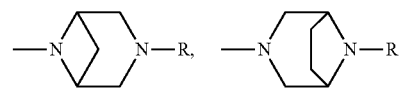

Where R at each occurrence is selected from H, —NR'R", —CN, —COOR', —CONR'R", —CO($CH_2$)$_n$—OR', —OR', —($CH_2$)$_n$OR', —$SO_2$R' or $SO_2$NR'R", —($CH_2$)$_n$COOR', —($CH_2$)$_n$CONR'R", —($CH_2$)$_n$NR'R", —NH($CH_2$)$_n$COOR', —($CH_2$)$_n$CONHR, $CH_2$CON[($CH_2$)$_n$COOR']$_2$, —$CH_2$CON[($CH_2$)$_n$OR']$_2$, —COCH$_2$N[($CH_2$)$_n$COOR']$_2$, —CO($CH_2$)$_n$—NR'R", —CO($CH_2$)$_n$COOR', —CO($CH_2$)$_n$CONR'R", —($CH_2$)$_n$CONHNR'R", —CO($CH_2$)$_n$CONHNR'R", —($CH_2$)$_n$NHNR'R", —($CH_2$)$_n$CN, —$CHR_1$COOR', —$CR_1R_2$COOR', -alkylaryl, aryl, $C_1$-$C_{10}$ alkyl, amidino, $C_1$-$C_6$ alkyl-substituted amidino, wherein each of R' and R" at each occurrence can be independently or both selected from H, $C_1$-$C_{10}$ alkyl, branched alkyl, alkylaryl, aryl, or R' and R" may be combined to form a 4 to 6 membered ring; n=1 to 10, wherein $R_1$ & $R_2$ in each occurrence can be independently or both selected from alkyl & halogen;

In an alternate embodiment, each of R & R' may also represent amino acids selected from the group consisting of Asp, Glu, Asn, Gln, Lys, Arg, His, Ala, Ser, Thr, Leu, Val, Gly, Har, 2-amino heptanedioic acid.

2. The peptide according to claim 1 wherein each of 'A' and B is independently selected from Phe and Tyr.

3. The peptide according to claim 1 wherein C is selected from Leu, Norleucine and 1-Aminocyclohexane carboxylic acid.

4. The peptide according to claim 1 wherein D is selected from Lys, Arg and Ala.

5. The Peptide of formula (I) as claimed in claim 1 selected from

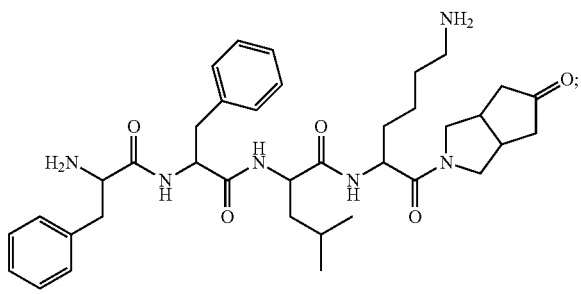

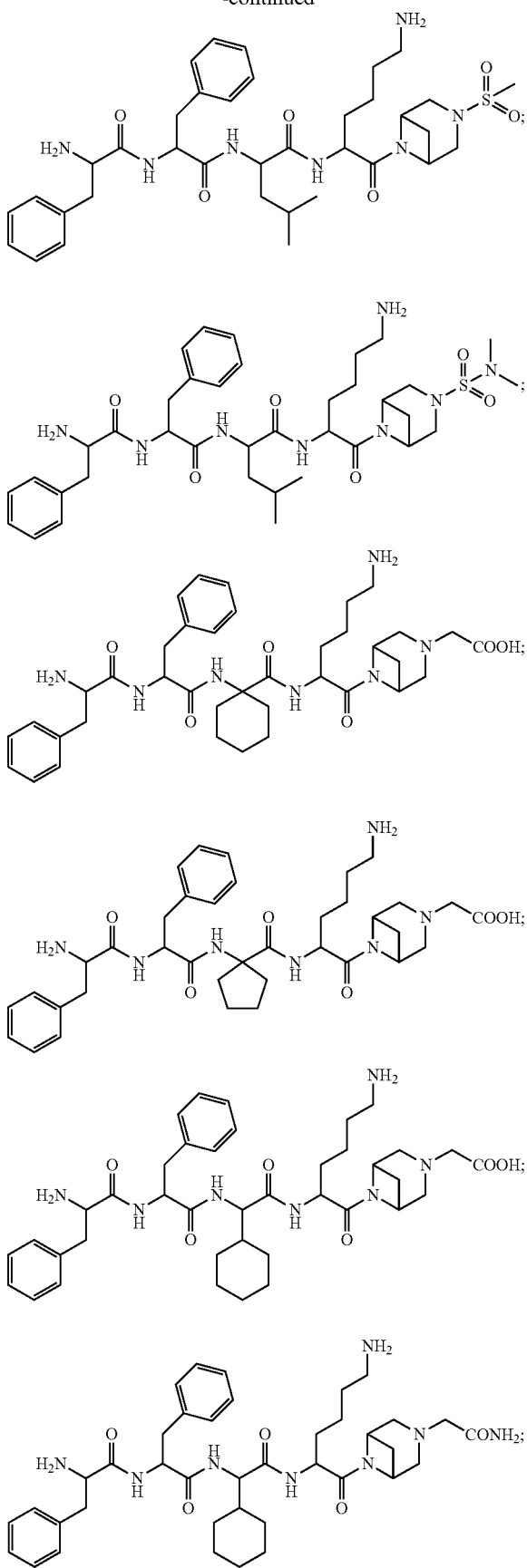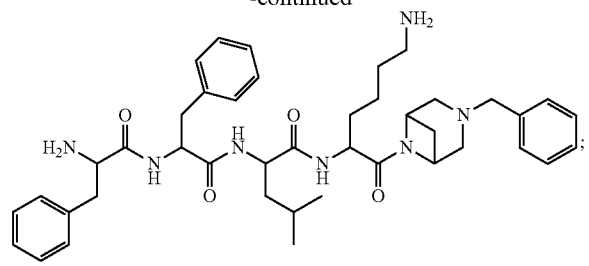

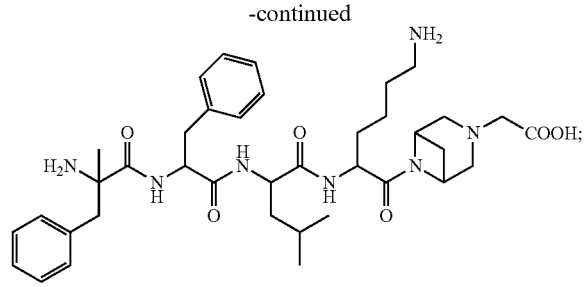
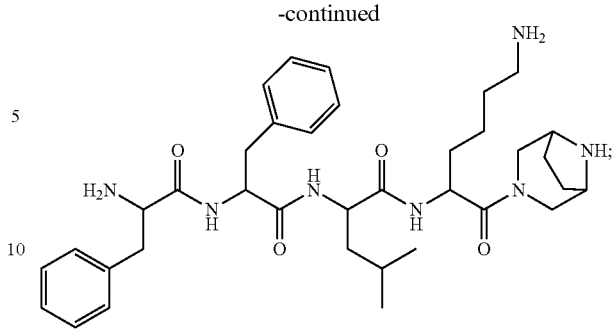
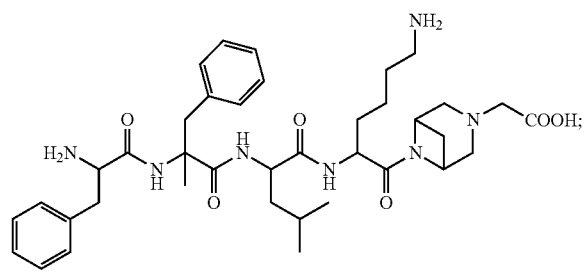
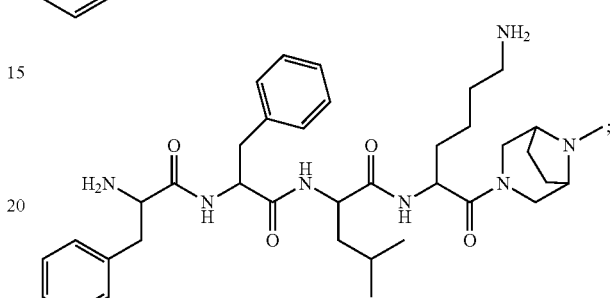
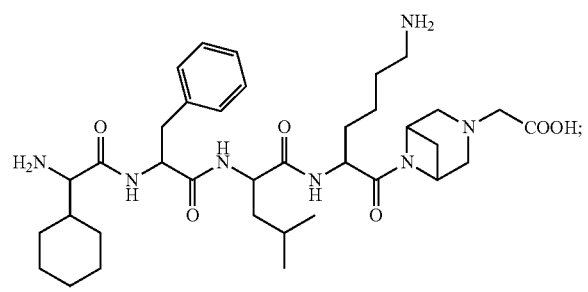
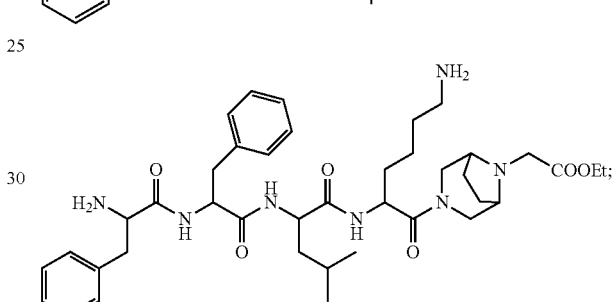
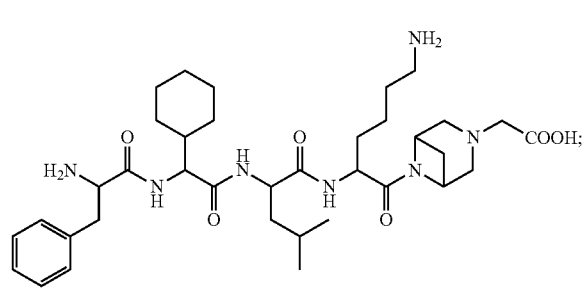
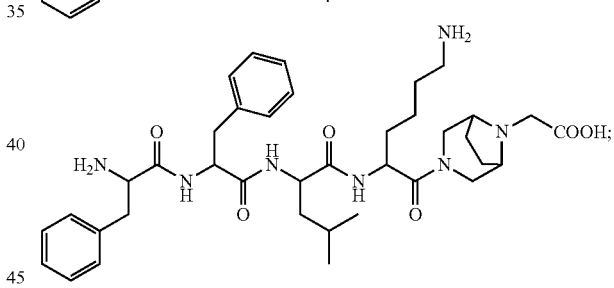
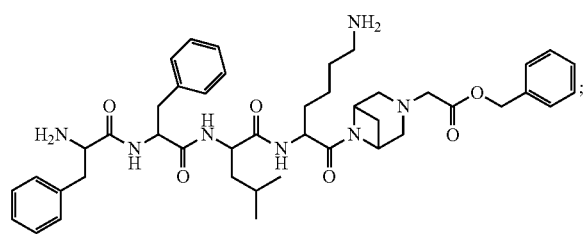
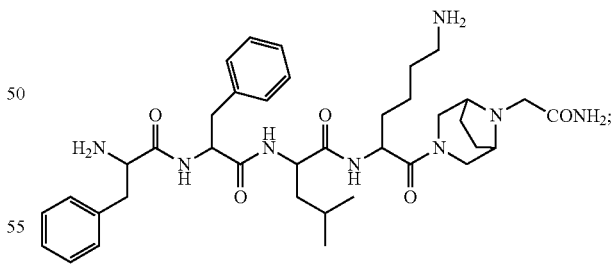
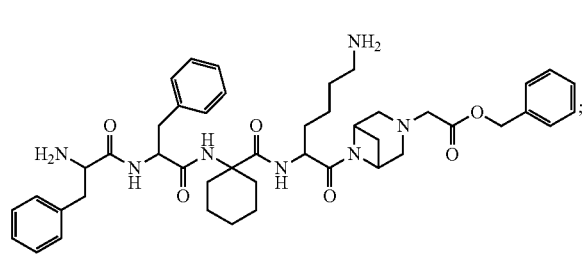
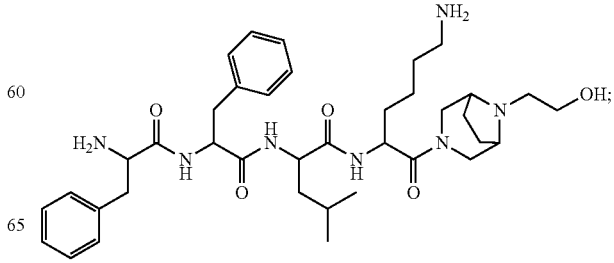

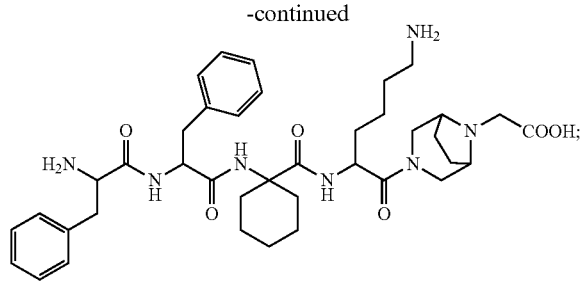
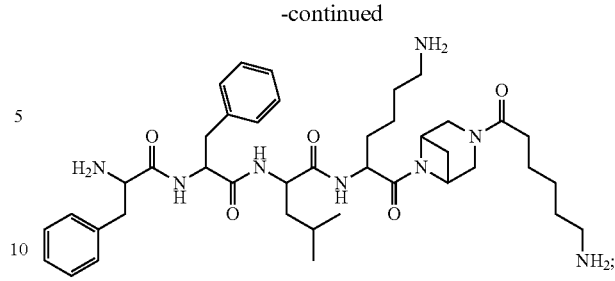
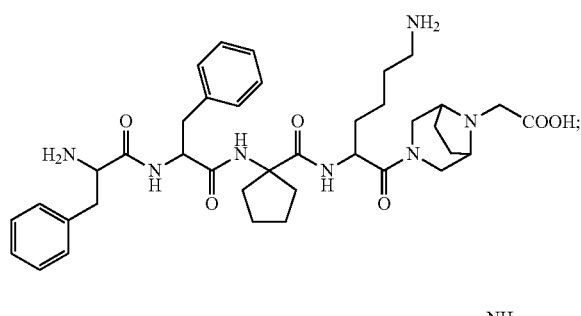
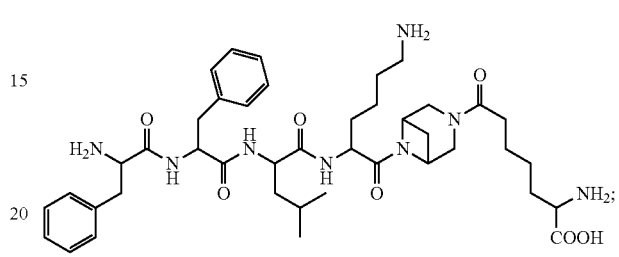
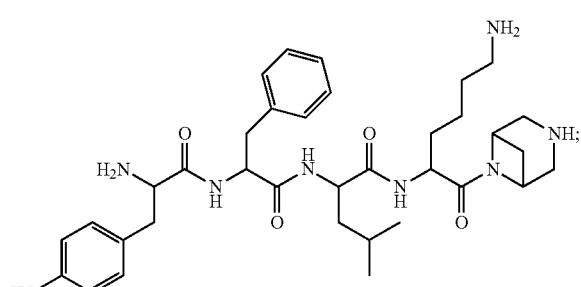
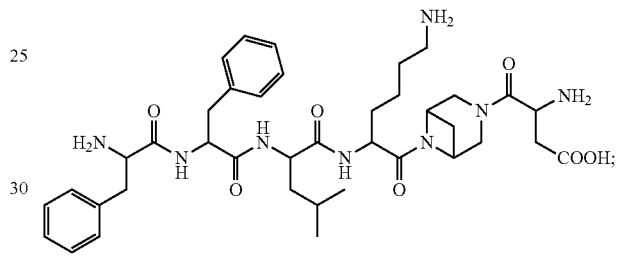
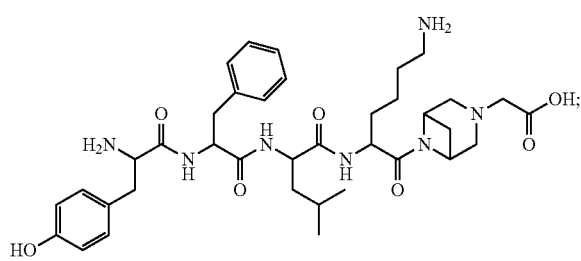
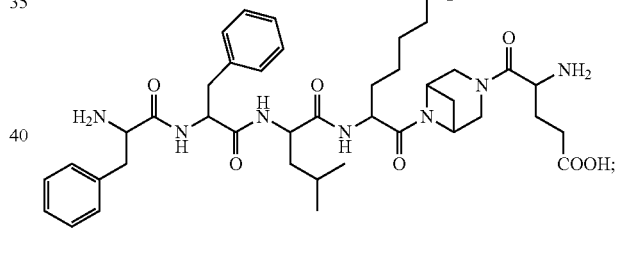
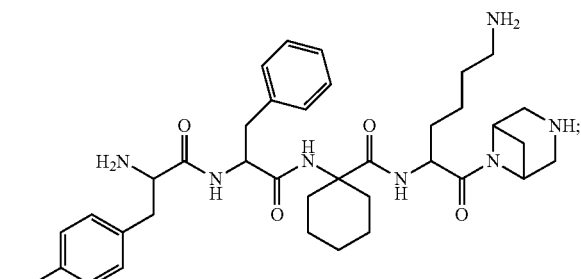
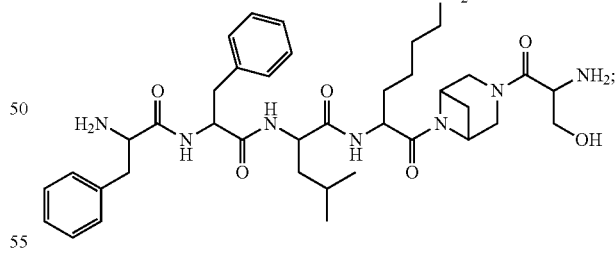
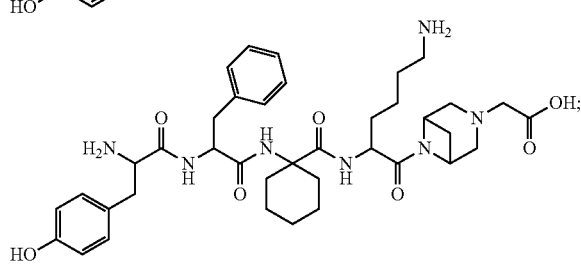
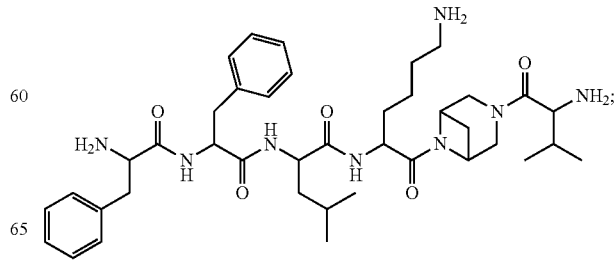

-continued

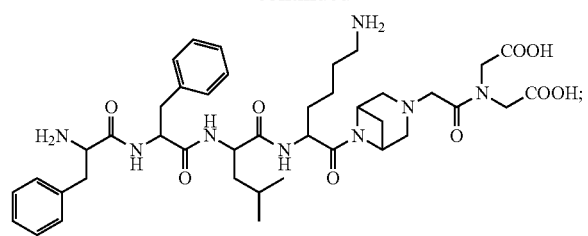

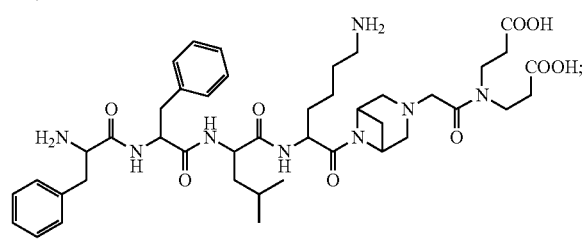

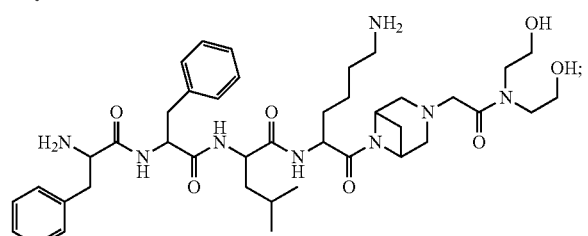

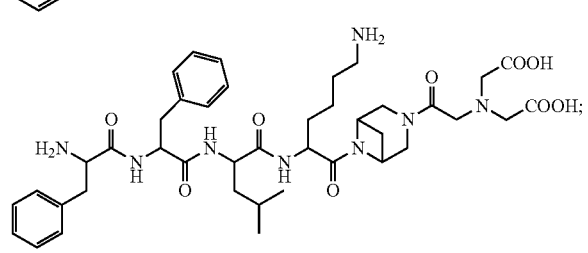

-continued

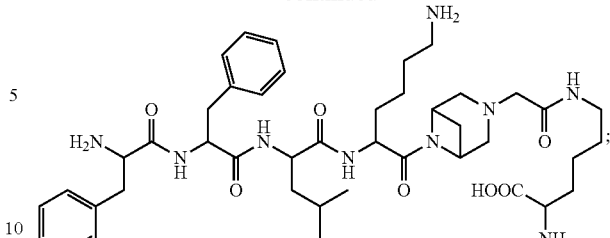

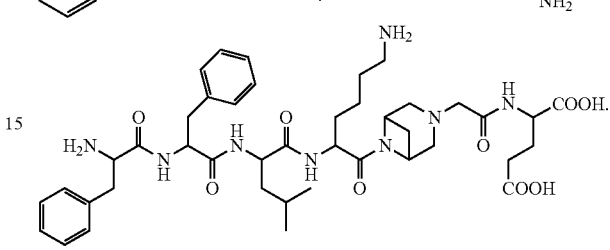

6. A pharmaceutical composition comprising a therapeutically effective amount of a compound of formula (I) as claimed in claim 1 and optionally one or more pharmaceutically acceptable carriers, diluents or excipients.

7. A method of treating or preventing a visceral pain, hyperalgesia, rheumatoid arthritis inflammation, osteoarthritic inflammation, IBD inflammation, IBS inflammation, ocular inflammation, otitis inflammation or autoimmune inflammation which comprising administering to a patient in need thereof an effective amount of a compound of formula (I) as claimed in claim 1.

8. The pharmaceutical composition as claimed in claim 6 in combination with suitable opioids, cannabinoids, antidepressants, anticonvulsants, neuroleptics, antihistamines, acetaminophen, corticosteroids, ion channel blocking agents, non-steroidal anti-inflammatory drugs (NSAIDs) and diuretics.

\* \* \* \* \*